US00RE47451E

(19) United States
(12) Reissued Patent
Bae et al.

(10) Patent Number: US RE47,451 E
(45) Date of Reissued Patent: Jun. 25, 2019

(54) THIENO[3,2-D]PYRIMIDINE DERIVATIVES HAVING INHIBITORY ACTIVITY FOR PROTEIN KINASES

(71) Applicant: Hanmi Pharm. Co. Ltd., Hwaseong-Si, Gyenoggi-Do (KR)

(72) Inventors: In Hwan Bae, Hwaseong-si (KR); Jung Beom Son, Hwaseong-si (KR); Sang Mi Han, Seoul (KR); Eun Joo Kwak, Hwaseong-si (KR); Ho Seok Kim, Hwaseong-si (KR); Ji Young Song, Seoul (KR); Eun Young Byun, Yongin-si (KR); Seung Ah Jun, Hwaseong-si (KR); Young Gil Ahn, Seongnam-si (KR); Kwee Hyun Suh, Suwon-si (KR)

(73) Assignee: Hanmi Pharm. Co. Ltd., Hwaseong-Si, Gyenoggi-Do (KR)

(21) Appl. No.: 15/783,240

(22) Filed: Oct. 13, 2017

Related U.S. Patent Documents

Reissue of:
(64) Patent No.: 9,156,852
Issued: Oct. 13, 2015
Appl. No.: 14/363,857
PCT Filed: Dec. 27, 2012
PCT No.: PCT/KR2012/011571
§ 371 (c)(1),
(2) Date: Jun. 9, 2014
PCT Pub. No.: WO2013/100632
PCT Pub. Date: Jul. 4, 2013

(30) Foreign Application Priority Data

Dec. 30, 2011 (KR) ..... 10-2011-0146818

(51) Int. Cl.

| | |
|---|---|
| ***C07D 495/04*** | (2006.01) |
| ***C07D 417/12*** | (2006.01) |
| ***A61K 31/519*** | (2006.01) |
| ***A61P 35/00*** | (2006.01) |
| ***C07D 519/00*** | (2006.01) |
| ***A61K 45/06*** | (2006.01) |
| ***A61K 31/5377*** | (2006.01) |

(52) U.S. Cl.
CPC ..... *C07D 495/04* (2013.01); *A61K 31/519* (2013.01); *A61K 31/5377* (2013.01); *A61K 45/06* (2013.01); *C07D 519/00* (2013.01)

(58) Field of Classification Search
CPC ..... C07D 495/04; C07D 519/00; A61K 31/5377; A61K 45/06; A61K 31/519
USPC ..... 544/278; 514/258.1
See application file for complete search history.

(56) References Cited

U.S. PATENT DOCUMENTS

| | | | | |
|---|---|---|---|---|
| 8,633,201 | B2 | 1/2014 | Aicher et al. | |
| 9,255,110 | B2 * | 2/2016 | Arora | C07D 495/04 |
| 2012/0277424 | A1 | 11/2012 | Sim et al. | |
| 2013/0012703 | A1 | 1/2013 | Sim et al. | |

FOREIGN PATENT DOCUMENTS

| | | | |
|---|---|---|---|
| CA | 2634769 | A1 | 7/2007 |
| EA | 200802118 | A1 | 4/2009 |
| KR | 20110044053 | A | 4/2011 |
| KR | 20110055202 | A | 5/2011 |
| KR | 20110089108 | A | 8/2011 |
| RU | 2528046 | C2 | 9/2014 |
| WO | 2010101302 | A1 | 9/2010 |
| WO | 2011025940 | A1 | 3/2011 |
| WO | 2011093672 | A2 | 8/2011 |
| WO | 2011093684 | A2 | 8/2011 |

OTHER PUBLICATIONS

Qui, Y., Oncogene 19, 2000, pp. 5651-5661.
International Search Report and Written Opinion for PCT/KR2012/011571, dated Apr. 30, 2013, 8 pages.
Israeli Patent Office, Communication dated Apr. 20, 2015, issued in Counterpart Israeli Application No. 233441, 10 pages.
Supplementary European Search Report for EP 12 86 1811 issued Jun. 5, 2015, 5 pages.
Cecil Textbook of Medicine, edited by Bennet, J.C., and Plum F., 20th edition,vol. 1, 1004-101 O, 1996.*
Mass, R. D., Int. J. Radiation Oncology Bio. Phys.vol. 58(3): 932-940, 2004.*
Fabbro et al. Pharmacology & therapeutics 93, 79-98, 2002.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Ferrara, N, Oncology, 69 Suppl. 3, 11-16, 2005.*
Jain et al., Nature Clinical Practice Oncology, 3(1), 24-40, 2006.*
Gautschi et al., Clin. Cancer Res., 14(6), 1639-1648, 2008.*
Mountzios et al., Cancer Treatments Reviews, 34, 175-182, 2008.*
Qiu Y., © ncogene 19, 5651-5661,2000.*
Pyne et al. Cancer Res 2011 ;71:6576-6582.*

* cited by examiner

*Primary Examiner* — Dwayne C. Jones
(74) *Attorney, Agent, or Firm* — Armstrong Teasdale LLP

(57) ABSTRACT

Provided are a thieno[3,2-d]pyrimidine derivative of formula (I) or a pharmaceutically acceptable salt thereof having inhibitory activity for protein kinase, and a pharmaceutical composition comprising same for prevention and treatment of abnormal cell growth diseases.

63 Claims, No Drawings

THIENO[3,2-D]PYRIMIDINE DERIVATIVES HAVING INHIBITORY ACTIVITY FOR PROTEIN KINASES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

This application *is a reissue application of U.S. Pat. No. 9,156,852 B2 which* is a National Stage of International Application No. PCT/KR2012/011571 filed Dec. 27, 2012, *filed as U.S. application Ser. No. 14/363,857,* claiming priority based on Korean Patent Application No. 10-2011-0146818 filed Dec. 30, 2011, the contents [of all] of which are incorporated [herein] by reference in their entirety.

FIELD OF THE INVENTION

The present invention relates to thieno[3,2-d]-pyrimidine derivatives and pharmaceutically acceptable salts thereof having inhibitory activity for protein kinases, and a pharmaceutical composition comprising same as an active ingredient for prevention and treatment of diseases caused by abnormal cell growth of protein kinases.

BACKGROUND OF THE INVENTION

A protein kinase is an enzyme, which plays a key role in mediation of signal transduction via phosphorylation of a hydroxyl group present in a tyrosine, serine or threonine residue, and, thus, is deeply involved in the regulation of cell growth, differentiation, proliferation, etc.

As is well known, a balance between "on-states" and "off-states" of an intracellular signaling pathway is essential for maintenance of homeostasis of a cell. When a normal intracellular signaling pathway of, e.g., mostly continuation of "on-state" of intracellular signals is interrupted due to overexpression or mutation of a specific protein kinase, it may lead to an outbreak of various diseases such as cancer, inflammatory disease, metabolic disease and brain disease. It is estimated that human genome contains 518 protein kinases which constitute approximately 1.7% of all human genes [Manning et al., Science, 298, (2002), 1912]; and the protein kinases can be divided into tyrosine protein kinases (90 or more types) and serine/threonine protein kinases. The tyrosine protein kinases can be divided into receptor tyrosine kinases including 58 distinct kinases which can be further categorized into 20 subtypes, and cytoplasmic/non-receptor tyrosine kinases including 32 distinct kinases which can be further categorized into 10 subtypes. A receptor tyrosine kinase has a kinase domain on the surface where it can bind a growth factor, and an active site where phosphorylation of a tyrosine residue takes place. Binding of a growth factor to the extracellular domain of the receptor may cause the receptor tyrosine kinase to form a polymer, which may result in autophosphorylation of specific tyrosine residues in the cytoplasmic domain. This may trigger a cascade of events through phosphorylation of intracellular proteins that ultimately transmit the extracellular signal to the nucleus, thereby causing transcription and synthesis of various genes that may be involved in cell growth, differentiation, proliferation and the like.

Among the various cytoplasmic kinases, RAF is one of the kinases that participate in the linear Ras-RAF-MEK-ERK mitogen-activated protein kinase (MAPK) pathway initiated by a receptor protein kinase, which is activated by a growth factor [Solit, D. B. et al., Nature, 439, (2006), 358]. Currently, there are known three types of isoforms thereof, i.e., A-RAF, B-RAF and C-RAF (RAF-1) [Jansen H W, et al., EMBO J, 2, (1983), 1969; Marais R. et al., Cancer Surv, 27, (1996), 101]. Since abnormal activation in the MAPK pathway has been observed in approximately 30% of human cancer tissues and gene mutation of B-RAF and C-RAF showing aberrant activation has been confirmed in cancer tissues, it is generally accepted that RAF plays a very important role in the MAPK pathway of cancer tissues.

Accordingly, there have been suggested methods of using a compound having an inhibitory effect against abnormal activities of RAF kinases for treatment of cancer. Hence, a number of RAF and modified RAF kinase inhibitors are currently under development or being tested in ongoing clinical studies. Examples of such RAF kinase inhibitors include: sorafenib (Nexavar®, Bayer) which is used for treatment of liver cancer, vemurafenib (PLX-4032, RG7204, Roche) which has been recently approved for treatment of melanoma; and examples that are currently being tested in clinical trials include: regorafenib and RDEA119 by Bayer, RAF265 by Novartis, E3810 by Advan Chem, DCC2036 by Deciphera Pharma., CKI-27 by Chugai Pharma., RO-5126766 by Roche, etc.

However, efficacy of such drugs has been questioned when they are administered over a duration of time despite their good initial performance as drug resistance has been observed in some patients about 7 months after the initial administration of the drug.

It has been postulated that such degradation may be due to the drug resistance of B-RAF inhibitor which is caused by abnormal activation of MAPK pathway due to changes in RAF, activation of complementary signaling system among different RAF isoforms, or activation of various receptor kinases other than MAPK as a result of activation of different pathways of Ras, a key protein used in the signal-transducing cascade which consists of K-Ras, N-Ras and H-Ras subtypes.

One of the signaling pathways that the RAF kinases do not get involved is C-FMS (cellular feline McDonough sarcoma), also known as colony-stimulating factor-1 receptor (CSF-1R), which is a member of the family of genes originally isolated from the Susan McDonough strain of feline sarcoma viruses. FMS is a receptor for macrophage-colony-stimulating factor (M-CSF) encoded by the C-FMS proto-oncogene, which belongs to a class III RTK along with Kit, Flt-3 and PDGFR. It has been reported that FMS tyrosine kinase is involved in cancer metastasis.

Another example is a receptor protein tyrosine kinase called discoidin domain receptor (DDR), which is a subfamily of receptor tyrosine kinases that possess an extracellular domain related to the lectin discoidin. In case of animals such as humans, there are two types of DDR proteins, DDR1 type and DDR2 type, which have similar amino acid sequences and are encoded by different genes from each other. It has been reported that DDR proteins may be implicated in the process of cancer growth and metastasis. In addition, an upregulated expression of DDR has been observed in some tumor cells, along with a report that an upregulated expression of DDR raised expression of MMP-1 and MMP-2 which are known to be implicated in cancer growth. Thus, it is expected that inhibition of such kinases can lead to a therapeutic effect against various types of cancer. Therefore, a compound having an inhibitory activity against not only RAF, but also FMS, DDR1 and DDR2 kinases can be more useful for treatment of various cancers including resistant cancer, as compared with a conventional RAF kinase inhibitor.

DISCLOSURE OF THE INVENTION

Problem to be Solved by the Invention

Accordingly, it is an object of the present invention to provide a compound and a pharmaceutical composition comprising same for prevention or treatment of intractable cancer such as resistant cancer by inhibiting not only RAF, which is a key regulator of cell growth, differentiation and proliferation, but also FMS, DDR1 and DDR2 kinases.

Means for Solving the Problem

In accordance with one aspect of the present invention, there is provided a thieno[3,2-d]pyrimidine derivative of formula (I) or a pharmaceutically acceptable salt thereof having inhibitory activity against RAF, FMS, DDR1 and DDR2 kinases:

(I)

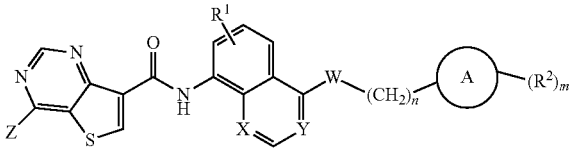

wherein,

A is hydrogen, $C_{1-6}$ alkyl, $C_{3-6}$ cycloalkyl, 3- to 6-membered heterocycloalkyl, $C_{6-10}$ aryl or 5- to 10-membered heteroaryl, wherein said aryl or heteroaryl is optionally reduced or substituted with hydrogen;

W is O, S, S(O), $S(O)_2$, NH, —NHNH— or 3- to 6-membered heterocycloalkyl;

X and Y are each independently CH or N;

Z is hydrogen, $C_{1-3}$ alkyl or $NR^3R^4$, wherein said $R^3$ and $R^4$ are each independently hydrogen, $C_{1-6}$ alkyl or —$(CH_2)$q-B—, B representing $NR^5R^6$, $C_{1-6}$ alkoxy, $C_{3-6}$ cycloalkyl or 3- to 6-membered heterocycloalkyl;

$R^1$ is hydrogen, halogen, $C_{1-3}$ alkyl or $C_{1-3}$ alkoxy, wherein said alkyl or alkoxy is unsubstituted or substituted with one or more halogen atoms;

$R^2$ is hydrogen, halogen, —$CF_3$, —$NO_2$, —OH, —CN, $C_{1-6}$ alkoxy, $C_{1-6}$ alkyl, $C_{2-4}$ alkenyl, $C_{2-4}$ alkynyl, —$NR^7R^8$, —$NHSO_2R^9$, —$SO_2R^{10}$, —$C(O)R^{11}$, —$NHC(O)R^{12}$, —$NHC(O)OR^{13}$, —$S(O)R^{14}$, $C_{3-6}$ cycloalkyl, 3- to 6-membered heterocycloalkyl, $C_{6-10}$ aryl, $C_{6-10}$ aryloxy, 5- to 10-membered heteroaryl or 5- to 10-membered heteroaryloxy, wherein said $R^2$ is connected to A by —$(CH_2)$p- or substituted with $C_{1-4}$ alkyl, [$C_{2-4}$alkyl] *$C_{2-4}$ alkylnyl*, $C_{1-4}$ alkylcarbonyl or one or more halogen atoms, $R^5$, $R^6$, $R^7$, $R^8$, $R^9$, $R^{10}$, $R^{11}$, $R^{12}$, $R^{13}$ and $R^{14}$ are each independently hydrogen, —$NH_2$, $C_{1-6}$ alkyl, $C_{1-6}$ alkoxy, $C_{3-6}$ cycloalkyl or 3- to 6-membered heterocycloalkyl, said alkyl, alkoxy, cycloalkyl or heterocycloalkyl being unsubstituted or substituted with one or more halogen atoms;

q is an integer ranging from 0 to 3;

p is an integer ranging from 0 to 3;

m is an integer ranging from 0 to 5;

n is an integer ranging from 0 to 2; and when A is hydrogen, m is 0.

In accordance with another aspect of the present invention, there is provided a pharmaceutical composition comprising a compound selected from the group consisting of a thieno[3,2-d]pyrimidine derivative of formula (I), a pharmaceutically acceptable salt, a stereoisomer, a hydrate and a solvate thereof as an active ingredient for prevention or treatment of diseases caused by abnormal activation of a protein kinase.

Effect of the Invention

The pharmaceutical composition comprising a compound selected from the group consisting of a thieno[3,2-d]pyrimidine derivative of formula (I), a pharmaceutically acceptable salt, a stereoisomer, a hydrate and a solvate thereof in accordance with the present invention is effective for prevention or treatment of abnormal cell growth diseases caused by abnormal activation of a protein kinase.

DETAILED DESCRIPTION OF THE INVENTION

The term 'halogen' as used herein refers to fluorine, chlorine, bromine or iodine, unless otherwise indicated.

The term 'alkyl' as used herein refers to a straight, [cyclic,] or branched hydrocarbon residue, unless otherwise indicated.

The term 'cycloalkyl' as used herein refers to a cyclic alkyl, e.g., cyclopropyl, unless otherwise indicated.

The term 'aryl' as used herein refers to a monocyclic or bicyclic aromatic group, e.g., phenyl and naphthyl, unless otherwise indicated.

The term 'heterocycloalkyl' as used herein refers to a cyclic alkyl, e.g., monocyclic or bicyclic alkyl, which contains one or more heteroatoms, preferably one to four heteroatoms, selected from O, N and S, unless otherwise indicated. Examples of monoheterocycloalkyl include piperidinyl, morpholinyl, thiamorpholinyl, pyrrolidinyl, imidazolidinyl, tetrahydrofuranyl, piperazinyl and similar groups thereof, but not limited thereto.

The term 'heteroaryl' as used herein refers to an aromatic group, e.g., monocyclic or bicyclic group, which contains one to four heteroatoms selected from O, N and S, and one or more of ring member carbon is substituted with C═O, unless otherwise indicated. Examples of monocyclic heteroaryl include thiazolyl, oxazolyl, thiophenyl, furanyl, pyrrolyl, imidazolyl, isooxazolyl, pyrazolyl, triazolyl, thiadiazolyl, tetrazolyl, oxadiazolyl, pyridinyl, pyridazinyl, pyrimidinyl, pyrazinyl and similar groups thereof, but not limited thereto. Examples of bicyclic heteroaryl include indolyl, benzothiophenyl, benzofuranyl, benzimidazolyl, benzoxazolyl, benzisoxazolyl, benzthiazolyl, benzthiadiazolyl, benztriazolyl, quinolinyl, isoquinolinyl, furinyl, furopyridinyl, oxochromene, dioxoisoindoline and similar groups thereof, but not limited thereto.

The compound of the present invention may also form a pharmaceutically acceptable salt. Such salt may be a pharmaceutically acceptable nontoxic acid addition salt containing anion, but not limited thereto. For example, the salt may include acid addition salts formed by inorganic acids such as hydrochloric acid, sulfuric acid, nitric acid, phosphoric acid, hydrobromic acid, hydriodic acid, and others; organic carbonic acids such as tartaric acid, formic acid, citric acid, acetic acid, trichloroacetic acid, trifluoroacetic acid, gluconic acid, benzoic acid, lactic acid, fumaric acid, maleic acid, and others; and sulfonic acids such as methanesulfonic acid, benzenesulfonic acid, p-toluenesulfonic acid, naphthalensulfonic acid, and others. Among them, acid addition salts formed by sulfuric acid, methanesulfonic acid or hydrohalogenic acid, and others are preferred.

Further, the compound of the present invention can have an asymmetric carbon center, and thus may be present in the form of R or S isomer, racemic compounds, diastereomeric mixture, or individual diastereomer, such entire isomers and mixtures being included within the scope of the present invention In addition, solvates and hydrates of the compound of formula (I) are encompassed within the scope of the present invention.

A preferred embodiment of the present invention is represented by the thieno[3,2-d]pyrimidine derivatives of formula (I), wherein:

A is aryl or heteroaryl;

W is NH;

Z is $NR^3R^4$;

X is CH; and

Y is N.

The preferred thieno[3,2-d]pyrimidine derivatives of the present invention are further exemplified below. In addition to the derivatives, pharmaceutically acceptable salts, isomers, hydrates or solvates thereof may also be used.

1) 4-amino-N-(1-((4-chlorophenyl)amino)-6-methylisoquinolin-5-yl)thieno[3,2-d]pyrimidine-7-carboxamide;
2) 4-amino-N-(6-methyl-1-((3-(trifluoromethyl)phenyl)amino)isoquinolin-5-yl)thieno[3,2-d]pyrimidine-7-carboxamide;
3) N-(1-((4-chlorophenyl)amino)-6-methylisoquinolin-5-yl)-4-(cyclopropylamino)thieno[3,2-d]pyrimidine-7-carboxamide;
4) 4-(cyclopropylamino)-N-(6-methyl-1-((3-(trifluoromethyl)phenyl)amino)isoquinolin-5-yl)thieno[3,2-d]pyrimidine-7-carboxamide;
5) 4-amino-N-(6-methyl-1-((3-(4-methyl-1H-imidazol-1-yl)-5-(trifluoromethyl)phenyl)amino)isoquinolin-5-yl)thieno[3,2-d]pyrimidine-7-carboxamide;
6) 4-(cyclopropylamino)-N-(6-methyl-1-((3-(4-methyl-1H-imidazol-1-yl)-5-(trifluoromethyl)phenyl)amino)isoquinolin-5-yl)thieno[3,2-d]pyrimidine-7-carboxamide;
7) 4-amino-N-(1-((4-((4-ethylpiperazin-1-yl)methyl)-3-(trifluoromethyl)phenyl)amino)-6-methylisoquinolin-5-yl)thieno[3,2-d]pyrimidine-7-carboxamide;
8) 4-(cyclopropylamino)-N-(1-((4-((4-ethylpiperazin-1-yl)methyl)-3-(trifluoromethyl)phenyl)amino)-6-methylisoquinolin-5-yl)thieno[3,2-d]pyrimidine-7-carboxamide;
9) N-(1-((4-((4-ethylpiperazin-1-yl)methyl)-3-(trifluoromethyl)phenyl)amino)-6-methylisoquinolin-5-yl)-4-(methylamino)thieno[3,2-d]pyrimidine-7-carboxamide;
10) 4-amino-N-(1-((4-(4-ethylpiperazin-1-yl)phenyl)amino)-6-methylisoquinolin-5-yl)thieno[3,2-d]pyrimidine-7-carboxamide;
11) 4-amino-N-(1-((4-((4-ethylpiperazin-1-yl)methyl)phenyl)amino)-6-methylisoquinolin-5-yl)thieno[3,2-d]pyrimidine-7-carboxamide;
12) 4-amino-N-(6-methyl-1-((3-(trifluoromethyl)phenyl)amino)isoquinolin-5-yl)thieno[3,2-d]pyrimidine-7-carboxamide;
13) 4-amino-N-(1-((4-chloro-3-(trifluoromethyl)phenyl)amino)-6-methylisoquinolin-5-yl)thieno[3,2-d]pyrimidine-7-carboxamide;
14) 4-amino-N-(1-((2-methoxy-5-(trifluoromethyl)phenyl)amino)-6-methylisoquinolin-5-yl)thieno[3,2-d]pyrimidine-7-carboxamide;
15) 4-amino-N-(6-methyl-1-((4-(trifluoromethyl)phenyl)amino)isoquinolin-5-yl)thieno[3,2-d]pyrimidine-7-carboxamide;
16) 4-amino-N-(1-((4-methoxyphenyl)amino)-6-methylisoquinolin-5-yl)thieno[3,2-d]pyrimidine-7-carboxamide;
17) 4-amino-N-(6-methyl-1-(p-tolylamino)isoquinolin-5-yl)thieno[3,2-d]pyrimidine-7-carboxamide;
18) 4-amino-N-(1-((4-isopropylphenyl)amino)-6-methylisoquinolin-5-yl)thieno[3,2-d]pyrimidine-7-carboxamide;
19) 4-amino-N-(1-((5-(t-butyl)isoxazol-3-yl)amino)-6-methylisoquinolin-5-yl)thieno[3,2-d]pyrimidine-7-carboxamide;
20) 4-amino-N-(1-((4-fluorophenyl)amino)-6-methylisoquinolin-5-yl)thieno[3,2-d]pyrimidine-7-carboxamide;
21) 4-amino-N-(6-methyl-1-(thiazol-2-ylamino)isoquinolin-5-yl)thieno[3,2-d]pyrimidine-7-carboxamide;
22) 4-amino-N-(1-((4-cyanophenyl)amino)-6-methylisoquinolin-5-yl)thieno[3,2-d]pyrimidine-7-carboxamide;
23) 4-amino-N-(6-methyl-1-(quinolin-5-ylamino)isoquinolin-5-yl)thieno[3,2-d]pyrimidine-7-carboxamide;
24) 4-amino-N-(1-((4-ethoxyphenyl)amino)-6-methylisoquinolin-5-yl)thieno[3,2-d]pyrimidine-7-carboxamide;
25) 4-amino-N-(6-methyl-1-((4-phenoxyphenyl)amino)isoquinolin-5-yl)thieno[3,2-d]pyrimidine-7-carboxamide;
26) 4-amino-N-(1-((4-hydroxyphenyl)amino)-6-methylisoquinolin-5-yl)thieno[3,2-d]pyrimidine-7-carboxamide;
27) 4-amino-N-(1-((4-isopropoxyphenyl)amino)-6-methylisoquinolin-5-yl)thieno[3,2-d]pyrimidine-7-carboxamide;
28) 4-amino-N-(1-((4-(dimethylamino)-6-methylisoquinolin-5-yl)thieno[3,2-d]pyrimidine-7-carboxamide;
29) 4-amino-N-(1-((2,3-dihydrobenzo[b][1,4]dioxin-6-yl)amino)-6-methylisoquinolin-5-yl)thieno[3,2-d]pyrimidine-7-carboxamide;
30) 4-amino-N-(1-((3,4-dimethoxyphenyl)amino)-6-methylisoquinolin-5-yl)thieno[3,2-d]pyrimidine-7-carboxamide;
31) 4-amino-N-(1-((3-fluoro-4-methoxyphenyl)amino)-6-methylisoquinolin-5-yl)thieno[3,2-d]pyrimidine-7-carboxamide;
32) 4-amino-N-(6-methyl-1-((3,4,5-trimethoxyphenyl)amino)isoquinolin-5-yl)thieno[3,2-d]pyrimidine-7-carboxamide;
33) 4-amino-N-(6-methylisoquinolin-5-yl)thieno[3,2-d]pyrimidine-7-carboxamide;
34) 4-amino-N-(1-(benzo[d][1,3]dioxol-5-ylamino)-6-methylisoquinolin-5-yl)thieno[3,2-d]pyrimidine-7-carboxamide;
35) 4-amino-N-(6-methyl-1-((5,6,7,8-tetrahydronaphthalen-2-yl)amino)isoquinolin-5-yl)thieno[3,2-d]pyrimidine-7-carboxamide;
36) 4-amino-N-(4-((4-chlorophenyl)amino)-7-methylquinazolin-8-yl)thieno[3,2-d]pyrimidine-7-carboxamide;
37) 4-(cyclopropylamino)-N-(1-((4-methoxyphenyl)amino)-6-methylisoquinolin-5-yl)thieno[3,2-d]pyrimidine-7-carboxamide;
38) 4-amino-N-(1-((3-chlorophenyl)amino)-6-methylisoquinolin-5-yl)thieno[3,2-d]pyrimidine-7-carboxamide;
39) 4-amino-N-(1-((3-bromophenyl)amino)-6-methylisoquinolin-5-yl)thieno[3,2-d]pyrimidine-7-carboxamide;

40) 4-amino-N-(1-((2,4-dichlorophenyl)amino)-6-methylisoquinolin-5-yl)thieno[3,2-d]pyrimidine-7-carboxamide;

41) 4-amino-N-(1-((3,4-dichlorophenyl)amino)-6-methylisoquinolin-5-yl)thieno[3,2-d]pyrimidine-7-carboxamide;

42) 4-amino-N-(1-((3,5-dichlorophenyl)amino)-6-methylisoquinolin-5-yl)thieno[3,2-d]pyrimidine-7-carboxamide;

43) 4-amino-N-(6-methyl-1-((3,4,5-trichlorophenyl)amino)isoquinolin-5-yl)thieno[3,2-d]pyrimidine-7-carboxamide;

44) 4-amino-N-(1-((4-chloro-3-methoxyphenyl)amino)-6-methylisoquinolin-5-yl)thieno[3,2-d]pyrimidine-7-carboxamide;

45) 4-amino-N-(1-benzylamino-6-methylisoquinolin-5-yl)thieno[3,2-d]pyrimidine-7-carboxamide;

46) 4-amino-N-(6-methyl-1-phenoxyisoquinolin-5-yl)thieno[3,2-d]pyrimidine-7-carboxamide;

47) 4-amino-N-(6-methyl-1-((4-morpholinophenyl)amino)isoquinolin-5-yl)thieno[3,2-d]pyrimidine-7-carboxamide;

48) N-(1-((4-(1H-pyrrol-1-yl)phenyl)amino)-6-methylisoquinolin-5-yl)-4-aminothieno[3,2-d]pyrimidine-7-carboxamide;

49) 4-amino-N-(6-methyl-1-(pyrimidin-4-ylamino)isoquinolin-5-yl)thieno[3,2-d]pyrimidine-7-carboxamide;

50) 4-amino-N-(1-((4-(difluoromethoxy)phenyl)amino)-6-methylisoquinolin-5-yl)thieno[3,2-d]pyrimidine-7-carboxamide;

51) 4-amino-N-(6-methyl-1-((4-(trifluoromethoxy)phenyl)amino)isoquinolin-5-yl)thieno[3,2-d]pyrimidine-7-carboxamide;

52) 4-amino-N-(1-((4-chlorophenyl)amino)isoquinolin-5-yl)thieno[3,2-d]pyrimidine-7-carboxamide;

53) 4-amino-N-(5-((4-chlorophenyl)amino)naphthalen-1-yl)thieno[3,2-d]pyrimidine-7-carboxamide;

54) 4-amino-N-(1-((4-ethynylphenyl)amino)-6-methylisoquinolin-5-yl)thieno[3,2-d]pyrimidine-7-carboxamide;

55) 4-amino-N-(1-(isopropylamino)-6-methylisoquinolin-5-yl)thieno[3,2-d]pyrimidine-7-carboxamide;

56) 4-amino-N-(1-(indolin-6-ylamino)-6-methylisoquinolin-5-yl)thieno[3,2-d]pyrimidine-7-carboxamide;

57) 4-amino-N-(1-((4-(fluoromethoxy)phenyl)amino)-6-methylisoquinolin-5-yl)thieno[3,2-d]pyrimidine-7-carboxamide;

58) N-(1-(4-chlorophenylamino)-6-methylisoquinolin-5-yl)thieno[3,2-d]pyrimidine-7-carboxamide;

59) 4-amino-N-(1-((4-chloro-3-((dimethylamino)methyl)phenyl)amino)-6-methylisoquinolin-5-yl)thieno[3,2-d]pyrimidine-7-carboxamide;

60) 4-amino-N-(1-((4-chloro-3-(pyrrolidin-1-ylmethyl)phenyl)amino)-6-methylisoquinolin-5-yl)thieno[3,2-d]pyrimidine-7-carboxamide;

61) 4-amino-N-(1-((4-chloro-3-((diethylamino)methyl)phenyl)amino)-6-methylisoquinolin-5-yl)thieno[3,2-d]pyrimidine-7-carboxamide;

62) 4-amino-N-(1-((1,4-diethyl-1,2,3,4-tetrahydroquinoxalin-6-yl)amino)-6-methylisoquinolin-5-yl)thieno[3,2-d]pyrimidine-7-carboxamide;

63) 4-amino-N-(1-((4-chloro-3-(piperidin-1-ylmethyl)phenyl)amino)-6-methylisoquinolin-5-yl)thieno[3,2-d]pyrimidine-7-carboxamide;

64) 4-amino-N-(1-((4-chloro-3-(morpholinomethyl)phenyl)amino)-6-methylisoquinolin-5-yl)thieno[3,2-d]pyrimidine-7-carboxamide;

65) 4-amino-N-(1-((4-chloro-3-((4-methylpiperazin-1-yl)methyl)phenyl)amino)-6-methylisoquinolin-5-yl)thieno[3,2-d]pyrimidine-7-carboxamide;

66) 4-amino-N-(1-((4-chloro-3-((diisopropylamino)methyl)phenyl)amino)-6-methylisoquinolin-5-yl)thieno[3,2-d]pyrimidine-7-carboxamide;

67) 4-amino-N-(6-methyl-1-((3-(methylsulfonamido)phenyl)amino)isoquinolin-5-yl)thieno[3,2-d]pyrimidine-7-carboxamide;

68) tert-butyl 4-(5-((5-(4-aminothieno[3,2-d]pyrimidine-7-carboxamido)-6-methylisoquinolin-1-yl)amino)-2-chlorobenzyl)piperazine-1-carboxylate;

69) 4-amino-N-(1-((4-chloro-3-(piperazin-1-ylmethyl)phenyl)amino)-6-methylisoquinolin-5-yl)thieno[3,2-d]pyrimidine-7-carboxamide;

70) 4-amino-N-(1-((3-chloro-4-methoxyphenyl)amino)-6-methylisoquinolin-5-yl)thieno[3,2-d]pyrimidine-7-carboxamide;

71) 4-amino-N-(1-((3-(dimethylcarbamoyl)phenyl)amino)-6-methylisoquinolin-5-yl)thieno[3,2-d]pyrimidine-7-carboxamide;

72) 4-amino-N-(6-methyl-1-((3-(methylcarbamoyl)phenyl)amino)isoquinolin-5-yl)thieno[3,2-d]pyrimidine-7-carboxamide;

73) 4-amino-N-(1-((4-chloro-2-fluorophenyl)amino)-6-methylisoquinolin-5-yl)thieno[3,2-d]pyrimidine-7-carboxamide;

74) 4-amino-N-(1-((4-bromo-2-fluorophenyl)amino)-6-methylisoquinolin-5-yl)thieno[3,2-d]pyrimidine-7-carboxamide;

75) 4-amino-N-(1-((4-methoxybenzyl)amino)-6-methylisoquinolin-5-yl)thieno[3,2-d]pyrimidine-7-carboxamide;

76) 4-amino-N-(1-((4-chlorobenzyl)amino)-6-methylisoquinolin-5-yl)thieno[3,2-d]pyrimidine-7-carboxamide;

77) 4-amino-N-(1-(2-(4-chlorophenyl)hydrazinyl)-6-methylisoquinolin-5-yl)thieno[3,2-d]pyrimidine-7-carboxamide;

78) 4-amino-N-(1-((3-((dimethylamino)methyl)phenyl)amino)-6-methylisoquinolin-5-yl)thieno[3,2-d]pyrimidine-7-carboxamide;

79) 4-amino-N-(6-methyl-1-((4-oxo-4H-chromen-6-yl)amino)isoquinolin-5-yl)thieno[3,2-d]pyrimidine-7-carboxamide;

80) N-(1-((3-acetylphenyl)amino)-6-methylisoquinolin-5-yl)-4-aminothieno[3,2-d]pyrimidine-7-carboxamide;

81) 4-amino-N-(1-((4-(2-methoxyethoxy)phenyl)amino)-6-methylisoquinolin-5-yl)thieno[3,2-d]pyrimidine-7-carboxamide;

82) 4-amino-N-(6-methyl-1-((3-(trifluoromethoxy)phenyl)amino)isoquinolin-5-yl)thieno[3,2-d]pyrimidine-7-carboxamide;

83) N-(1-((4-acetylphenyl)amino)-6-methylisoquinolin-5-yl)-4-aminothieno[3,2-d]pyrimidine-7-carboxamide;

84) 4-amino-N-(6-methyl-1-((4-methylsulfonamido)phenyl)amino)isoquinolin-5-yl)thieno[3,2-d]pyrimidine-7-carboxamide;

85) 4-amino-N-(6-methyl-1-((3-(methylsulfonyl)phenyl)amino)isoquinolin-5-yl)thieno[3,2-d]pyrimidine-7-carboxamide;

86) 4-amino-N-(1-((4-chloro-3-(methoxymethyl)phenyl)amino)-6-methylisoquinolin-5-yl)thieno[3,2-d]pyrimidine-7-carboxamide;

87) 4-amino-N-(1-((4-methoxy-3-(methylsulfonamido)phenyl)amino)-6-methylisoquinolin-5-yl)thieno[3,2-d]pyrimidine-7-carboxamide;

88) 4-amino-N-(1-((4-chloro-3-(methylsulfonamido)phenyl)amino)-6-methylisoquinolin-5-yl)thieno[3,2-d]pyrimidine-7-carboxamide;

89) 4-amino-N-(1-((6-chloropyridin-3-yl)amino)-6-methylisoquinolin-5-yl)thieno[3,2-d]pyrimidine-7-carboxamide;

90) 4-amino-N-(1-((2-chloropyridin-4-yl)amino)-6-methylisoquinolin-5-yl)thieno[3,2-d]pyrimidine-7-carboxamide;

91) 4-amino-N-(6-methyl(4-(methylsulfonamidomethyl)phenyl)amino)isoquinolin-5-yl)thieno[3,2-d]pyrimidine-7-carboxamide;

92) 4-amino-N-(6-methyl-1-((3-(methylsulfonamidomethyl)phenyl)amino)isoquinolin-5-yl)thieno[3,2-d]pyrimidine-7-carboxamide;

93) 4-amino-N-(1-((4-chloro-3-fluorophenyl)amino)-6-methylisoquinolin-5-yl)thieno[3,2-d]pyrimidine-7-carboxamide;

94) 4-amino-N-(1-((3-bromo-4-chlorophenyl)amino)-6-methylisoquinolin-5-yl)thieno[3,2-d]pyrimidine-7-carboxamide;

95) 4-amino-N-(1-((4-(dimethylcarbamoyl)phenyl)amino)-6-methylisoquinolin-5-yl)thieno[3,2-d]pyrimidine-7-carboxamide;

96) N-(1-((3-acetamidophenyl)amino)-6-methylisoquinolin-5-yl)-4-aminothieno[3,2-d]pyrimidine-7-carboxamide;

97) 4-amino-N-(6-methyl-1-((1-methyl-1H-indazol-6-yl)amino)isoquinolin-5-yl)thieno[3,2-d]pyrimidine-7-carboxamide;

98) 4-amino-N-(6-methyl-1-((4-(methylsulfinyl)phenyl)amino)isoquinolin-5-yl)thieno[3,2-d]pyrimidine-7-carboxamide;

99) 4-amino-N-(6-methyl-1-((2-methyl-1,3-dioxoisoindolin-5-yl)amino)isoquinolin-5-yl)thieno[3,2-d]pyrimidine-7-carboxamide;

100) 4-amino-N-(1-((6-methoxypyridin-3-yl)amino)-6-methylisoquinolin-5-yl)thieno[3,2-d]pyrimidine-7-carboxamide;

101) 4-amino-N-(6-methyl-1-((3-(2,2,2-trifluoroacetyl)phenyl)amino)isoquinolin-5-yl)thieno[3,2-d]pyrimidine-7-carboxamide;

102) 4-amino-N-(6-methyl-1-((4-propionylphenyl)amino)isoquinolin-5-yl)thieno[3,2-d]pyrimidine-7-carboxamide;

103) 4-amino-N-(1-((4-hexanoylphenyl)amino)-6-methylisoquinolin-yl)thieno[3,2-d]pyrimidine-7-carboxamide;

104) N-(1-((1-acetyl-1H-indazol-6-yl)amino)-6-methylisoquinolin-5-yl)-4-aminothieno[3,2-d]pyrimidine-7-carboxamide;

105) 4-amino-N-(1-((3-chloro-4-fluorophenyl)amino)-6-methylisoquinolin-5-yl)thieno[3,2-d]pyrimidine-7-carboxamide;

106) 4-amino-N-(6-methyl-1-((5-oxo-5,6,7,8-tetrahydronaphthalen-2-yl)amino)isoquinolin-5-yl)thieno[3,2-d]pyrimidine-7-carboxamide;

107) 4-amino-N-(6-methyl-1-((2-methyl-2H-indazol-6-yl)amino)isoquinolin-5-yl)thieno[3,2-d]pyrimidine-7-carboxamide;

108) methyl 4-((5-(4-aminothieno[3,2-d]pyrimidine-7-carboxamido)-6-methylisoquinolin-1-yl)amino)benzoate;

109) 4-amino-N-(6-methyl-1-((1-methyl-1H-indazol-5-yl)amino)isoquinolin-5-yl)thieno[3,2-d]pyrimidine-7-carboxamide;

110) 4-amino-N-(6-methyl-1-((2-methyl-2H-indazol-5-yl)amino)isoquinolin-5-yl)thieno[3,2-d]pyrimidine-7-carboxamide;

111) 4-amino-N-(6-methyl-1-((6-methylpyridin-3-yl)amino)isoquinolin-5-yl)thieno[3,2-d]pyrimidine-7-carboxamide;

112) 4-amino-N-(6-methyl-1-((1-methyl-1H-indol-6-yl)amino)isoquinolin-5-yl)thieno[3,2-d]pyrimidine-7-carboxamide;

113) tert-butyl 6-((5-(4-aminothieno[3,2-d]pyrimidine-7-carboxamido)-6-methylisoquinolin-1-yl)amino)-1H-indazol-1-carboxylate;

114) N-(1-((1H-indazol-6-yl)amino)-6-methylisoquinolin-5-yl)-4-aminothieno[3,2-d]pyrimidine-7-carboxamide hydrochloride;

115) 4-amino-N-(1-((5-chloro-2-fluorophenyl)amino)-6-methylisoquinolin-5-yl)thieno[3,2-d]pyrimidine-7-carboxamide;

116) 4-amino-N-(1-((3-chloro-2-fluorophenyl)amino)-6-methylisoquinolin-5-yl)thieno[3,2-d]pyrimidine-7-carboxamide;

117) 4-amino-N-(1-((3-fluoro-4-(4-methylpiperazin-1-yl)phenyl)amino)-6-methylisoquinolin-5-yl)thieno[3,2-d]pyrimidine-7-carboxamide;

118) 4-amino-N-(1-((3-chloro-1-methyl-1H-indazol-6-yl)amino)-6-methylisoquinolin-5-yl)thieno[3,2-d]pyrimidine-7-carboxamide;

119) 4-amino-N-(6-methyl-1-((4-(prop-2-yn-1-yloxy)phenyl)amino)isoquinolin-5-yl)thieno[3,2-d]pyrimidine-7-carboxamide;

120) 4-amino-N-(1-((2-methoxy-4-morpholinophenyl)amino)-6-methylisoquinolin-5-yl)thieno[3,2-d]pyrimidine-7-carboxamide;

121) 4-amino-N-(1-(benzo[d]thiazol-6-ylamino)-6-methylisoquinolin-5-yl)thieno[3,2-d]pyrimidine-7-carboxamide;

122) N-(1-((1H-indazol-5-yl)amino)-6-methylisoquinolin-5-yl)-4-aminothieno[3,2-d]pyrimidine-7-carboxamide;

123) 4-amino-N-(1-((3-chloro-2,4-difluorophenyl)amino)-6-methylisoquinolin-5-yl)thieno[3,2-d]pyrimidine-7-carboxamide;

124) 4-amino-N-(1-((3-(dimethylamino)propyl)amino)-6-methylisoquinolin-5-yl)thieno[3,2-d]pyrimidine-7-carboxamide; and 125) 4-amino-N-(6-methyl-1-(piperidin-1-yl)isoquinolin-5-yl)thieno[3,2-d]pyrimidine-7-carboxamide.

The derivatives of the present invention may be obtained via Reaction Scheme 3 by using intermediates obtained in Reaction Scheme 1 and Reaction Scheme 2 shown below, or intermediates which are commercially available, respectively. Further, mass analysis of the obtained thieno[3,2-d]pyrimidine derivatives may be performed by using Micro-Mass ZQ™ (Waters.)

The pharmaceutical composition comprising, as an active ingredient, the thieno[3,2-d]pyrimidine derivatives or salts, isomers, hydrates or solvates thereof may be used for prevention or treatment of abnormal cell growth diseases caused by abnormal activation of a protein kinase.

Examples of the protein kinase include ALK, AMPK, Aurora A, Aurora B, Aurora C, Axl, Blk, Bmx, BTK, CaMK, CDK2/cyclinE, CDK5/p25, CHK1, CK2, c-RAF, DDR1, DDR2, DMPK, EGFR1, Her2, Her4, EphA1, EphB1, FAK, FGFR2, FGFR3, FGFR4, Flt-1, Flt-3, Flt-4, Fms (CSF-1), Fyn, GSK3beta, HIPK1, IKKbeta, IGFR-1R, IR, Itk, JAK2, JAK3, KDR, Kit, Lck, Lyn, MAPK1, MAPKAP-K2, MEK1, Met, MKK6, MLCK, NEK2, p70S6K, PAK2, PDGFR alpha, PDGFR beta, PDK1, Pim-1, PKA, PKBalpha, PKCalpha, Plk1, Ret, ROCK-I, Rsk1, SAPK2a, SGK, Src, Syk, Tie-2, Tec, Trk or ZAP-70. The pharmaceutical composition in accordance with the present invention has good inhibitory activity against the above kinases.

Examples of the abnormal cell growth diseases caused by abnormal activation of protein kinase in which the inventive pharmaceutical composition is effective against include gastric cancer, lung cancer, liver cancer, colorectal cancer, small intestine cancer, pancreatic cancer, brain cancer, bone cancer, melanoma, breast cancer, sclerosing adenosis, uterine cancer, cervical cancer, head and neck cancer, esophagus cancer, thyroid cancer, parathyroid cancer, renal cancer, sarcoma, prostate cancer, urethral cancer, bladder cancer, blood cancer, lymphoma, fibroadenoma, inflammation, diabetes, obesity, psoriasis, rheumatoid arthritis, hemangioma, acute or chronic kidney disease, coronary restenosis, autoimmune diseases, asthma, neurodegenerative diseases, acute infection or ocular diseases caused by angiogenesis.

The inventive pharmaceutical composition may comprise pharmaceutically acceptable carriers, excipients or additives. The pharmaceutical composition may comprise a drug selected from the group consisting of cell signal transduction inhibitors, mitosis inhibitors, alkylating agents, antimetabolites, antibiotics, growth factor inhibitors, cell cycle inhibitors, topoisomerase inhibitors, biological reaction modifiers, antihormonal agents, antiandrogen, cell differentiation/proliferation/survival inhibitors, apoptosis inhibitors, inflammation inhibitors and P-glycoprotein inhibitors. In case where the inventive pharmaceutical composition is developed into a formulation, it may be used in combination with said drug or developed into a combined formulation.

The inventive pharmaceutical composition may comprise conventional pharmaceutically acceptable carriers, excipients or additives. The pharmaceutical composition may be formulated in accordance with conventional methods, and may be prepared in the form of oral formulations such as a tablet, pill, powder, capsule, syrup, an emulsion, a microemulsion and others or parenteral formulations such as intramuscular, intravenous or subcutaneous administration.

For oral formulations, additives or carriers such as cellulose, calcium silicate, corn starch, lactose, sucrose, dextrose, calcium phosphate, stearic acid, magnesium stearate, calcium stearate, gelatin, talc, surfactants, suspending agents, emulsifying agents, diluting agents and others. For injectable formulations, additives or carriers such as water, saline, glucose solution, glucose solution analogs, alcohols, glycols, ethers (e.g., polyethylene glycol 400), oils, fatty acids, fatty acid esters, glycerides, surfactants, suspending agents, emulsifying agents and others may be used.

Hereinafter, an exemplary method for preparing the compound of the present invention is explained.

The following abbreviations are used in Preparation Examples, Preparation Methods and Examples below:

DECP: diethyl chlorophosphate
DIPEA: N,N-diisopropylethylamine
HATU: [2-(1H-9-azabenzotriazol-1-yl) 1,1,3,3-tetramethyl uranium hexafluorophosphate]
HOBT: N-hydroxybenzotriazole
DMF: N,N-dimethyl formamide
DMSO: dimethyl sulfoxide
$CH_2Cl_2$: dichloromethane
$Na_2SO_4$: anhydrous sodium sulfate
$NaBH(OAc)_3$: sodium triacetoxyborohydride
$Cs_2CO_3$: cesium carbonate
AIBN: azobisisobutyronitrile
$Pd_2(dba)_3$: tris(dibenzylideneacetone)dipalladium(0)
EA: ethyl acetate
EtOAc: ethylacetate
NaOH: sodium hydroxide
THF: tetrahydrofuran The compound of formula (I) in accordance with the present invention may be prepared via Reaction Scheme 3 by using intermediates obtained in Preparation Examples 1 and 2 as shown in Reaction Schemes 1 and 2, respectively.

Reaction Scheme 1

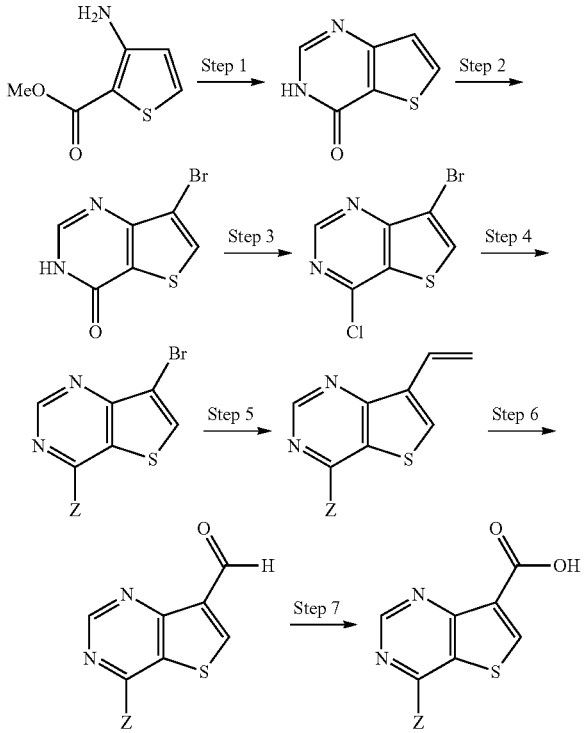

wherein Z is the same as defined in formula (I).

The above reaction processes are exemplified in the following stepwise reactions.

Step 1-1

Anhydrous acetic acid (12 to 13 equivalents) and formic acid (12 to 15 L/mol, based on a standard equivalent unit) are mixed. Methyl-3-aminothiophene-4-carboxylate (1.0 equivalent, standard equivalent unit) is added to the resulting reaction solution, and stirred for about 2 to 4 hours at room temperature. The reaction solution is removed under reduced pressure. Separately, ammonium formate (8/0 to 9/0 equivalents) and formamide (150 mL, 3.76 mol) are added, and the mixture is stirred for about 20 to 40 minutes. The synthesized material is added to the resulting reaction mixture, and stirred for about 7 to 9 hours at a temperature in the range of 140 to 160° C. The reaction mixture is cooled to room temperature and further stirred for about 11 to 13 hours. The resulting solid is filtered and washed with water to obtain the desired compound.

Step 1-2

The compound (1.0 equivalent, standard equivalent unit) obtained in <Step 1-1> is dissolved in acetic acid (9.0 to 11.0 equivalents). Separately, bromine (3.0 to 4.0 equivalents) is diluted in acetic acid (9.0 to 11.0 equivalents) and resulting solution is slowly added to the solution prepared. The reaction solution is placed in a sealed reactor and stirred for 17 to 19 hours at a temperature in the range of 110 to 130° C. The reaction mixture is cooled to room temperature, and acetic acid is removed under reduced pressure. An ice water is poured to the mixture, and the resulting solid compound is filtered, followed by drying. The desired compound is obtained without further purification.

Step 1-3

Dimethylformamide (2.0 to 3.0 equivalents) and dichloromethane (3.0 to 4.0 L/mol, based on a standard equivalent unit) are added to a reactor. Separately, oxalyl chloride (3.0 to 4.0 L/mol, based on a standard equivalent unit) is diluted in dichloromethane (3.0 to 4.0 L/mol, based on a standard equivalent unit) and resulting solution is added to the solution prepared over a period of about 20 to 40 minutes. The compound (1.0 equivalent, standard equivalent unit 35 g, 0.15 mol) obtained in <Step 1-2> is added thereto, heated, and refluxed for 2.5 to 4.0 hours. The temperature is lowered and water is slowly added. The resulting organic layer is separated and aqueous layer is subjected to extraction using dichloromethane. The resulting organic layer is dried over anhydrous sodium sulfate. The dried organic layer is filtered and distilled under reduced pressure, and dried under nitrogen atmosphere to obtain the desired compound.

Step 1-4

The compound (1.0 equivalent, standard equivalent unit) obtained in <Step 1-3> and 2.0 M ammonia (15 to 25 mL/g, based on the standard equivalent unit) are dissolved in a 2-propanol solvent, sealed in a container, and stirred. The external temperature is raised to a range of 95 to 100° C., followed by stirring for 7 hours. The reaction mixture was cooled to room temperature, and the solvent is distilled under reduced pressure. Distilled water (40 to 55 mL/g, based on the standard equivalent unit) is added to the concentrate, followed by stirring for 20 to 40 minutes. The resulting solid is filtered, and washed with distilled water (15 to 25 mL/g, based on the standard equivalent unit) twice. The compound is dried in an oven at 45 to 55° C. to obtain the desired compound.

Step 1-5

The compound (1.0 equivalent, standard equivalent unit) obtained in <Step 1-4>, tetrakis(triphenylphosphine)palladium (0.05 to 0.08 equivalents) and copper iodide (1.0 to 1.2 equivalents) are dissolved in 1.4-dioxane (1.5 to 2.5 L/mol, based on the standard equivalent unit) solvent and stirred. Tributyl(vinyl)tin (1.1 to 1.5 equivalents) is slowly added to the resulting reaction solution and refluxed for 6 hours or more, preferably about 6 to 8 hours. The reaction solution is cooled to room temperature, and potassium fluoride aqueous solution (3.0 to 4.0 L/mol, based on the standard equivalent unit) and ethylacetate (3.0 to 4.0 L/mol, based on the standard equivalent unit) are added thereto, followed by intense stirring for 2.5 hours or more, preferably about 2.5 to 3.5 hours. The reaction solution is filtered through a Celite pad under reduced pressure, washed with ethyl acetate (0.5 to 0.8 L/mol, based on the standard equivalent unit). The organic layer of the filtrate is separated and dried over anhydrous sodium sulfate. The dried organic layer is filtered and distilled under reduced pressure, added with a mixed solution of ethylacetate/hexane=1/1 (v/v) (0.8 to 1.2 L/mol, based on the standard equivalent unit), followed by stirring for 1 hour. The resulting reaction solution is filtered under reduced pressure, and washed with a mixed solution of ethylacetate/hexane=1/1 (v/v) (0.4 to 0.6 L/mol, based on the standard equivalent unit). The resulting solid is dried with warm wind in an oven (45 to 55° C.) for 2.5 hour or more, preferably about 2.5 to 3.5 hours, to obtain the desired compound.

Step 1-6

The compound (1.0 equivalent, standard equivalent unit) obtained in <Step 1-5> is stirred with a mixed solution of chloroform (0.8 to 1.2 L/mol, based on the standard equivalent unit) and methanol (0.8 to 1.2 L/mol, based on the standard equivalent unit). The resulting reaction solution is cooled to −65 to −78° C. as nitrogen gas is introduced, followed by supplying ozone gas for 2.5 hours or more, preferably about 2.5 to 3.5 hours. The ozone generator is removed and the reaction solution is raised to room temperature while nitrogen gas is introduced, dimethyl sulfide (0.2 to 0.4 L/mol, based on the standard equivalent unit) is added thereto, followed by stirring for 2.5 hours or more, preferably about 2.5 to 3.5 hours, at room temperature. The reaction solution is concentrated under reduced pressure, and ethyl acetate (0.3 to 0.5 L/mol, based on the standard equivalent unit) is added to the concentrate, followed by stirring for 1.0 to 1.5 hours. The resulting solution is filtered under reduced pressure, and filtered solid is washed wish ethyl acetate (0.04 to 0.06 L/mol, based on the standard equivalent unit). The filtered solid dried with warm wind in an oven (45 to 55° C.) for 2.5 hours or more, preferably about 2.5 to 3.5 hours, to obtain the desired compound.

Step 1-7

Disodium hydrogen phosphate (48.2 g, 0.402 mol) is dissolved in distilled water (180 mL), and the reaction solution is cooled to 5° C. or below, preferably about 5 to −3° C. The compound (1.0 equivalent, standard equivalent unit) obtained in <Step 1-6> is dissolved in a mixed solution of acetone (0.8 to 1.2 L/mol, based on the standard equivalent unit) and dimethyl sulfoxide (0.8 to 1.2 L/mol), followed by slowly adding the resulting solution to the reaction solution prepared at 5° C. or below, preferably in the temperature range of about 5.0 to 3.0° C. Separately, sodium chlorite (1.0 to 1.3 equivalents) is dissolved in distilled water (0.8 to 1.2 L/mol, based on the standard equivalent unit), followed by slowly adding the resulting solution to the reaction solution prepared at 5° C. or below, preferably in the temperature range of about 5.0 to 1.0° C. The reaction solution is raised to room temperature, followed by stirring for 2.5 or more, preferably about 2.5 to 3.5 hours. Distilled water (8.0 to 12 L/mol, based on the standard equivalent unit) is added thereto, followed by further stirring for 4.5 hours or more, preferably about 4.5 to 5.5 hours. The reaction solution was filtered under reduced pressure, and the resulting solid is washed with diethyl ether (0.3 to 0.5 L/mol). Ethanol (0.8 to 1.2 L/mol, based on the standard equivalent unit) is added to the filtered solid, and the solution is distilled under reduced pressure, dried with warm wind in an oven (45 to 55° C.) for 2.5 hours or more, preferably about 2.5 to 3.5 hours, to obtain the desired compound.

Reaction Scheme 2

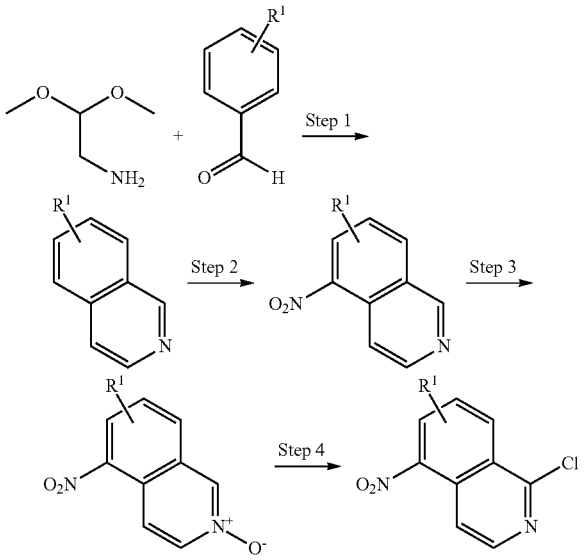

Reaction Scheme 2 illustrates a reaction process when X═CH and Y═N in the compound of formula (I), wherein $R^1$ is same as defined in formula (I).

The above reaction processes are exemplified in the following stepwise reactions.

Step 2-1

Aldehyde (1.0 equivalent, standard equivalent unit) substituted with $R^3$ is stirred in a solvent of chloroform (1.6 to 2.0 L/mol, based on the standard equivalent unit), and aminoacetaldehyde dimethyl acetal (1.0 to 1.2 equivalents) is slowly added thereto, followed by stirring at 80 to 95° C. until about one-half of the reaction solution is evaporated. The reaction solution is cooled to room temperature, and the resulting yellow reaction solution is dissolved in chloroform (0.8 to 1.0 L/mol, based on the standard equivalent unit), followed by cooling the reaction solution to 5° C. or below, preferably about 5 to 0° C. Ethyl chloroformate (1.0 to 1.2 equivalents) and triethylphosphite (1.2 to 1.4 equivalents) are slowly added to the reaction solution for 0.5 to 1.0 hour. The resulting reaction solution is stirred for 20 to 28 hours at room temperature. Subsequently, the reaction solution is cooled to 5° C. or below, preferably about 5 to 0° C., and then titanium tetrachloride (3.8 to 4.2 equivalents) is slowly added thereto for 0.5 to 1.0 hour, and refluxed for 10 hours or more, preferably about 10 to 14 hours. The reaction solution is cooled to room temperature, followed by stirring for 10 hours or more, preferably, 10 to 14 hours. An ice water is poured to the reaction mixture to separate the organic layer and aqueous layer, and the aqueous layer is washed with dichloromethane. The aqueous layer is poured into a saturated sodium potassium tartrate solution and adjusted to pH 8.0 to 9.5 by adding ammonia solution, and subjected to extraction with $CH_2Cl_2$. The obtained organic layers are dried over anhydrous sodium sulfate, and concentrated under reduced pressure to obtain the desired compound.

Step 2-2

Sulfuric acid (300 to 400 L/mol, based on the standard equivalent unit) is added to the compound (1.0 equivalent, standard equivalent unit) obtained in <Step 2-1> and stirred. The reaction solution is cooled to 5° C. or below, preferably about 5 to 0° C., followed by slowly adding potassium nitrate (2.0 to 2.2 equivalents). The reaction solution is stirred for 3 hours or more, preferably about 3 to 4 hours, at a temperature of 5 to 0° C. The reaction mixture poured into an ice water and adjusted to pH 11 to 12 by adding 5 N NaOH solution, followed by stirring for 11 hours or more, preferably about 11 to 13 hours, at room temperature. The generated solid is filtered under reduced pressure, followed by washing with water. The filtered solid is dried with warm wind in an oven (35 to 45° C.) for 3 hours or more, preferably about 3 to 4 hours to obtain the desired compound.

Step 2-3

The compound (1.0 equivalent, standard equivalent unit) obtained in <Step 2-2> is dissolved in $CH_2Cl_2$ (2.8 to 3.3 L/mol, based on the standard equivalent unit), and the reaction solution is cooled to 5° C. or below, preferably about 5 to 0° C. Subsequently, mCPBA (1.5 to 1.7 equivalents) is slowly added to the reaction solution for 0.5 to 1 hour, followed by stirring for 10 hours or more, preferably about 10 to 11 hours at a temperature of 5 to 0° C. The reaction mixture is adjusted to pH of 10 to 11 by adding 1 N NaOH solution, and subjected to extraction with $CH_2Cl_2$. The obtained organic layers are dried over anhydrous sodium sulfate, and concentrated under reduced pressure to obtain the desired compound.

Step 2-4

The compound (1.0 equivalent, standard equivalent unit) obtained in <Step 2-3> is dissolved in 1,2-dichloroethane (8 to 9 L/mol, based on the standard equivalent unit), and $POCl_3$ (4.5 to 5.5 equivalents) is added to the reaction solution at room temperature. And then, the reaction solution is refluxed for 6 hours or more, preferably about 6 to 7 hours. The reaction solution is cooled to room temperature, and concentrated by distilling the solvent under reduced pressure. The concentrated solid is dissolved in dichloromethane. An ice water is added thereto, and the mixed solution is subjected to extraction with dichloromethane. The obtained organic layer is dried over anhydrous sodium sulfate, and concentrated under reduced pressure. A mixed solution of ethyl acetate/hexane=1/1 (v/v) is added to the concentrated solid, followed by stirring for 2 hours or more, preferably about 2 to 2.5 hours at room temperature. The resulting solid is filtered under reduced pressure, and washed with a mixed solution of ethyl acetate/hexane=1/1 (v/v). The filtered solid is dried with warm wind in an oven (35 to 45° C.) for 3 hours or more, preferably about 3 to 4 hours to obtain the desired compound.

Reaction Scheme 3

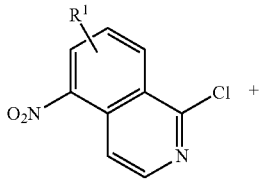

-continued

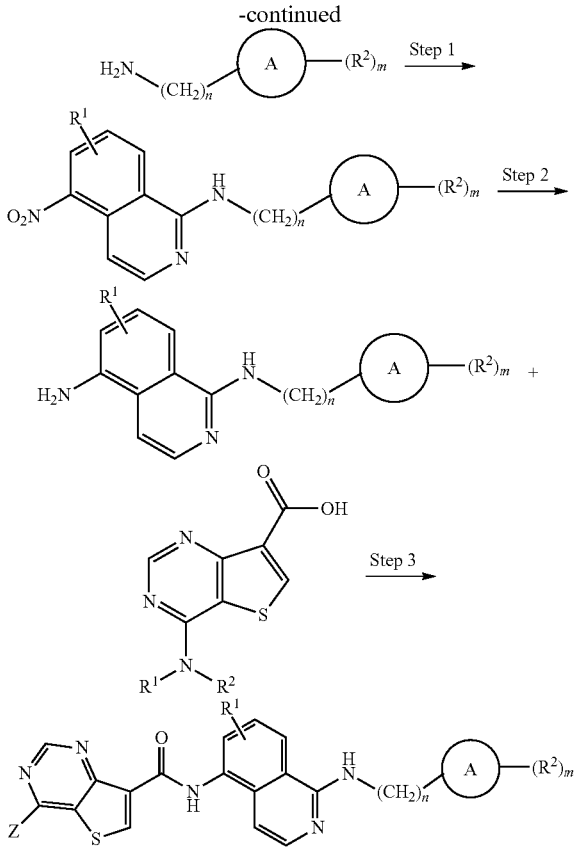

Reaction Scheme 3 illustrates a reaction process when W is NH in the compound of formula (I), wherein A, $R^1$, $R^2$, n and m are same as defined in formula (I).

The above reaction processes are exemplified in the following stepwise reactions.

Step 3-1

The compound (1.0 equivalent, standard equivalent unit) obtained in <Step 2-4> is dissolved in 2-propanol (2.0 to 4.0 L/mol, based on the standard equivalent unit), and amine containing ring A (0.6 to 0.9 equivalents) is added to the reaction solution at room temperature. The reaction solution is sealed, and stirred for 9 hours or more, preferably about 9 to 11 hours, at a temperature of 85 to 95° C. The reaction mixture is cooled to room temperature, and the generated solid is filtered under reduced pressure, followed by washing with ethyl acetate. The filtered solid is dried with warm wind in an oven (45 to 55° C.) for 2.5 hours or more, preferably about 2.5 to 3.5 hours to obtain the desired compound.

Step 3-2

Iron (3.0 to 5.0 equivalents) and concentrated hydrochloric acid (0.04 to 0.06 mL/mmol) are added to a mixed solution of ethanol/water=1/1 (v/v) (3.0 to 5.0 L/mol, based on the standard equivalent unit), and refluxed for 0.5 to 1.5 hours. The compound (1.0 equivalent, standard equivalent unit) obtained in <Step 3-1> is added to a reaction mixture, and refluxed for 1.5 hours or more, preferably about 1.5 to 2.5 hours. The reaction mixture is filtered through a Celite pad under reduced pressure, and washed with a mixed solution of chloroform/2-propanol=4/1 (v/v). The filtrate obtained was distilled under reduced pressure, and dissolved in a mixed solution of chloroform/2-propanol=4/1 (v/v). The organic layer is washed with an aqueous solution of sodium bicarbonate and brine. The obtained organic layer is dried over anhydrous sodium sulfate, filtered, and concentrated under reduced pressure to obtain the desired compound.

Step 3-3

The compound (1.0 equivalent, standard equivalent unit) obtained in <Step 1-7> is dissolved in dimethylformamide (1.0 to 3.0 L/mol, based on the standard equivalent unit), and DECP (1.8 to 2.2 equivalents) and DIPEA (3.6 to 4.4 equivalents) are added to the reaction solution at a temperature of 4 to −4° C. The reaction solution is stirred for 5 to 15 minutes. The compound (0.45 to 0.55 equivalent) obtained in <Step 3-2> is added to the reaction mixture, and the mixture is stirred for 11 hours or more, preferably about 11 to 13 hours. The reaction mixture is diluted with ethyl acetate, and washed with a saturated aqueous solution of sodium bicarbonate and brine. The organic layer is dried over anhydrous sodium sulfate, filtered, and concentrated under reduced pressure. Ethyl acetate is added to the concentrated solid, followed by stirring for 1.5 hours or more, preferably about 1.5 to 2.5 hours. The resulting solid is filtered under reduced pressure, and washed with ethyl acetate and methanol. The filtered solid is dried with warm wind in an oven (35 to 45° C.) for 2.5 hours or more, preferably about 2.5 to 3.5 hours to obtain the desired compound.

The synthesis of derivatives of the present invention may be performed by employing a general reaction scheme such as Reaction Schemes 1, 2 and 3 shown above, and mass analysis may be performed by using MicroMass ZQ™ (Waters).

The present invention provides a pharmaceutical composition comprising the compound of formula (I) or a pharmaceutically acceptable salt thereof as an active ingredient to prevent or treat abnormal cell growth diseases caused by overactivity (abnormal activation) of a protein kinase.

A dosage of the compound of formula (I) or pharmaceutically acceptable salt thereof may be determined in light of various relevant factors including the condition, age, body weight and sex of the subject to be treated, administration route and disease severity. For example, the compound of formula (I) may be administered in a range of 0.01 to 200 mg/kg (body weight), preferably 10 to 100 mg/kg (body weight) once or twice a day orally or parenterally.

Further, the present invention provides a compound library comprising one or more of the compounds selected from the group consisting of the compound of formula (I), pharmaceutically acceptable salt, isomer, hydrate and solvate thereof.

The following Examples are provided to illustrate preferred embodiments of the present invention, and are not intended to limit the scope of the present invention.

EXAMPLES

Preparation Example 1

Preparation of 4-aminothieno[3,2-d]pyrimidine-7-carboxylic acid

<Step 1> Preparation of 3H-thieno[3,2-d]pyrimidin-4-one

Acetic anhydride (185 mL, 1.96 mol) and formic acid (85 mL, 2.22 mmol) were mixed and stirred. Methyl-3-aminothiophene-2-carboxylate (50 g, 0.16 mol) was added to the reaction mixture, followed by stirring for about 3 hours at room temperature. The reaction solvent was removed under reduced pressure. Separately, ammonium formate (90 g, 1.43 mol) and formamide (150 mL, 3.76 mol) were mixed and stirred for about 30 minutes. The synthesized material in the above was added to the resulting reaction solution, followed by stirring 8 hours at 150° C. The reaction solution was cooled to room temperature and stirred for about 12 hours. The generated solid was filtered, and washed with water to obtain the title compound (39 g, 81%).

$^1$H-NMR Spectrum (300 MHz, DMSO-$d_6$): δ 12.48 (br, 1H), 8.18 (d, 1H), 8.14 (s, 1H), 7.40 (d, 1H)

<Step 2> Preparation of 7-bromothieno[3,2-d]pyrimidin-4(3H)-one

Thieno[3,2-d]pyrimidin-4(3H)-one (38.0 g, 0.25 mol) was dissolved in acetic acid (143 mL, 2.5 mol), and bromine (40.4 mL, 0.78 mol) diluted with acetic acid (122 mL, 2.1 mol) was slowly added to the solution prepared. The reaction solution was stirred in a sealed reactor for 18 hours at 120° C. The reaction solution was cooled to room temperature and acetic acid was removed by distillation under reduced pressure. The reaction mixture was poured into an ice water to generate a solid compound, and the resulting solid compound was filtered and dried. The title compound was obtained without purification (37.5 g, 65%).

$^1$H-NMR Spectrum (300 MHz, DMSO-$d_6$): δ 12.75 (brs, 1H), 8.36 (s, 1h), 8.24 (s, 1H)

<Step 3> Preparation of 7-bromo-4-chlorothieno[3,2-d]pyrimidine

Dimethylformamide (25.8 mL, 0.33 mol) and dichloromethane (150 mL) were added to a reactor. Oxalyl chloride (46.4 mL, 0.53 mol) diluted with dichloromethane (150 mL) at room temperature was added to the reactor for about 30 minutes. 7-bromothieno[3,2-d]pyrimidin-4(3H)-one (35 g, 0.15 mol) was added thereto, and then, the reaction solution was heated to reflux for 3 hours. The temperature of the reaction solution was lowered and water was carefully added thereto. The organic layer was separated, and the aqueous layer was subjected to extraction using dichloromethane. The extracted organic layer was dried over anhydrous sodium sulfate. The dried organic layer was filtered and distilled under reduced pressure, and dried with nitrogen gas to obtain the title compound (30.5 g, 85%).

$^1$H-NMR Spectrum (300 MHz, DMSO-$d_6$): δ 9.16 (s, 1H), 8.79 (s, 1H)

<Step 4> Preparation of 7-bromothieno[3,2-d]pyrimidine-4-amine 7-bromo-4-chlorothieno[3,2-d]pyrimidine (84.0 g) obtained in <Step 3> and 2.0 M ammonia (672 mL) were stirred under a solvent of 2-propanol in a sealed condition. The external temperature was raised to a range of 95 to 100° C., followed by stirring for 7 hours. The reaction solution was cooled to room temperature and the solvent was distilled under reduced pressure. Distilled water (400 mL) was added to the concentrated solution, followed by stirring for 30 minutes. The solid compound was filtered and washed with distilled water (168 mL) twice. The resulting compound was dried in an oven at 50° C. to obtain the title compound (75 g, 97%).

$^1$H-NMR Spectrum (300 MHz, DMSO-$d_6$): δ 7.71 (s, 2H), 8.33 (s, 1H), 8.47 (s, 1H)

<Step 5> Preparation of 7-vinylthieno[3,2-d]pyrimidine-4-amine 7-bromothieno[3,2-d]pyrimidine-4-amine (53.0 g, 0.23 mol) obtained in <Step 4>, tetrakis(triphenylphosphine) palladium (15.8 g, 0.014 mol) and copper iodide (5.3 g, 0.028 mol) were stirred under a solvent of 1,4-dioxane (530 mL). Tributyl(vinyl)tin (83.2 mL, 0.276 mL) was slowly added to the resulting mixture, followed by refluxing for 7 hours or more. The reaction solution was cooled to room temperature. An aqueous solution of calcium fluoride (795 mL) and ethyl acetate (795 mL) are added to the reaction solution and stirred vigorously for 3 hours or more. The reaction solution was filtered through a Celite pad under reduced pressure, and washed with ethyl acetate (105 mL). The organic layer of the filtrate was separated, and dried over anhydrous sodium sulfate. The dried organic layer was filtered and distilled under reduced pressure, and a mixed solution of ethyl acetate (106 mL)/hexane (106 mL) was added thereto, followed by stirring for 1 hour. The reaction solution was filtered under reduced pressure and washed with a mixed solution of ethyl acetate (27 mL)/hexane (27 mL). The filtered solid was dried with warm wind in an oven (50° C.) for 3 hours or more to obtain title compound (34.2 g, 83.8%).

$^1$H-NMR Spectrum (300 MHz, DMSO-$d_6$): δ 8.40 (s, 1H), 8.13 (s, 1H), 7.44 (s, 2H), 6.94 (dd, 1H), 6.34 (dd, 1H), 5.37 (dd, 1H)

<Step 6> Preparation of 4-aminothieno[3,2-d]pyrimidine-7-carboaldehyde 7-vinylthieno[3,2-d]pyrimidine-4-amine (40.0 g, 0.226 mol) obtained in <Step 5> was stirred under solvents of chloroform (280 mL) and methanol (280 mL). The reaction solution was cooled to −78° C. by introducing nitrogen gas and supplied by ozone gas for 3 hours or more. The ozone generator was removed and the temperature of the reaction solution was raised to room temperature while nitrogen gas was introduced. Dimethyl sulfide (60 mL) was added to the reaction mixture, followed by stirring for 3 hours or more at room temperature. The reaction solution was concentrated under reduced pressure, and ethyl acetate (80 mL) was added to the concentrated solution, followed by stirring for one hour. The reaction solution was filtered under reduced pressure, and the filtered solid was washed with ethyl acetate (10 mL). The filtered solid was dried with warm wind in an oven (50° C.) for 3 hours or more to obtain the title compound (36 g, 89%).

$^1$H-NMR Spectrum (300 MHz, $CDCl_3$): δ 10.25 (s, 1H), 8.99 (s, 1H), 8.50 (s, 1H), 7.82 (s, 2H)

<Step 7> Preparation of 4-aminothieno[3,2-d]pyrimidine-7-carboxylic acid

Sodium phosphate monobasic dihydrate (48.2 g, 0.402 mol) was dissolved in distilled water (180 mL), and the reaction solution was cooled to 0° C. or below. Separately, 4-aminothieno[3,2-d]pyrimidine-7-carboaldehyde (36.0 g, 0.201 mol) obtained in <Step 6> was dissolved in a mixed solution of acetone (244 mL)/dimethylsulfoxide (176 mL), and the resulting solution was slowly added to a reaction solution at 3° C. or below. Separately, sodium chlorite (30.3 g, 0.268 mol) was dissolved in distilled water (180 mL), and the resulting solution was slowly added to the reaction solution at 3° C. or below. Distilled water (1,280 mL) was added to the reaction solution, followed by stirring for 5 hours or more. The reaction solution was filtered under reduced pressure, and the filtered solid was washed with diethyl ether (72 mL). The filtered solid was added with ethanol (180 mL), and the resulting solution was distilled under reduced pressure. The concentrated solid was dried with warm wind in an oven (50° C.) for 3 hours or more to obtain the title compound (36 g, 91.8%).

$^1$H-NMR Spectrum (300 MHz, DMSO-$d_6$): δ 8.92 (s, 1H), 8.50 (s, 1H), 7.94 (s, 2H)

Preparation Example 2

Preparation of 1-chloro-6-methyl-5-nitroisoquinoline

<Step 1> Preparation of 6-methylisoquinoline

Para-tolualdehyde (53 mL, 0.486 mol) was stirred in a solvent of chloroform (900 mL). Aminoacetaldehyde dimethyl acetal (59.3 mL, 0.486 mol) was slowly added thereto, followed by stirring at 90° C. until about one-half of the reaction solution was evaporated. The reaction solution was cooled to room temperature, and the resulting yellow reaction solution was dissolved in chloroform (400 mL), followed by cooling the solution to 0° C. or below. Ethyl chloroformate (48 mL, 0.486 mol) and triethylphosphite (104 mL, 0.583 mol) were slowly added to the reaction solution. The reaction solution was stirred for 24 hours at room temperature. The reaction solution was cooled to 0° C. or below, slowly added with titanium tetrachloride (213.6 mL, 1.94 mol), and refluxed for 12 hours or more. The reaction solution was cooled to room temperature, and stirred for 12 hours or more. The reaction mixture was poured to an ice water to separate the organic layer and the aqueous layer, and the aqueous layer was washed with dichloromethane. A saturated sodium tartrate solution was added to the aqueous layer, adjusted to pH 9 by adding ammonia water, and subjected to extraction with dichloromethane. The obtained organic layer was dried over anhydrous sodium sulfate, and concentrated under reduced pressure to obtain the title compound (46.3 g, 66%).

$^1$H-NMR Spectrum (300 MHz, DMSO-$d_6$): δ 9.23 (s, 1H), 8.45 (d, 1H), 8.02 (d, 1H), 7.72 (d, 2H), 7.54 (d, 1H), 2.49 (s, 3H)

<Step 2> Preparation of 6-methyl-5-nitroisoquinoline

Sulfuric acid (400 mL) was added to 6-methylisoquinoline (46.3 g, 0.323 mol) obtained in <Step 1> above and the mixture was stirred. The reaction solution was cooled to 0° C. or below, followed by slowly adding potassium nitrate (65.3 g, 0.646 mol). The reaction solution was stirred for 3 hours or more at 0° C. An ice water was poured to the reaction mixture, adjusted to pH 12 by adding 5 N NaOH solution, followed by stirring for 12 hours or more at room temperature. The generated solid was filtered under reduced pressure, and the filtered solid was washed with water. The filtered solid was dried with warm wind in an oven (40° C.) for 3 hours or more to obtain the title compound (43.3 g, 71%).

$^1$H-NMR Spectrum (300 MHz, DMSO-$d_6$): δ 9.46 (s, 1H), 8.67 (d, 1H), 8.37 (d, 1H), 7.79 (d, 1H), 7.62 (d, 1H), 2.54 (s, 3H)

<Step 3> Preparation of 6-methyl-5-nitroisoquinolin-2-oxide 6-methyl-5-nitroisoquinoline (43.3 g, 0.230 mol) obtained in <Step 2> above was dissolved in dichloromethane (650 mL), and the reaction solution was cooled to 0° C. or below. Subsequently, mCPBA (67.5 g, 0.390 mol) was slowly added to the reaction solution, followed by stirring for 10 hours or more at 0° C. The reaction mixture was adjusted to pH 10 by adding 1 N NaOH solution, and subjected to extraction with dichloromethane. The obtained organic layer was dried over anhydrous sodium sulfate, and concentrated under reduced pressure to obtain the title compound (46.5 g, 99%).

$^1$H-NMR Spectrum (300 MHz, $CDCl_3$): δ 8.80 (s, 1H), 8.24 (d, 1H), 7.80 (d, 1H), 7.66 (d, 1H), 7.56 (d, 1H), 2.55 (s, 3H)

<Step 4> Preparation of 1-chloro-6-methyl-5-nitroisoquinoline 6-methyl-5-nitroisoquinoline (46.5 g, 0.228 mol) obtained in <Step 3> above was dissolved in 1,2-dichloroethane (1.8 L), and added with $POCl_3$ (107 mL, 1.14 mol) at room temperature. The reaction solution was refluxed for 7 hours or more. The reaction solution was cooled to room temperature, and the reaction solution was concentrated by distilling the solvent under reduced pressure. The concentrated solid was dissolved in dichloromethane, and then, an ice water was added thereto. The reaction mixture was subjected to extraction with dichloromethane. The obtained organic layer was dried over anhydrous sodium sulfate and concentrated under reduced pressure. The concentrated solid was added with a mixed solution of ethyl acetate/hexane=1/1 (v/v), followed by stirring for 2 hours or more at room temperature. The resulting solid was filtered under reduced pressure, and washed with a mixed solution of ethyl acetate/hexane=1/1 (v/v). The filtered solid was dried with warm wind in an oven (40° C.) for 3 hours or more to obtain the title compound (28 g, 55%).

$^1$H-NMR Spectrum (300 MHz, DMSO-$d_6$): δ 8.53 (m, 2H), 7.92 (d, 1H), 7.67 (d, 1H), 2.72 (s, 3H)

Example 1

Preparation of 4-amino-N-(1-((4-chlorophenyl)amino)-6-methylisoquinolin-5-yl)thieno[3,2-d]pyrimidine-7-carboxamide <Step 1> Preparation of N-(4-chlorophenyl)-6-methyl-5-nitroisoquinolin-1-amine 1-chloro-6-methyl-5-nitroisoquinoline (5.0 g, 22.5 mmol) obtained in <Step 4> of Preparation Example 2 was dissolved in 2-propanol (70 mL), and added with 4-chloroaniline (2.6, 20.4 mmol) at room temperature. The reaction solution was placed in a sealed reactor, and stirred for 10 hours or more at 90° C. The reaction mixture was cooled to room temperature, and the resulting solid was filtered under reduced pressure, followed by washing with ethyl acetate. The filtered solid was dried with warm wind in an oven (40° C.) for 3 hours or more to obtain the title compound (6.1 g, 95%).

$^1$H-NMR Spectrum (300 MHz, DMSO-$d_6$): δ 8.53 (m, 2H), 7.92 (d, 1H), 7.67 (d, 1H), 2.72 (s, 3H)

MS (ESI$^+$, m/z): 314 $[M+H]^+$

<Step 2> Preparation of $N^1$-(4-chlorophenyl)-6-methylisoquinolin-1,5-diamine

Iron (5.4 g, 97.2 mmol) and concentrated hydrochloric acid (0.1 mL) were added to a mixed solution of ethanol/water (50 mL/50 mL), and refluxed for 1 hour. N-(4-chlorophenyl)-6-methyl-5-nitroisoquinolin-1-amine (6.1 g, 19.4 mmol) obtained in <Step 1> above was added to the mixed reaction solution, and further refluxed for 2 hours or more. The reaction mixture was filtered through a Celite pad under reduced pressure, and washed with a mixed solution of chloroform/2-propanol=4/1 (v/v). The filtrate obtained was distilled under reduced pressure, and dissolved in a mixed solution of chloroform/2-propanol=4/1 (v/v). The organic layer was separated, and washed with an aqueous solution of sodium bicarbonate and brine. The obtained organic layer was dried over anhydrous sodium sulfate, filtered, and concentrated under reduced pressure to obtain the title compound (4.6 g, 84%).

$^1$H-NMR Spectrum (300 MHz, DMSO-$d_6$): δ 8.96 (s, 1H), 7.96 (d, 2H), 7.88 (d, 1H), 7.63 (d, 1H), 7.43 (d, 1H), 7.33 (d, 2H), 7.26 (d, 1H), 5.48 (s, 2H), 2.25 (d, 3H)

MS (ESI$^+$, m/z): 284 [M+H]$^+$

<Step 3> Preparation of 4-amino-N-(1-((4-chlorophenyl)amino)-6-methylisoquinolin-5-yl)thieno[3,2-d]pyrimidine-7-carboxamide 4-aminothieno[3,2-d]pyrimidine-7-carboxylic acid (7.9 g, 40.5 mmol) obtained in <Step 7> of Preparation Example 1 was dissolved in dimethylformamide, added with DECP (11.7 mL, 81.1 mmol) and DIPEA (17.7 mL, 97.3 mmol) at 0° C., stirred for 10 minutes. The mixed reaction solution was added with $N^1$-(4-chlorophenyl)-6-methylisoquinolin-1,5-diamine (4.6 g, 16.2 mmol) obtained in <Step 2> above, followed by stirring for 12 hours or more. The reaction mixture was diluted with ethyl acetate, and washed with a saturated aqueous solution of sodium bicarbonate and brine. The organic layer was dried over anhydrous sodium sulfate, filtered, and concentrated under reduced pressure. The concentrated solid was added with ethyl acetate, followed by stirring for 2 hours or more. The resulting solid was dried with warm wind in an oven for 3 hours or more to obtain the title compound (2.7 g, 36%).

$^1$H-NMR Spectrum (300 MHz, DMSO-$d_6$): δ 11.56 (s, 1H), 9.33 (s, 1H), 9.14 (s, 1H), 8.58 (s, 1H), 8.47 (d, 1H), 8.00 (m, 5H), 7.63 (d, 1H), 7.38 (d, 2H), 7.19 (d, 1H), 2.42 (s, 3H)

MS (ESI$^+$, m/z): 461 [M+H]$^+$

Example 2

Preparation of 4-amino-N-(6-methyl-1-((3-(trifluoromethyl)phenyl)amino)isoquinolin-5-yl)thieno[3,2-d]pyrimidine-7-carboxamide The procedures of <Steps 1, 2 and 3> of Example 1 were repeated in sequence, except for using 3-trifluoromethylaniline instead of 4-chloroaniline in <Step 1> of Example 1 to obtain the title compound (22 mg, 26%).

MS (ESI$^+$, m/z): 495 [M+H]$^+$

Example 3

Preparation of N-(1-((4-chlorophenyl)amino)-6-methylisoquinolin-5-yl)-4-(cyclopropylamino)thieno[3,2-d]pyrimidine-7-carboxamide The procedures of <Step 3> of Example 1 were repeated, except for using $N^1$-(4-chlorophenyl)-6-methylisoquinolin-1,5-diamine (0.04 g, 0.14 mmol) and 4-cyclopropylaminothieno[3,2-d]pyrimidine-7-carboxylic acid (see WO 2011009687, 0.18 mmol) obtained in <Step 2> of Example 1 to obtain the title compound (27 mg, 38%).

MS (ESI$^+$, m/z): 501 [M+H]$^+$

Example 4

Preparation of 4-(cyclopropylamino)-N-(6-methyl-1-((3-(trifluoromethyl)phenyl)amino)isoquinolin-5-yl)thieno[3,2-d]pyrimidine-7-carboxamide The procedures of Example 3 were repeated, except for using 6-methyl-$N^1$-(3-trifluoromethyl-phenyl)-isoquinolin-1,5-diamine (0.05 g, 0.16 mmol) obtained in <Step 2> of Example 2 instead of $N^1$-(4-chlorophenyl)-6-methylisoquinolin-1,5-diamine obtained in <Step 2> of Example 1 to obtain the title compound (27 mg, 26%).

MS (ESI$^+$, m/z): 535 [M+H]$^+$

Example 5

Preparation of 4-amino-N-(6-methyl-1-((3-(4-methyl-1H-imidazol-1-yl)-5-(trifluoromethyl)phenyl)amino)isoquinolin-5-yl)thieno[3,2-d]pyrimidine-7-carboxamide The procedures of <Steps 1, 2 and 3> of Example 1 were repeated in sequence, except for using 3-(4-methyl-imidazol-1-yl)-5-trifluoromethyl-phenylamine (see WO 2006135640, 1.62 mmol) instead of 4-chloroaniline in <Step 1> of Example 1 to obtain the title compound (7 mg, 42%).

MS (ESI$^+$, m/z): 575 [M+H]$^+$

Example 6

Preparation of 4-(cyclopropylamino)-N-(6-methyl-1-((3-(4-methyl-1H-imidazol-1-yl)-5-(trifluoromethyl)phenyl)amino)isoquinolin-5-yl)thieno[3,2-d]pyrimidine-7-carboxamide The procedures of <Step 3> of Example 1 were repeated, except for using 6-methyl-$N^1$-(3-(4-methyl-imidazol-1-yl)-5-trifluoromethyl-phenyl)-isoquinolin-1,5-diamine (0.012 g, 0.03 mmol) obtained in Example 5 and 4-cyclopropylaminothieno[3,2-d]pyrimidine-7-carboxylic acid (see WO 2011009687, 0.04 mmol) to obtain the title compound (10 mg, 57%).

MS (ESI$^+$, m/z): 615 [M+H]$^+$

Example 7

Preparation of 4-amino-N-(1-((4-((4-ethylpiperazin-1-yl)methyl)-3-(trifluoromethyl)phenyl)amino)-6-methylisoquinolin-5-yl)thieno[3,2-d]pyrimidine-7-carboxamide <Step 1> Preparation of 1-(bromomethyl)-4-nitro-2-(trifluoromethyl)benzene 1-methyl-4-nitro-2-(trifluoromethyl)benzene (25 g, 122 mmol) was dissolved in dichloroethane (300 mL), followed by stirring. NBS (21.7 g, 122 mmol) and AIBN (2.0 g, 12.2 mmol) were added thereto, followed by further stirring for about 12 hours at 80° C. The resulting solid was filtered under reduced pressure, and dried with warm wind in an oven (40° C.) for 3 hours or more to obtain the title compound (34 g, 98%).

$^1$H-NMR Spectrum (300 MHz, DMSO-$d_6$): δ 8.53 (d, 1H), 8.42 (s, 1H), 8.06 (d, 1H), 4.88 (s, 2H)

MS (ESI$^+$, m/z): 284 [M+H]$^+$

<Step 2> Preparation of 1-ethyl-4-(4-nitro-2-(trifluoromethyl)benzyl)piperazine 1-(bromomethyl)-4-nitro-2-(trifluoromethyl)benzene (34 g, 120 mmol) obtained in <Step 1> above was dissolved in dichloromethane (300 mL), followed by stirring. The reaction solution was added with 1-ethylpiperazine (15.97 mL, 126 mmol) and DIPEA (27.2 mL, 156 mmol), followed by further stirring for about 3 hours at room temperature. The reaction mixture was diluted with dichloromethane, and washed with a saturated aqueous solution of sodium bicarbonate and brine. The organic layer was dried over anhydrous sodium sulfate, filtered, and concentrated under reduced pressure to obtain the title compound (21.7 g, 57%).

$^1$H-NMR Spectrum (300 MHz, DMSO-$d_6$): δ 8.52 (d, 1H), 8.40 (s, 1H), 8.09 (d, 1H), 3.71 (s, 2H), 2.35 (m, 10H), 1.00 (t, 3H)

MS (ESI$^+$, m/z): 318 [M+H]$^+$

<Step 3> Preparation of 4-((4-ethylpiperazin-1-yl)methyl)-3-(trifluoromethyl)aniline 1-ethyl-4-(4-nitro-2-(trifluoromethyl)benzyl)piperazine (21.7 g, 68.3 mmol) obtained in <Step 2> above was dissolved in methanol, followed by stirring. The reaction solution was added with Pd/C (1.8 g, 17.08 mmol), followed by stirring under hydrogen conditions for about 12 hours at room temperature. The reaction mixture was filtered through a Celite pad under reduced pressure, washed with methanol. The filtrate was concentrated under reduced pressure to obtain the title compound (19.4 g, 99%).

$^1$H-NMR Spectrum (300 MHz, DMSO-$d_6$): δ 7.30 (d, 1H), 6.85 (s, 1H), 6.76 (d, 1H), 5.42 (s, 2H), 3.37 (s, 2H), 2.33 (m, 10H) 1.01 (t, 3H)

MS (ESI$^+$, m/z): 288 [M+H]$^+$

<Step 4> Preparation of 4-amino-N-(1-((4-((4-ethylpiperazin-1-yl)methyl)-3-trifluoromethyl)phenyl)amino)-6-methylisoquinolin-5-yl)thieno[3,2-d]pyrimidine-7-carboxamide The procedures of <Steps 1, 2 and 3> of Example 1 were repeated in sequence, except for using 4-((4-ethylpiperazin-1-yl)methyl)-3-(trifluoromethyl)aniline obtained in <Step 3> above instead of 4-chloroaniline in <Step 1> of Example 1 to obtain the title compound (7 mg, 30%).

MS (ESI$^+$, m/z): 621 [M+H]$^+$

Example 8

Preparation of 4-(cyclopropylamino)-N-(1-((4-((4-ethylpiperazin-1-yl)methyl)-3-(trifluoromethyl)phenyl)amino)-6-methylisoquinolin-5-yl)thieno[3,2-d]pyrimidine-7-carboxamide The procedures of <Step 3> of Example 1 were repeated in sequence, except for using $N^1$-(4-(4-ethyl-piperazin-1-ylmethyl)-3-trifluoromethyl-phenyl)-6-methyl-isoquinolin-1,5-diamine (0.015 g, 0.03 mmol) and 4-cyclopropylaminothieno[3,2-d]pyrimidine-7-carboxylic acid (see WO 2011009687, 0.04 mmol) to obtain the title compound (10 mg, 46%).

$^1$H-NMR Spectrum (300 MHz, DMSO-$d_6$): δ 11.59 (s, 1H), 9.48 (s, 1H), 8.94 (s, 1H), 8.64 (m, 2H), 8.48 (m, 2H), 8.31 (s, 1H), 8.24 (d, 1H), 8.01 (d, 1H), 7.63 (d, 2H), 7.20 (d, 1H), 3.62 (s, 2H), 3.06 (m, 1H), 2.70 (m, 10H), 2.42 (s, 3H), 1.13 (m, 3H), 0.87 (br, 2H), 0.7 (br, 2H)

MS (ESI$^+$, m/z): 661 [M+H]$^+$

Example 9

Preparation of N-(1-((4-((4-ethylpiperazin-1-yl)methyl)-3-(trifluoromethyl)phenyl)amino)-6-methylisoquinolin-5-yl)-4-(methylamino)thieno[3,2-d]pyrimidine-7-carboxamide The procedures of <Step 3> of Example 1 were repeated in sequence, except for using $N^1$-(4-(4-ethyl-piperazin-1-ylmethyl)-3-trifluoromethyl-phenyl)-6-methyl-isoquinolin-1,5-diamine (0.020 g, 0.05 mmol) obtained in Example 7 and 4-methylamino-thieno[3,2-d]pyrimidine-7-carboxylic acid (see WO 2011009687, 0.05 mmol) to obtain the title compound (4 mg, 13%).

MS (ESI$^+$, m/z): 635 [M+H]$^+$

Example 10

Preparation of 4-amino-N-(1-((4-(4-ethylpiperazin-1-yl)phenyl)amino)-6-methylisoquinolin-5-yl)thieno[3,2-d]pyrimidine-7-carboxamide The procedures of <Steps 1, 2 and 3> of Example 1 were repeated in sequence, except for using 4-(4-ethyl-piperazin-1-yl)phenylamine (see WO 2009141386, 0.37 mmol) instead of 4-chloroaniline obtained in <Step 1> of Example 1 to obtain the title compound (1.2 mg, 37%).

$^1$H-NMR Spectrum (300 MHz, DMSO-$d_6$): δ 11.54 (s, 1H), 9.04 (s, 1H), 8.96 (s, 1H), 8.60 (s, 1H), 8.44 (d, 1H), 7.97 (s, 2H), 7.91 (d, 1H), 7.69 (d, 2H), 7.57 (d, 1H), 7.07 (d, 1H), 6.95 (d, 2H), 3.07 (m, 4H), 2.50 (m, 4H), 2.37 (m, 5H), 1.03 (t, 3H)

MS (ESI$^+$, m/z): 539 [M+H]$^+$

Example 11

Preparation of 4-amino-N-(1-((4-((4-ethylpiperazin-1-yl)methyl)phenyl)amino)-6-methylisoquinolin-5-yl)thieno[3,2-d]pyrimidine-7-carboxamide The procedures of <Steps 1, 2 and 3> of Example 1 were repeated in sequence, except for using 4-(4-ethyl-piperazin-1-ylmethyl)-phenylamine (see WO 2006000420, 0.37 mmol) instead of 4-chloroaniline obtained in <Step 1> of Example 1 to obtain the title compound (4 mg, 8%).

$^1$H-NMR Spectrum (300 MHz, DMSO-$d_6$): δ 11.56 (s, 1H), 9.20 (s, 1H), 8.96 (s, 1H), 8.60 (s, 1H), 8.47 (d, 1H), 7.98 (m, 3H), 7.82 (d, 2H), 7.61 (d, 1H), 7.24 (d, 1H), 7.15

(d, 1H), 3.43 (s, 2H), 2.43 (s, 3H), 2.35 (m, 10H), 0.99 (t, 3H)

MS (ESI$^+$, m/z): 553 [M+H]$^+$

Example 12

Preparation of 4-amino-N-(6-methyl-1-(phenylamino)isoquinolin-5-yl)thieno[3,2-d]pyrimidine-7-carboxamide The procedures of <Steps 1, 2 and 3> of Example 1 were repeated in sequence, except for using aniline instead of 4-chloroaniline in <Step 1> of Example 1 to obtain the title compound (112 mg, 65.5%).

$^1$H-NMR Spectrum (300 MHz, DMSO-$d_6$): δ 11.55 (s, 1H), 9.21 (s, 1H), 8.96 (s, 1H), 8.58 (s, 1H), 8.50 (d, 1H), 7.98 (m, 3H), 7.91 (d, 2H), 7.61 (d, 1H), 7.36 (m, 2H), 7.15 (d, 1H), 7.01 (t, 1H), 2.48 (s, 3H)

MS (ESI$^+$, m/z): 427 [M+H]$^+$

Example 13

Preparation of 4-amino-N-(1-((4-chloro-3-(trifluoromethyl)phenyl)amino)-6-methylisoquinolin-5-yl)thieno[3,2-d]pyrimidine-7-carboxamide The procedures of <Steps 1, 2 and 3> of Example 1 were repeated in sequence, except for using 4-chloro-3-(trifluoromethyl)aniline instead of 4-chloroaniline in <Step 1> of Example 1 to obtain the title compound (75 mg, 50%).

$^1$H-NMR Spectrum (300 MHz, DMSO-$d_6$): δ 11.58 (s, 1H), 9.62 (s, 1H), 8.94 (s, 1H), 8.58 (s, 1H), 8.50 (s, 1H), 8.35 (d, 1H), 8.07 (d, 1H), 7.94 (s, 2H), 7.67 (dd, 2H), 7.27 (d, 1H), 2.48 (s, 3H)

MS (ESI$^+$, m/z): 529 [M+H]$^+$

Example 14

Preparation of 4-amino-N-(1-((2-methoxy-5-(trifluoromethyl)phenyl)amino)-6-methylisoquinolin-5-yl)thieno[3,2-d]pyrimidine-7-carboxamide The procedures of <Steps 1, 2 and 3> of Example 1 were repeated in sequence, except for using 2-methoxy-5-(trifluoromethyl)analine instead of 4-chloroaniline in <Step 1> of Example 1 to obtain the title compound (53 mg, 35%).

$^1$H-NMR Spectrum (300 MHz, DMSO-$d_6$): δ 11.60 (s, 1H), 8.94 (s, 1H), 8.69 (s, 1H), 8.58 (s, 1H), 8.52 (d, 1H), 8.26 (d, 1H), 8.00 (d, 1H), 7.90 (s, 2H), 7.63 (d, 1H), 7.45 (d, 1H), 7.28 (d, 1H), 7.19 (d, 1H), 3.96 (s, 3H), 2.49 (s, 3H)

MS (ESI$^+$, m/z): 525 [M+H]$^+$

Example 15

Preparation of 4-amino-N-(6-methyl-1-((4-(trifluoromethyl)phenyl)amino)isoquinolin-5-yl)thieno[3,2-d]pyrimidine-7-carboxamide <Step 1> Preparation of 6-methyl-5-nitro-N-(4-(trifluoromethyl)pyridin-2-yl)isoquinolin-1-amine 1-chloro-6-methyl-5-nitroisoquinoline (580 mg, 2.61 mmol) obtained in <Step 4> of Preparation Example 2 was dissolved in 1,4-dioxane (15 mL), and added with 4-(trifluoromethyl)pyridin-2-amine (352 mg, 2.17 mmol), Xantphos (126 mg, 0.214 mmol), $Pd_2(dba)_3$ (80 mg, 0.087 mmol) and $CsCO_3$ (1.4 g, 4.34 mmol). The reaction solution was sealed and stirred for 4 hours or more at 110° C. The reaction mixture was cooled to room temperature, diluted with ethyl acetate, and washed with a saturated aqueous solution of sodium bicarbonate and brine. The organic layer was dried over anhydrous sodium sulfate, filtered and concentrated under reduced pressure. The concentrated compound was purified using silica gel chromatography (ethyl acetate: hexane=1:3 (v/v)) to obtain the title compound (321 mg, 42%).

$^1$H-NMR Spectrum (300 MHz, DMSO-$d_6$): δ 10.50 (s, 1H), 8.79 (d, 1H), 8.65 (m, 2H), 8.26 (s, 1H), 7.70 (d, 1H), 7.35 (d, 1H), 7.07 (s, 1H)

MS (ESI$^+$, m/z): 349 [M+H]$^+$

<Step 2> Preparation of 4-amino-N-(6-methyl-1-((4-trifluoromethyl)pyridin-2-yl)amino)isoquinolin-5-yl)thieno[3,2-d]pyrimidine-7-carboxamide The procedures of <Steps 2 and 3> of Example 1 were repeated in sequence, except for using 6-methyl-5-nitro-N-(4-(trifluoromethyl)pyridin-2-yl)isoquinolin-1-amine obtained in <Step 1> above instead of N-(4-chlorophenyl)-6-methyl-5-nitroisoquinolin-1-amine in <Step 2> of Example 1 to obtain the title compound (19 mg, 17%).

$^1$H-NMR Spectrum (300 MHz, DMSO-$d_6$): δ 11.59 (s, 1H), 10.67 (s, 1H), 9.06 (s, 1H), 8.64 (s, 1H), 8.58 (m, 3H), 8.14 (d, 1H), 7.96 (s, 2H), 7.63 (d, 1H), 7.38 (d, 1H), 7.32 (d, 1H), 2.43 (s, 3H)

MS (ESI$^+$, m/z): 496 [M+H]$^+$

Example 16

Preparation of 4-amino-N-(1-((4-methoxyphenyl)amino)-6-methylisoquinolin-5-yl)thieno[3,2-d]pyrimidine-7-carboxamide The procedures of <Steps 1, 2 and 3> of Example 1 were repeated in sequence, except for using para-anisidine instead of 4-chloroaniline in <Step 1> of Example 1 to obtain the title compound (35 mg, 8%).

$^1$H-NMR Spectrum (300 MHz, DMSO-$d_6$): δ 11.53 (s, 1H), 9.08 (s, 1H), 8.93 (s, 1H), 8.58 (s, 1H), 8.44 (d, 1H), 7.95 (s, 2H), 7.91 (d, 1H), 7.74 (d, 2H), 7.58 (d, 1H), 7.07 (d, 1H), 6.93 (d, 2H), 3.74 (s, 3H), 2.40 (s, 3H)

MS (ESI$^+$, m/z): 457 [M+H]$^+$

Example 17

Preparation of 4-amino -N-(6-methyl-1-(p-tolylamino)isoquinolin-5-yl)thieno[3,2-d]pyrimidine-7-carboxamide The procedures of <Steps 1, 2 and 3> of Example 1 were repeated in sequence, except for using para-toluidine instead of 4-chloroaniline in <Step 1> of Example 1 to obtain the title compound.

MS (ESI$^+$, m/z): 441 [M+H]$^+$

Example 18

Preparation of 4-amino-N-(1-((4-isopropylphenyl)amino)-6-methylisoquinolin-5-yl)thieno[3,2-d]pyrimidine-7-carboxamide The procedures of <Steps 1, 2 and 3> of Example 1 were repeated in sequence, except for using 4-isopropylaniline instead of 4-chloroaniline in <Step 1> of Example 1 to obtain the title compound (150 mg, 31%).

$^1$H-NMR Spectrum (300 MHz, DMSO-$d_6$): δ 11.67 (s, 1H), 8.97 (s, 1H), 8.59 (m, 2H), 8.02 (m, 2H), 7.92 (d, 1H), 7.79 (d, 1H), 7.70 (d, 2H), 7.22 (m, 2H), 7.05 (d, 2H), 3.52 (m, 1H), 2.40 (s, 3H), 1.27 (m, 6H)

MS (ESI$^+$, m/z): 469 [M+H]$^+$

Example 19

Preparation of 4-amino-N-(1-((5-(t-butyl)isoxazol-3-yl)amino-6-methylisoquinolin-5-yl)thieno[3,2-d] pyrimidine-7-carboxamide <Step 1> Preparation of 5-(t-butyl)isoxazol-3-amine 4,4-dimethyl-3-oxopentanenitrile (3 g, 23.97 mmol) was dissolved in distilled water, stirred, and added with NaOH (1.06 g, 26.4 mmol) and $NH_2OH.HCl$ (1.83 g, 26.4 mmol). The reaction solution was stirred for about 30 minutes at room temperature. The reaction mixture was calibrated to yield pH in a range of 8 to 9 by adding an aqueous solution of 1 N NaOH, followed by further stirring for 10 hours or more at 50° C. The reaction mixture was washed 2 to 3 times with carbon tetrachloride, and aqueous layer was calibrated to yield pH in a range of 4 to 5 by adding concentrated HCl. The reaction mixture was further stirred for about 3 hours at 50° C. The reaction mixture was cooled to room temperature, and calibrated to yield pH 12 by adding an aqueous solution of 1 N NaOH. The resulting solid was filtered under reduced pressure, and washed with distilled water. The filtered solid was dried with warm wind in an oven (40° C.) for 3 hours or more to obtain the title compound (2.6 g, 77%).

$^1$H-NMR Spectrum (300 MHz, DMSO-$d_6$): δ 5.49 (s, 1H), 5.40 (s, 2H), 1.21 (s, 9H)

MS (ESI$^+$, m/z): 141 [M+H]$^+$

<Step 2> Preparation of 4-amino-N-(1-((5-t-butyl) isoxazol-3-yl)amino)-6-methylisoquinolin-5-yl) thieno[3,2-d]pyrimidine-7-carboxamide The procedures of <Steps 1, 2 and 3> of Example 1 were repeated in sequence, except for using 5-(t-butyl)isoxazol-3-amine obtained in <Step 1> above, instead of 4-chloroaniline in <Step 1> of Example 1 to obtain the title compound (7 mg, 7%).

$^1$H-NMR Spectrum (300 MHz, DMSO-$d_6$): δ 11.56 (s, 1H), 10.20 (s, 1H), 8.94 (s, 1H), 8.58 (s, 1H), 8.52 (d, 1H), 8.07 (d, 1H), 7.95 (m, 1H), 7.60 (d, 1H), 7.25 (d, 1H), 6.85 (s, 1H), 2.20 (s, 3H), 1.33 (s, 9H)

MS (ESI$^+$, m/z): 474 [M+H]$^+$

Example 20

Preparation of 4-amino-N-(1-((4-fluorophenyl) amino)-6-methylisoquinolin-5-yl)thieno[3,2-d]pyrimidine-7-carboxamide The procedures of <Steps 1, 2 and 3> of Example 1 were repeated in sequence, except for using 4-fluoroaniline instead of 4-chloroaniline in <Step 1> of Example 1 to obtain the title compound (25 mg, 13%).

MS (ESI$^+$, m/z): 445 [M+H]$^+$

Example 21

Preparation of 4-amino-N-(6-methyl-1-(thiazol-2-ylamino)isoquinolin-5-yl)thieno[3,2-d]pyrimidine-7-carboxamide The procedures of <Step 1> of Example 15 and <Steps 2 and 3> of Example 1 were repeated in sequence, except for using 2-aminothiazole instead of 4-(trifluoromethyl)pyridin-2-amine in <Step 1> of Example 15 to obtain the title compound (29 mg, 7.4%).

$^1$H-NMR Spectrum (300 MHz, DMSO-$d_6$): δ 11.59 (s, 1H), 8.95 (s, 1H), 8.58 (s, 1H), 8.50 (s, 1H), 8.15 (d, 1H), 7.97 (s, 2H), 7.69 (m, 1H), 7.60 (m, 1H), 7.29 (m, 2H), 7.11 (m, 1H), 2.42 (s, 3H)

MS (ESI$^+$, m/z): 434 [M+H]$^+$

Example 22

Preparation of 4-amino-N-(1-((4-cyanophenyl) amino)-6-methylisoquinolin-5-yl)thieno[3,2-d]pyrimidine-7-carboxamide The procedures of <Steps 1, 2 and 3> of Example 1 were repeated in sequence, except for using 4-aminobenzonitrile instead of 4-chloroaniline in <Step 1> of Example 1 to obtain the title compound (41 mg, 25%).

$^1$H-NMR Spectrum (300 MHz, DMSO-$d_6$): δ 11.59 (s, 1H), 9.69 (s, 1H), 8.94 (s, 1H), 8.58 (s, 1H), 8.48 (d, 1H), 8.13 (m, 3H), 7.96 (s, 2H), 7.76 (d, 2H), 7.68 (d, 1H), 7.32 (d, 1H), 2.43 (s, 3H)

MS (ESI$^+$, m/z): 452 [M+H]$^+$

Example 23

Preparation of 4-amino-N-(6-methyl-1-(quinolin-5-ylamino)isoquinolin-5-yl)thieno[3,2-d]pyrimidine-7-carboxamide The procedures of <Step 1> of Example 15 and <Steps 2 and 3> of Example 1 were repeated in sequence, except for using 5-aminoquinoline instead of 4-(trifluoromethyl)pyridin-2-amine in <Step 1> of Example 15 to obtain the title compound (15 mg, 8.6%).

$^1$H-NMR Spectrum (300 MHz, DMSO-$d_6$): δ 11.56 (s, 1H), 9.49 (s, 1H), 8.94 (s, 1H), 8.89 (d, 1H), 8.58 (s, 1H), 8.52 (d, 1H), 8.28 (d, 1H), 7.94 (m, 3H), 7.89 (t, 1H), 7.79 (m, 3H), 7.46 (d, 1H), 7.10 (d, 1H), 2.45 (s, 3H)

MS (ESI$^+$, m/z): 478 [M+H]$^+$

Example 24

Preparation of 4-amino-N-(1-((4-ethoxyphenyl) amino)-6-methylisoquinolin-5-yl)thieno[3,2-d]pyrimidine-7-carboxamide The procedures of <Steps 1, 2 and 3> of Example 1 were repeated in sequence, except for using 4-ethoxyaniline instead of 4-chloroaniline in <Step 1> of Example 1 to obtain the title compound (52 mg, 33%).

$^1$H-NMR Spectrum (300 MHz, DMSO-$d_6$): δ 11.53 (s, 1H), 9.08 (s, 1H), 8.93 (s, 1H), 8.41 (s, 1H), 8.44 (d, 1H), 7.94 (m, 3H), 7.72 (d, 2H), 7.58 (d, 1H), 7.63 (d, 1H), 7.07 (d, 1H), 6.92 (d, 2H), 3.41 (q, 2H), 2.40 (s, 3H), 1.35 (t, 3H)

MS (ESI$^+$, m/z): 471 [M+H]$^+$

Example 25

Preparation of 4-amino-N-(6-methyl-1-((4-phenoxyphenyl)amino)isoquinolin-5-yl)thieno[3,2-d]pyrimidine-7-carboxamide The procedures of <Steps 1, 2 and 3> of Example 1 were repeated in sequence, except for using 4-phenoxyphenyl instead of 4-chloroaniline in <Step 1> of Example 1 to obtain the title compound (71 mg, 47%).

$^1$H-NMR Spectrum (300 MHz, DMSO-$d_6$): δ 11.55 (s, 1H), 9.24 (s, 1H), 8.94 (s, 1H), 8.47 (s, 1H), 7.97 (m, 5H), 7.61 (d, 1H), 7.39 (m, 3H), 7.14 (m, 6H), 2.42 (s, 3H)

MS (ESI$^+$, m/z): 519 [M+H]+

Example 26

Preparation of 4-amino-N-(1-((4-hydroxyphenyl)amino)-6-methylisoquinolin-5-yl)thieno[3,2-d]pyrimidine-7-carboxamide The procedures of <Steps 1, 2 and 3> of Example 1 were repeated in sequence, except for using 4-aminophenol instead of 4-chloroaniline in <Step 1> of Example 1 to obtain the title compound.

MS (ESI$^+$, m/z): 443 [M+H]$^+$

Example 27

Preparation of 4-amino-N-(1-((4-isopropoxyphenyl)amino)-6-methylisoquinolin-5-yl)thieno[3,2-d]pyrimidine-7-carboxamide The procedures of <Steps 1, 2 and 3> of Example 1 were repeated in sequence, except for using 4-isopropoxyaniline instead of 4-chloroaniline in <Step 1> of Example 1 to obtain the title compound.

$^1$H-NMR Spectrum (300 MHz, DMSO-$d_6$): δ 11.55 (s, 1H), 8.95 (s, 1H), 8.59 (s, 1H), 8.47 (d, 1H), 7.96 (s, 2H), 7.85 (d, 1H), 7.69 (d, 2H), 7.10 (d, 1H), 6.95 (d, 2H), 4.60 (m, 1H), 2.42 (s, 3H), 1.13 (m, 6H)

MS (ESI$^+$, m/z): 485 [M+H]$^+$

Example 28

Preparation of [4-amino-N-(1-((4-(dimethylamino)-6-methylisoquinolin-5-yl)thieno[3,2-d]pyrimidine-7-carboxamide] *4-amino-N-(1-((4-dimethylaminophenyl)amino)-6-methylisoquinolin-5-yl)thieno[3,2-d]pyrimidine-7-carboxamide*

The procedures of <Steps 1, 2 and 3> of Example 1 were repeated in sequence, except for using N,N-dimethyl-p-phenylenediamine instead of 4-chloroaniline in <Step 1> of Example 1 to obtain the title compound (32 mg, 15%).

$^1$H-NMR Spectrum (300 MHz, DMSO-$d_6$): δ 11.51 (s, 1H), 8.96 (s, 1H), 8.93 (s, 1H), 8.58 (s, 1H), 8.42 (d, 1H), 7.94 (s, 2H), 7.87 (d, 1H), 7.61 (d, 2H), 7.55 (d, 1H), 7.02 (d, 1H), 6.76 (d, 2H), 2.86 (s, 3H), 2.40 (s, 3H)

MS (ESI$^+$, m/z): 470 [M+H]$^+$

Example 29

Preparation of 4-amino-N-(1-((2,3-dihydrobenzo[b][1,4]dioxin-6-yl)amino)-6-methylisoquinolin-5-yl)thieno[3,2-d]pyrimidine-7-carboxamide The procedures of <Steps 1, 2 and 3> of Example 1 were repeated in sequence, except for using 1,4-benzodioxan-6-amine instead of 4-chloroaniline in <Step 1> of Example 1 to obtain the title compound (21 mg, 13%).

$^1$H-NMR Spectrum (300 MHz, DMSO-$d_6$): δ 11.57 (s, 1H), 8.94 (s, 1H), 8.58 (s, 1H), 8.51 (d, 1H), 7.97 (m, 2H), 7.68 (d, 1H), 7.62 (d, 1H), 7.39 (s, 1H), 7.19 (m, 2H), 6.73 (d, 2H), 4.12 (m, 4H), 2.44 (s, 3H)

MS (ESI$^+$, m/z): 485 [M+H]$^+$

Example 30

Preparation of 4-amino-N-(1-((3,4-dimethoxyphenyl)amino)-6-methylisoquinolin-5-yl)thieno[3,2-d]pyrimidine-7-carboxamide The procedures of <Steps 1, 2 and 3> of Example 1 were repeated in sequence, except for using 3,4-dimethoxyaniline instead of 4-chloroaniline in <Step 1> of Example 1 to obtain the title compound (40 mg, 25%).

$^1$H-NMR Spectrum (300 MHz, DMSO-$d_6$): δ 11.59 (s, 1H), 9.41 (s, 1H), 8.94 (s, 1H), 8.80 (s, 1H), 8.51 (m, 2H), 8.13 (s, 2H), 7.87 (m, 2H), 7.78 (m, 1H), 7.34 (m, 1H), 7.05 (m, 1H), 3.76 (d, 6H), 2.36 (s, 3H)

MS (ESI$^+$, m/z): 487 [M+H]$^+$

Example 31

Preparation of 4-amino-N-(1-((3-fluoro-4-methoxyphenyl)amino)-6-methylisoquinolin-5-yl)thieno[3,2-d]pyrimidine-7-carboxamide The procedures of <Steps 1, 2 and 3> of Example 1 were repeated in sequence, except for using 3-fluoro-4-methoxyaniline instead of 4-chloroaniline in <Step 1> of Example 1 to obtain the title compound.

MS (ESI$^+$, m/z): 475 [M+H]$^+$

Example 32

Preparation of 4-amino-N-(6-methyl-1-((3,4,5-trimethoxyphenyl)amino)isoquinolin-5-yl)thieno[3,2-d]pyrimidine-7-carboxamide The procedures of <Steps 1, 2 and 3> of Example 1 were repeated in sequence, except for using 3,4,5-trimethoxyaniline instead of 4-chloroaniline in <Step 1> of Example 1 to obtain the title compound.

$^1$H-NMR Spectrum (300 MHz, DMSO-$d_6$): δ 11.77 (s, 1H), 9.45 (s, 1H), 8.89 (s, 1H), 8.60 (s, 1H), 8.52 (s, 1H), 7.95 (m, 3H), 7.57 (m, 2H), 7.12 (m, 2H), 3.63 (s, 6H), 3.39 (s, 3H)

MS (ESI$^+$, m/z): 517 [M+H]$^+$

Example 33

Preparation of 4-amino-N-(6-methylisoquinolin-5-yl)thieno[3,2-d]pyrimidine-7-carboxamide <Step 1> Preparation of 6-methylisoquinolin-5-amine 6-methyl-5-nitroisoquinoline (1 g, 5.31 mmol) obtained in <Step 2> of Preparation Example 2 was dissolved in ethanol (70 mL), and added with tin(II) chloride (5.46 g, 26.5 mmol) at room temperature. The reaction solution was stirred for 4 hours or more at 100° C. The reaction mixture was cooled to room temperature, diluted with ethyl acetate, and washed with a saturated aqueous solution of sodium bicarbonate and brine. The organic layer was dried over anhydrous sodium sulfate, filtered and concentrated under reduced pressure. The concentrated solid was added with diethyl ether, followed by stirring for 1 hour. The resulting solid was filtered under reduced pressure to obtain the title compound (320 mg, 38%).

$^1$H-NMR Spectrum (300 MHz, DMSO-$d_6$): δ 9.05 (s, 1H), 8.33 (d, 1H), 8.01 (d, 1H), 7.32 (d, 1H), 7.22 (d, 1H), 5.65 (s, 2H), 2.22 (s, 3H)

MS (ESI$^+$, m/z): 159 [M+H]$^+$

<Step 2> Preparation of 4-amino-N-(6-methylisoquinolin-5-yl)thieno[3,2-d]pyrimidine-7-carboxamide The procedures of <Step 3> of Example 1 were repeated, except for using 6-methylisoquinolin-5-amine obtained in <Step 1> above instead of N$^1$-(4-chlorophenyl)-6-methylisoquinolin-1,5-diamine in <Step 3> of Example 1 to obtain the title compound.

$^1$H-NMR Spectrum (300 MHz, DMSO-$d_6$): δ 11.64 (s, 1H), 9.35 (s, 1H), 8.95 (s, 1H), 8.58 (s, 1H), 8.48 (d, 1H), 8.07 (d, 1H), 7.94 (s, 2H), 7.75 (m, 2H), 2.42 (s, 3H)

MS (ESI$^+$, m/z): 336 [M+H]$^+$

Example 34

Preparation of 4-amino-N-(1-(benzo[d][1,3]dioxol-5-ylamino)-6-methylisoquinolin-5-yl)thieno[3,2-d]pyrimidine-7-carboxamide The procedures of <Steps 1, 2 and 3> of Example 1 were repeated in sequence, except for using 3,4-(methylenedioxy) aniline instead of 4-chloroaniline in <Step 1> of Example 1 to obtain the title compound (39 mg, 24%).

$^1$H-NMR Spectrum (300 MHz, DMSO-$d_6$): δ 11.54 (s, 1H), 9.10 (s, 1H), 8.93 (s, 1H), 8.58 (s, 1H), 8.42 (d, 1H), 7.95 (m, 3H), 7.59 (m, 2H), 7.23 (d, 1H), 7.10 (d, 1H), 6.89 (d, 1H), 5.99 (s, 2H), 2.40 (s, 3H)

MS (ESI$^+$, m/z): 471 [M+H]$^+$

Example 35

Preparation of 4-amino-N-(6-methyl-1-((5,6,7,8-tetrahydronaphthalen-2-yl)amino)isoquinolin-5-yl)thieno[3,2-d]pyrimidine-7-carboxamide The procedures of <Steps 1, 2 and 3> of Example 1 were repeated in sequence, except for using 5,6,7,8-tetrahydronaphthylamine instead of 4-chloroaniline in <Step 1> of Example 1 to obtain the title compound.

$^1$H-NMR Spectrum (300 MHz, DMSO-$d_6$): δ 11.60 (s, 1H), 9.44 (s, 1H), 8.93 (s, 1H), 8.57 (m, 3H), 7.94 (m, 2H), 7.54 (m, 3H), 7.00 (m, 2H), 2.41 (s, 3H), 1.74 (s, 4H), 1.00 (s, 4H).

MS (ESI$^+$, m/z): 481 [M+H]$^+$

Example 36

Preparation of 4-amino-N-(4-((4-chlorophenyl)amino)-7-methylquinazolin-8-yl)thieno[3,2-d]pyrimidine-7-carboxamide <Step 1> Preparation of 2-amino-4-methylbenzamide 2-amino-4-methylbenzonitrile (10 g, 75.7 mmol) was dissolved in ethanol, added with potassium hydroxide (21.2 g, 378 mmol), followed by refluxing for 8 hours. The reaction mixture was cooled to room temperature, concentrated under reduced pressure, and dissolved in ethyl acetate. The organic layer formed was washed with a saturated aqueous solution of sodium bicarbonate and brine. The obtained organic layer is dried over anhydrous sodium sulfate, concentrated under reduced pressure, and recrystallized from ethanol to obtain the title compound (4.9 g, 43%).

$^1$H-NMR Spectrum (300 MHz, DMSO-$d_6$): δ 7.40 (d, 1H), 6.52 (s, 2H), 6.45 (s, 1H), 6.28 (d, 1H), 2.14 (s, 3H)

<Step 2> Preparation of 7-methylquinazolin-4-(3H)-one 2-amino-4-methylbenzamide (4.93 g, 32.8 mmol) obtained in <Step 1> above was added with formic acid (30 mL, 787.9 mmol), followed by stirring for 6 hours at 100° C. The reaction mixture was cooled to room temperature, concentrated under reduced pressure, and washed with water. The filtered solid was dried with warm wind in an oven (40° C.) for 6 hours or more to obtain the title compound (4.79 g, 91%).

$^1$H-NMR Spectrum (300 MHz, DMSO-$d_6$): δ 8.06 (s, 1H), 8.00 (d, 1H), 7.47 (s, 1H), 7.34 (d, 1H), 2.45 (s, 3H)

MS (ESI$^+$, m/z): 161 [M+H]$^+$

<Step 3> Preparation of 6-bromo-7-methylquinazolin-4(3H)-one 7-methylquinazolin-4(3H)-one (4.78 g, 29.9 mmol) obtained in <Step 2> above and methanol (1.2 mL) were dissolved in acetic acid (23 mL, 397.5 mmol), and slowly added with bromine (3.1 mL, 59.8 mmol) over a period of 5 minutes at room temperature, followed by stirring for 5 hours at room temperature. The reaction mixture was concentrated under reduced pressure, and added with sodium thiosulfate, followed by stirring for a while. The resulting solid was filtered under reduced pressure, washed with water. The filtered solid was dried with warm wind in an oven (40° C.) for 6 hours or more to obtain the title compound (4.62 g, 65%).

MS (ESI$^+$, m/z): 238 [M+H]$^+$

<Step 4> Preparation of 6-bromo-7-methyl-8-nitroquinazolin-4(3H)-one 6-bromo-7-methylquinazolin-4(3H)-one (2 g, 7.04 mmol) obtained in <Step 3> was added to sulfuric acid (15 mL), and heated to 80° C. The reaction mixture was added with potassium nitrate (1.1 g, 10.56 mmol), followed by stirring for 20 minutes at 80° C. The reaction mixture was cooled to room temperature, and ice water was added thereto. The resulting solid was filtered under reduced pressure, washed with water, and recrystallized from methanol to obtain the title compound (675 mg, 28%).

$^1$H-NMR Spectrum (300 MHz, DMSO-$d_6$): δ 8.41 (s, 1H), 8.25 (s, 1H), 2.42 (s, 3H)

MS (ESI$^+$, m/z): 283 [M+H]$^+$

<Step 5> Preparation of 6-bromo-4-chloro-7-methyl-8-nitroquinazoline 6-bromo-7-methyl-8-nitroquinazolin-4(3H)-one (672 mg, 2.366 mmol) obtain in <Step 4> was added to $POCl_3$ (10 mL), followed by stirring for 4 hours at 130° C. The reaction mixture was cooled to room temperature, and the reaction mixture was distilled under reduced pressure, followed by adding with ice water. The reaction mixture was subjected to extraction with dichloromethane. The obtained organic layer is dried over anhydrous sodium sulfate, filtered, and concentrated under reduced pressure to obtain the title compound (420 mg, 59%).

MS (ESI$^+$, m/z): 301 [M+H]$^+$

<Step 6> Preparation of 6-bromo-N-(4-chlorophenyl)-7-methyl-8-nitroquinazolin-4-amine 6-bromo-4-chloro-7-methyl-8-nitroquinazoline (420 mg, 1.388 mmol) obtained in <Step 5> was dissolved in 2-propanol (8 mL), and 4-chloroaniline (195 mg, 1.527 mmol) was added thereto. The reaction solution was sealed, and stirred for 10 hours or more at 90° C. The reaction mixture was cooled to room temperature, and the resulting solid was filtered under reduced pressure, and washed with ethyl acetate. The filtered solid was dried with warm wind in an oven (40° C.) for 3 hours or more to obtain the title compound (89 mg, 16%).

MS (ESI$^+$, m/z): 392 [M+H]$^+$

<Step 7> Preparation of $N^4$-(4-chlorophenyl)-7-methylquinazolin-4,8-diamine 6-bromo-N-(4-chlorophenyl)-7-methyl-8-nitroquinazolin-4-amine (88 mg, 19.4 mmol) obtained in <Step 6> was dissolved in ethanol, added with 10% Pd/C (9 mg, 0.022 mmol), followed by stirring for 8 hours under hydrogen gas. The reaction mixture was filtered through a Celite pad under reduced pressure, and washed with a mixed solution of chloroform/2-propanol=4/1 (v/v). The resulting filtrate was concentrated under reduced pressure and purified using silica gel chromatography to obtain the title compound (36 mg, 56%).

$^1$H-NMR Spectrum (300 MHz, DMSO-$d_6$): δ 9.58 (s, 1H), 8.54 (s, 1H), 7.96 (d, 2H), 7.62 (d, 1H), 7.43 (d, 2H), 7.28 (d, 1H), 5.61 (s, 2H), 2.27 (s, 3H)

MS (ESI$^+$, m/z): 285 [M+H]$^+$

<Step 8> Preparation of 4-amino-N-(4-((4-chlorophenyl)amino)-7-methylquinazolin-8-yl)thieno[3,2-d]pyrimidine-7-carboxamide 4-aminothieno[3,2-d]pyrimidine-7-carboxylic acid (47 mg, 0.239 mmol) obtained in <Step 7> of Example 1 was dissolved in dimethylformamide, added with DECP (52 μL, 0.358 mmol) and DIPEA (0.1 mL, 0.597 mmol) at 0° C., followed by stirring for 10 minutes. The reaction mixture was added with $N^4$-(4-chlorophenyl)-7-methylquinazolin-4,8-diamine (34 mg, 0.119 mmol) obtained in <Step 7> above, followed by stirring for 10 hours at 40° C. The reaction mixture was diluted with ethyl acetate, and washed with a saturated aqueous solution of sodium bicarbonate and brine. The organic layer is dried over anhydrous sodium sulfate, filtered, and concentrated under reduced pressure. The concentrated solid was added with ethyl acetate, followed by stirring for 2 hours or more. The resulting solid was filtered under reduced pressure, washed with ethyl acetate and methanol. The filtered solid was dried with warm wind in an oven (40° C.) for 3 hours or more to obtain the title compound (5.7 mg, 10%).

$^1$H-NMR Spectrum (300 MHz, DMSO-$d_6$): δ 11.74 (s, 1H), 9.91 (s, 1H), 8.93 (s, 1H), 8.58 (d, 1H), 8.42 (d, 1H), 7.95 (d, 2H), 7.90 (s, 2H), 7.62 (d, 1H), 7.46 (d, 2H), 2.43 (s, 3H)

MS (ESI$^+$, m/z): 462 [M+H]$^+$

Example 37

Preparation of 4-(cyclopropylamino)-N-(1-((4-methoxyphenyl)amino)-6-methylisoquinolin-5-yl)thieno[3,2-d]pyrimidine-7-carboxamide The procedures of Example 16 were repeated in sequence, except for using 4-(cyclopropylamino)thieno[3,2-d]pyrimidine-7-carboxylic acid (see Preparation Example 4 of Korean Patent Publication Number. No. 10-2011-0089108) instead of carboxylic acid in Example 16 to obtain the title compound (32 mg, 24%).

$^1$H-NMR Spectrum (300 MHz, DMSO-$d_6$): δ 11.55 (s, 1H), 9.13 (s, 1H), 9.07 (s, 1H), 8.65 (s, 1H), 8.51 (d, 1H), 8.44 (d, 1H), 7.91 (d, 1H), 7.74 (d, 2H), 7.58 (d, 1H), 7.07 (d, 1H), 6.93 (d, 2H), 3.08 (m, 1H), 2.41 (s, 3H), 0.86 (m, 2H), 0.71 (m, 2H)

MS (ESI$^+$, m/z): 497 [M+H]$^+$

Example 38

Preparation of 4-amino-N-(1-((3-chlorophenyl)amino)-6-methylisoquinolin-5-yl)thieno[3,2-d]pyrimidine-7-carboxamide The procedures of <Steps 1, 2 and 3> of Example 1 were repeated in sequence, except for using 3-chloroaniline instead of 4-chloroaniline in <Step 1> of Example 1 to obtain the title compound (223 mg, 39%).

$^1$H-NMR Spectrum (300 MHz, DMSO-$d_6$): δ 11.56 (s, 1H), 9.35 (s, 1H), 8.93 (s, 1H), 8.57 (s, 1H), 8.45 (d, 1H), 8.14 (m, 1H), 8.03 (d, 1H), 7.94 (s, 2H), 7.84 (d, 1H), 7.62 (d, 1H), 7.33 (t, 1H), 7.20 (d, 1H), 6.99 (dd, 1H), 2.41 (s, 3H)

MS (ESI$^+$, m/z): 460 [M+H]$^+$

Example 39

Preparation of 4-amino-N-(1-((3-bromophenyl)amino)-6-methylisoquinolin-5-yl)thieno[3,2-d]pyrimidine-7-carboxamide The procedures of <Steps 1, 2 and 3> of Example 1 were repeated in sequence, except for using 4-bromoaniline instead of 4-chloroaniline in <Step 1> of Example 1 to obtain the title compound (65 mg, 15%).

$^1$H-NMR Spectrum (300 MHz, DMSO-$d_6$): δ 11.55 (s, 1H), 9.31 (s, 1H), 8.92 (s, 1H), 8.57 (s, 1H), 8.44 (d, 1H), 7.99 (d, 1H), 7.93 (m, 4H), 7.61 (d, 1H), 7.48 (d, 2H), 7.17 (d, 1H), 2.41 (s, 3H)

MS (ESI$^+$, m/z): 504 [M+H]$^+$

Example 40

Preparation of 4-amino-N-(1-((2,4-dichlorophenyl)amino)-6-methylisoquinolin-5-yl)thieno[3,2-d]pyrimidine-7-carboxamide The procedures of <Steps 1, 2 and 3> of Example 1 were repeated in sequence, except for using 2,4-dichloroaniline instead of 4-chloroaniline in <Step 1> of Example 1 to obtain the title compound (45 mg, 42%).

$^1$H-NMR Spectrum (300 MHz, DMSO-$d_6$): δ 11.56 (brs, 1H), 9.05 (brs, 1H), 8.94 (s, 1H), 8.59 (s, 1H), 8.35 (s, 1H), 7.95 (m, 4H), 7.27 (s, 1H), 7.14 (s, 1H), 2.43 (s, 3H)

MS (ESI$^+$, m/z): 495 [M+H]$^+$

Example 41

Preparation of 4-amino-N-(1-((3,4-dichlorophenyl)amino)-6-methylisoquinolin-5-yl)thieno[3,2-d]pyrimidine-7-carboxamide The procedures of <Steps 1, 2 and 3> of Example 1 were repeated in sequence, except for using 3,4-dichloroaniline instead of 4-chloroaniline in <Step 1> of Example 1 to obtain the title compound (47 mg, 43%).

$^1$H-NMR Spectrum (300 MHz, DMSO-$d_6$): δ 11.58 (brs, 1H), 9.47 (brs, 1H), 8.94 (s, 1H), 8.59 (s, 1H), 8.46 (m, 4H), 7.63 (s, 1H), 7.56 (s, 1H), 7.25 (s, 1H), 2.43 (s, 3H)

MS (ESI$^+$, m/z): 495 [M+H]$^+$

Example 42

Preparation of 4-amino-N-(1-((3,5-dichlorophenyl)amino)-6-methylisoquinolin-5-yl)thieno[3,2-d]pyrimidine-7-carboxamide The procedures of <Steps 1, 2 and 3> of Example 1 were repeated in sequence, except for using 3,5-dichloroaniline instead of 4-chloroaniline in <Step 1> of Example 1 to obtain the title compound (42 mg, 41%).

$^1$H-NMR Spectrum (300 MHz, DMSO-$d_6$): δ 11.59 (brs, 1H), 9.51 (brs, 1H), 8.94 (s, 1H), 5.60 (s, 1H), 8.44 (s, 1H), 8.11 (m, 3H), 7.67 (s, 1H), 7.27 (s, 1H), 7.14 (s, 1H), 2.44 (s, 3H)

MS (ESI$^+$, m/z): 495 [M+H]$^+$

Example 43

Preparation of 4-amino-N-(6-methyl-1-((3,4,5-trichlorophenyl)amino)isoquinolin-5-yl)thieno[3,2-d]pyrimidine-7-carboxamide The procedures of <Steps 1, 2 and 3> of Example 1 were repeated in sequence, except for using 2,3,4-trichloroaniline instead of 4-chloroaniline in <Step 1> of Example 1 to obtain the title compound (75 mg, 6%).

MS (ESI$^+$, m/z): 529 [M+H]$^+$

Example 44

Preparation of 4-amino-N-(1-((4-chloro-3-methoxyphenyl)amino)-6-methylisoquinolin-5-yl)thieno[3,2-d]pyrimidine-7-carboxamide The procedures of <Steps 1, 2 and 3> of Example 1 were repeated in sequence, except for using 4-chloro-3-methoxyaniline instead of 4-chloroaniline in <Step 1> of Example 1 to obtain the title compound (103 mg, 9%).

$^1$H-NMR Spectrum (300 MHz, DMSO-$d_6$): δ 11.57 (s, 1H), 9.31 (s, 1H), 8.94 (s, 1H), 8.58 (s, 1H), 8.47 (d, 1H), 8.03 (d, 1H), 7.95 (s, 2H), 7.80 (s, 1H), 7.65 (m, 2H), 7.33 (d, 2H), 7.19 (d, 1H), 3.87 (s, 3H), 2.42 (s, 3H)

MS (ESI$^+$, m/z): 491 [M+H]$^+$

Example 45

Preparation of 4-amino-N-(1-benzylamino-6-methylisoquinolin-5-yl)thieno[3,2-d]pyrimidine-7-carboxamide The procedures of <Steps 1, 2 and 3> of Example 1 were repeated in sequence, except for using benzylamine instead of 4-chloroaniline in <Step 1> of Example 1 to obtain the title compound (32 mg, 32%).

MS (ESI$^+$, m/z): 441 [M+H]$^+$

Example 46

Preparation of 4-amino-N-(6-methyl-1-phenoxyisoquinolin-5-yl)thieno[3,2-d]pyrimidine-7-carboxamide The procedures of <Steps 1, 2 and 3> of Example 1 were repeated in sequence, except for using phenol, KOH, Cu (powder) and 1,4-dioxane instead of 4-chloroaniline and 2-propanol in <Step 1> of Example 1 to obtain the title compound (62 mg, 17%).

$^1$H-NMR Spectrum (300 MHz, DMSO-$d_6$): δ 11.64 (s, 1H), 8.94 (s, 1H), 8.57 (s, 1H), 8.29 (d, 1H), 7.94 (s, 2H), 7.90 (d, 1H), 7.70 (d, 1H), 7.45 (m, 3H), 7.26 (m, 3H), 2.46 (s, 3H)

MS (ESI$^+$, m/z): 427 [M+H]$^+$

Example 47

Preparation of 4-amino-N-(6-methyl-1-((4-morpholinophenyl)amino)isoquinolin-5-yl)thieno[3,2-d]pyrimidine-7-carboxamide The procedures of <Steps 1, 2 and 3> of Example 1 were repeated in sequence, except for using 4-morpholinoaniline instead of 4-chloroaniline in <Step 1> of Example 1 to obtain the title compound (193 mg, 35%).

$^1$H-NMR Spectrum (300 MHz, DMSO-$d_6$): δ 9.03 (s, 1H), 8.92 (s, 1H), 8.57 (s, 1H), 8.41 (d, 1H), 7.93 (br, 2H), 7.88 (d, 1H), 7.68 (d, 2H), 7.55 (d, 1H), 7.04 (d, 1H), 6.92 (d, 2H), 3.74 (m, 4H), 3.05 (m, 4H), 2.39 (s, 3H)

MS (ESI$^+$, m/z): 512 [M+H]$^+$

Example 48

Preparation of N-(1-((4-(1H-pyrrol-1-yl)phenyl)amino)-6-methylisoquinolin-5-yl)-4-aminothieno[3,2-d]pyrimidine-7-carboxamide The procedures of <Steps 1, 2 and 3> of Example 1 were repeated in sequence, except for using 4-(1H-pyrrol-1-yl)aniline instead of 4-chloroaniline in <Step 1> of Example 1 to obtain the title compound (110 mg, 21%).

$^1$H-NMR Spectrum (300 MHz, DMSO-$d_6$): δ 11.59 (s, 1H), 9.30 (s, 1H), 8.93 (s, 1H), 8.57 (s, 1H), 8.48 (d, 1H), 7.97 (m, 4H), 7.62 (d, 1H), 7.51 (d, 2H), 7.30 (s, 2H), 7.16 (d, 1H), 6.23 (s, 2H), 2.41 (s, 3H)

MS (ESI$^+$, m/z): 491 [M+H]$^+$

Example 49

Preparation of 4-amino-N-(6-methyl-1-(pyrimidin-4-ylamino)isoquinolin-5-yl)thieno[3,2-d]pyrimidine-7-carboxamide The procedures of <Steps 1, 2 and 3> of Example 1 were repeated in sequence, except for using 4-aminopyrimidine instead of 4-(trifluoromethyl)pyridine-2-amine in <Step 1> of Example 15 to obtain the title compound (2.3 mg, 1.5%).

$^1$H-NMR Spectrum (300 MHz, DMSO-$d_6$): δ 11.61 (s, 1H), 10.50 (s, 1H), 8.94 (s, 1H), 8.78 (s, 1H), 8.58 (s, 1H), 8.49 (d, 1H), 8.38 (d, 1H), 8.21 (d, 1H), 8.13 (d, 1H), 7.95 (s, 2H), 7.64 (d, 1H), 7.42 (d, 1H), 2.43 (s, 3H)

MS (ESI$^+$, m/z): 429 [M+H]$^+$

Example 50

Preparation of 4-amino-N-(1-((4-(difluoromethoxy)phenyl)amino)-6-methylisoquinolin-5-yl)thieno[3,2-d]pyrimidine-7-carboxamide The procedures of <Steps 1, 2 and 3> of Example 1 were repeated in sequence, except for using 4-(difluoromethoxy)aniline instead of 4-chloroaniline in <Step 1> of Example 1 to obtain the title compound (170 mg, 27%).

$^1$H-NMR Spectrum (300 MHz, DMSO-$d_6$): δ 11.55 (s, 1H), 9.28 (s, 1H), 8.94 (s, 1H), 8.58 (s, 1H), 8.46 (d, 1H), 7.97 (m, 5H), 7.62 (d, 1H), 7.16 (m, 3H), 2.42 (s, 3H)

MS (ESI$^+$, m/z): 493 [M+H]$^+$

Example 51

Preparation of 4-amino-N-(6-methyl-1-((4-(trifluoromethoxy)phenyl)amino)isoquinolin-5-yl)thieno[3,2-d]pyrimidine-7-carboxamide The procedures of <Steps 1, 2 and 3> of Example 1 were repeated in sequence, except for using 4-(trifluoromethoxy)aniline instead of 4-chloroaniline in <Step 1> of Example 1 to obtain the title compound (30 mg, 20%).

$^1$H-NMR Spectrum (300 MHz, DMSO-$d_6$): δ 11.56 (s, 1H), 9.39 (s, 1H), 8.94 (s, 1H), 8.58 (s, 1H), 8.44 (d, 1H), 8.01 (m, 5H), 7.64 (d, 1H), 7.33 (d, 2H), 7.21 (d, 1H), 2.42 (s, 3H)

MS (ESI$^+$, m/z): 511 [M+H]$^+$

Example 52

Preparation of 4-amino-N-(1-((4-chlorophenyl)amino)isoquinolin-5-yl)thieno[3,2-d]pyrimidine-7-carboxamide <Step 1> Preparation of 1-chloro-5-nitroisoquinoline The procedures of <Steps 3 and 4> of Preparation Example 2 were repeated in sequence, except for using 5-nitroisoquinoline instead of 6-methyl-5-nitroisoquinoline in <Step 3> of Preparation Example 2 to obtain the title compound (1.35 g, 40%).

$^1$H-NMR Spectrum (300 MHz, DMSO-$d_6$): δ 8.77 (t, 2H), 8.56 (d, 1H), 8.31 (d, 1H), 8.05 (t, 1H)

MS (ESI$^+$, m/z): 209 [M+H]$^+$

<Step 2> Preparation of 4-amino-N-(1-((4-chlorophenyl)amino)isoquinolin-5-yl)thieno[3,2-d]pyrimidine-7-carboxamide The procedures of <Steps 1, 2 and 3> of Example 1 were repeated in sequence, except for using 1-chloro-5-nitroisoquinoline instead of 1-chloro-6-methyl-5-nitroisoquinoline in <Step 1> of Example 1 to obtain the title compound (40 mg, 24%).

$^1$H-NMR Spectrum (300 MHz, DMSO-$d_6$): δ 12.42 (s, 1H), 9.34 (s, 1H), 9.00 (s, 1H), 8.76 (s, 1H), 8.71 (d, 1H), 8.35 (d, 1H), 8.20 (d, 1H), 8.01 (s, 2H), 7.97 (d, 2H), 7.74 (m, 2H), 7.39 (d, 2H)

MS (ESI$^+$, m/z): 447 [M+H]$^+$

Example 53

Preparation of 4-amino-N-(5-((4-chlorophenyl)amino)naphthalen-1-yl)thieno[3,2-d]pyrimidine-7-carboxamide <Step 1> Preparation of N-(4-chlorophenyl)-5-nitronaphthalen-1-amine 1-bromo-5-nitronaphthalene (131 mg, 0.52 mmol) was dissolved in DMA (5 mL), and added with 4-chloroaniline (60 mg, 0.47 mmol), Xantphos (27 mg, 0.047 mmol), $Pd_2(dba)_3$ (17.2 mg, 0.019 mmol) and $CsCO_3$ (306 mg, 0.94 mmol) at room temperature. The reaction solution was sealed and stirred for about 3 hours under microwave conditions at 140° C. The reaction mixture was cooled to room temperature, diluted with ethyl acetate, and washed with a saturated aqueous solution of sodium bicarbonate and brine. The organic layer was dried over anhydrous sodium sulfate, filtered, and concentrated under reduced pressure. The concentrated compound purified using silica gel chromatography (ethyl acetate:hexane=1:5 (v/v)) to obtain the title compound (92 mg, 66%).

$^1$H-NMR Spectrum (300 MHz, DMSO-$d_6$): δ 10.10 (s, 1H), 9.00 (d, 1H), 8.58 (d, 1H), 8.13 (d, 1H), 7.89 (m, 3H), 7.59 (d, 2H), 7.47 (d, 2H)

MS (ESI$^+$, m/z): 299 [M+H]$^+$

<Step 2> Preparation of 4-amino-N-(1-((4-chlorophenyl)amino)isoquinolin-5-yl)thieno[3,2-d]pyrimidine-7-carboxamide The procedures of <Steps 1, 2 and 3> of Example 1 were repeated in sequence, except for using N-(4-chlorophenyl)-

5-nitronaphthalene-1-amine obtained in <Step 1> instead of N-(4-chlorophenyl)-6-methyl-5-nitroisoquinolin-1-amine in <Step 2> of Example 1 to obtain the title compound (10 mg, 8.2%).

$^1$H-NMR Spectrum (300 MHz, DMSO-$d_6$): δ 12.56 (s, 1H), 9.00 (s, 1H), 8.77 (s, 1H), 8.49 (d, 1H), 8.42 (s, 1H), 8.17 (d, 1H), 8.00 (m, 3H), 7.64 (m, 2H), 7.52 (d, 1H), 7.27 (d, 2H), 7.05 (d, 2H)

MS (ESI$^+$, m/z): 446 [M+H]$^+$

Example 54

Preparation of 4-amino-N-(1-((4-ethynylphenyl) amino)-6-methylisoquinolin-5-yl)thieno[3,2-d]pyrimidine-7-carboxamide The procedures of <Steps 1, 2 and 3> of Example 1 were repeated in sequence, except for using 4-ethynylaniline instead of 4-chloroaniline in <Step 1> of Example 1 to obtain the title compound (114 mg, 46%).

$^1$H-NMR Spectrum (300 MHz, DMSO-$d_6$): δ 12.18 (s, 1H), 8.97 (s, 1H), 8.62 (s, 1H), 8.36 (d, 1H), 8.07 (d, 1H), 7.91 (m, 4H), 7.71 (d, 1H), 7.63 (d, 2H), 7.42 (d, 1H), 5.77 (s, 1H), 5.76 (br, 1H), 2.29 (s, 3H)

MS (ESI$^+$, m/z): 450 [M+H]$^+$

Example 55

Preparation of 4-amino-N-(1-(isopropylamino)-6-methylisoquinolin-5-yl)thieno[3,2-d]pyrimidine-7-carboxamide The procedures of <Steps 1, 2 and 3> of Example 1 were repeated in sequence, except for using isopropylamine instead of 4-chloroaniline in <Step 1> of Example 1 to obtain the title compound (4 mg, 1%).

$^1$H-NMR Spectrum (300 MHz, MeOD): δ 8.89 (s, 1H), 8.58 (s, 1H), 8.16 (d, 1H), 7.77 (d, 1H), 7.50 (d, 1H), 7.00 (d, 1H), 4.34 (m, 1H), 2.47 (s, 3H), 1.25 (d, 6H)

MS (ESI$^+$, m/z): 393 [M+H]$^+$

Example 56

Preparation of 4-amino-N-(1-(indolin-6-ylamino)-6-methylisoquinolin-5-yl)thieno[3,2-d]pyrimidine-7-carboxamide The procedures of <Steps 1, 2 and 3> of Example 1 were repeated in sequence, except for using 6-nitroindoline instead of 4-chloroaniline in <Step 1> of Example 1 to obtain the title compound (12 mg, 3%).

MS (ESI$^+$, m/z): 468 [M+H]$^+$

Example 57

Preparation of 4-amino-N-(1-((4-(fluoromethoxy) phenyl)amino)-6-methylisoquinolin-5-yl)thieno[3,2-d]pyrimidine-7-carboxamide <Step 1> Preparation of 1-(fluoromethoxy)-4-nitrobenzene 4-nitrobenzylalcohol (1 g, 6.53 mmol) was dissolved in dichloromethane (15 mL), and added with $XeF_2$ (1.1 g, 6.53 mmol) at 35° C. The reaction solution was stirred at a temperature in the range of 35 to 40° C. until gas generation has come to a halt. The reaction solution was cooled to room temperature and further stirred for about 7 hours. The reaction mixture was diluted with ethyl acetate, and washed with a saturated aqueous solution of sodium bicarbonate and brine. The organic layer was dried over anhydrous sodium sulfate, filtered and concentrated under reduced pressure. The concentrated compound was purified using silica gel chromatography (ethyl acetate:hexane=1:5 (v/v)) to obtain the title compound (670 mg, 61%).

$^1$H-NMR Spectrum (300 MHz, DMSO-$d_6$): δ 8.29 (d, 2H), 7.35 (d, 2H), 6.09 (s, 1H), 5.91 (s, 1H)

MS (ESI$^+$, m/z): 172 [M+H]$^+$

<Step 2> Preparation of 4-(fluoromethoxy)aniline

The procedures of <Step 2> of Example 1 were repeated, except for using 1-(fluoromethoxy)-4-nitrobenzene obtained in <Step 1> above instead of using N-(4-chlorophenyl)-6-methyl-5-nitroisoquinolin-1-amine in <Step 2> of Example 1 to obtain the title compound (510 mg, 92%).

$^1$H-NMR Spectrum (300 MHz, DMSO-$d_6$): δ 6.80 (d, 2H), 6.55 (d, 2H), 5.73 (s, 1H), 5.55 (s, 1H), 4.84 (s, 2H)

MS (ESI$^+$, m/z): 142 [M+H]$^+$

<Step 3> Preparation of 4-amino-N-(1-((4-(fluoromethoxy)phenyl)amino)-6-methylisoquinolin-5-yl) thieno[3,2-d]pyrimidine-7-carboxamide The procedures of <Steps 1, 2 and 3> of Example 1 were repeated in sequence, except for using 4-(fluoromethoxy) aniline instead of 4-chloroaniline in <Step 1> of Example 1 to obtain the title compound (17 mg, 11%).

$^1$H-NMR Spectrum (300 MHz, DMSO-$d_6$): δ 11.54 (s, 1H), 9.19 (s, 1H), 8.93 (s, 1H), 8.58 (s, 1H), 8.45 (d, 1H), 7.95 (m, 3H), 7.85 (d, 1H), 7.60 (d, 1H), 7.12 (m, 3H), 5.91 (s, 1H), 5.73 (s, 1H), 2.41 (s, 3H)

MS (ESI$^+$, m/z): 475 [M+H]$^+$

Example 58

Preparation of N-(1-(4-chlorophenylamino)-6-methylisoquinolin-5-yl)thieno[3,2-d]pyrimidine-7-carboxamide <Step 1> Preparation of 7-methyl-3H-thieno[3,2-d] pyrimidin-4-one 3-amino-4-methyl-thiophene-2-carboxylic acid methyl ester (10.2 g, 59.6 mmol) was dissolved in formamide (25 mL), followed by refluxing for 24 hours at 200° C. The reaction solution was slowly cooled to room temperature. The resulting solid was filtered, washed with diethyl ether, and dried to obtain the title compound (9 g, 91%).

$^1$H-NMR Spectrum (300 MHz, DMSO-$d_6$): δ 8.17 (s, 1H), 7.81 (s, 1H), 2.31 (s, 3H)

<Step 2> Preparation of 4-chloro-7-methyl-thieno [3,2-d]pyrimidine 7-methyl-3H-thieno[3,2-d]pyrimidin-4-one (9 g, 54.2 mmol), DMF (1 mL), $POCl_3$ (80 mL) were mixed and refluxed for 4 hours at 110° C. The reaction solution was cooled to room temperature, and the reaction mixture was concentrated under reduced pressure. The reaction mixture was added with toluene, and further concentrated under reduced pressure. The resulting residue was neutralized with sodium bicarbonate, subjected to extraction with ethyl acetate, dried, and filtered to obtain the title compound (8.1 g, 81%).

$^1$H-NMR Spectrum (300 MHz, $CDCl_3$): δ 9.01 (s, 1H), 7.69 (s, 1H), 2.53 (s, 3H)

<Step 3> Preparation of 7-methyl-thieno[3,2-d]pyrimidine 4-chloro-7-methyl-thieno[3,2-d]pyrimidine (6.5 g, 35.2 mmol) was dissolved in methanol (200 mL), added with $Pd(OH)_2$ (1.3 g) and triethylamine (4.9 mL, 35.2 mmoL), and stirred for 5 hours under hydrogen pressure conditions. The reaction mixture was filtered through a Celite pad under reduced pressure, and concentrated. The concentrated compound was purified using silica gel chromatography (ethyl acetate:hexane=1:1 (v/v=1/1)) to obtain the title compound (4.5 g, 85%).

$^1$H-NMR Spectrum (300 MHz, $CDCl_3$): δ 9.24 (s, 2H), 7.65 (s, 1H), 2.54 (s, 3H)

<Step 4>7-acetyloxymethyl-thieno[3,2-d]pyrimidine 7-methyl-thieno[3,2-d]pyrimidine (500 mg, 3.33 mmol) was dissolved in benzene (11 mL), added with NBS (539 mg, 3.33 mmol) and AIBN (27 mg, 0.17 mmol), and refluxed for 2 hours at 75° C. The reaction mixture was slowly cooled to room temperature, and added with potassium iodide (553 mg, 3.33 mmol) and DMF (5 mL), followed by stirring for 1 hour at 40° C. Sodium acetate (273 mg, 3.33 mmol) was added thereto, followed by further stirring for 3 hour at 40° C. Additionally, sodium acetate (273 mg, 3.33 mol) was added thereto, and the reaction mixture was stirred for 12 hours at 40° C. The reaction mixture was subjected to extraction with ethyl acetate, washed with water and $NaS_2O_3$ solution, dried and concentrated under reduced pressure. The concentrated compound was purified using silica gel chromatography (ethyl acetate: hexane=1:1 (v/v)) to obtain the title compound (140 mg, 20%).

$^1$H-NMR Spectrum (300 MHz, $CDCl_3$): δ 9.29 (s, 1H), 9.27 (s, 1H), 8.08 (s, 1H), 5.48 (s, 2H), 2.12 (s, 3H)

MS ($ESI^+$, m/z): 209 $[M+H]^+$

<Step 5> Preparation of 7-hydroxymethyl-thieno[3,2-d]pyrimidine 7-acetyloxymethyl-thieno[3,2-d]pyrimidine (134 mg, 0.64 mmol) was dissolved in tetrahydrofuran/water (2 mL/2 mL), added with an aqueous solution of 1 N sodium hydroxide (0.97 mL, 0.97 mmol), followed by stirring for 2 hours at room temperature. The reaction solution was subjected to extraction with ethyl acetate, dried, and filtered to obtain the title compound (86 mg, 77%).

$^1$H-NMR Spectrum (300 MHz, $CDCl_3$): δ 9.25 (s, 1H), 9.17 (s, 1H), 7.92 (s, 1H), 5.04 (s, 2H)

<Step 6> Preparation of thieno[3,2-d]pyrimidine-7-carboaldehyde 7-hydroxymethyl-thieno[3,2-d]pyrimidine (250 mg, 1.56 mmol) was dissolved in dichloromethane (10 mL), added with $MnO_2$ (1.36 g, 15.60 mmol), followed by stirring for 2 hours. The reaction mixture was filtered through a Celite pad under reduced pressure, and concentrated to obtain the title compound (80 mg, 30%).

$^1$H-NMR Spectrum (300 MHz, $CDCl_3$): δ 10.51 (s, 1H), 9.37 (s, 2H), 8.87 (s, 1H)

<Step 7> Preparation of thieno[3,2-d]pyrimidine-7-carboxylic acid

The procedures of <Step 7> of Example 1 were repeated except for using thieno[3,2-d]pyrimidine-7-carboaldehyde (70 mg, 0.43 mmol) instead of 4-aminothieno[3,2-d]pyrimidine-7-carboaldehyde to obtain the title compound (37 mg, 48%).

$^1$H-NMR Spectrum (300 MHz, DMSO-$d_6$): δ 13.06 (brs, 1H), 9.62 (s, 1H), 9.27 (s, 1H), 9.16 (s, 1H)

MS ($ESI^+$, m/z): 181 $[M+H]^+$

<Step 8> Preparation of N-(1-(4-chlorophenylamino)-6-methylisoquinolin-5-yl)thieno[3,2-d]pyrimidine-7-carboxamide The procedures of Example 1 were repeated except for using thieno[3,2-d]pyrimidine-7-carboxylic acid instead of 4-aminothieno[3,2-d]pyrimidine-7-carboxylic acid in <Step 3> of Example 1 to obtain the title compound (10 mg, 12%).

$^1$H-NMR Spectrum (300 MHz, DMSO-$d_6$): δ 11.01 (brs, 1H), 9.77 (s, 1H), 9.41 (s, 1H), 9.33 (brs, 1H), 9.29 (s, 1H), 8.47 (d, 1H), 7.98 (d, 1H), 7.95 (d, 2H), 7.63 (d, 1H), 7.36 (d, 2H), 7.23 (d, 1H), 2.45 (s, 3H)

MS ($ESI^+$, m/z): 446 $[M+H]^+$

Example 59

Preparation of 4-amino-N-(1-((4-chloro-3-((dimethylamino)methyl)phenyl)amino)-6-methylisoquinolin-5-yl)thieno[3,2-d]pyrimidine-7-carboxamide <Step 1> Preparation of 1-(2-chloro-5-nitrophenyl)-N,N-dimethylmethanamine 2-chloro-5-nitrobenzaldehyde (1 g, 5.39 mmol) was dissolved in THF (10 mL), and added with dimethylamine (2 M THF solution, 2.7 mL, 5.39 mmol). The reaction solution was cooled to 0° C., and $NaBH(OAc)_3$ (1.6 g, 7.55 mmol) was slowly added thereto, followed by stirring for 12 hours or more at room temperature. The reaction mixture was added with water, and subjected to extraction with ethyl acetate. The separated organic layer was dried over anhydrous sodium sulfate, filtered, and concentrated under reduced pressure to obtain the title compound (940 mg, 81%).

$^1$H-NMR Spectrum (300 MHz, $CDCl_3$): δ 8.42 (d, 1H), 8.10 (dd, 1H), 7.55 (d, 1H), 3.70 (s, 2H), 2.37 (s, 6H)

MS ($ESI^+$, m/z): 215 $[M+H]^+$

<Step 2> Preparation of 4-chloro-3-((dimethylamino)methyl)aniline

Iron (1.36 g, 21.9 mmol) and concentrated hydrochloric acid (0.15 mL) was added to ethanol/water (20 mL/20 mL), followed by refluxing for 1 hour. The mixed reaction solution was added with 1-(2-chloro-5-nitrophenyl)-N,N-dimethylmethanamine (940 mg, 4.38 mmol) obtained in <Step 1> above, and refluxed for 1 hour. The reaction mixture was filtered through a Celite pad under reduced pressure, and washed with ethanol and chloroform/2-propanol=3/1 (v/v). The resulting filtrate was distilled under reduced pressure, and dissolved in ethyl acetate. The organic layer formed was washed with an aqueous solution of sodium bicarbonate and brine. The obtained organic layer was dried over anhydrous sodium sulfate, filtered and concentrated under reduced pressure. The concentrated compound was purified using silica gel chromatography (chloroform:methanol=30:1→15:1 (v/v)) to obtain the title compound (442 mg, 55%).

$^1$H-NMR Spectrum (300 MHz, $CDCl_3$): δ 7.12 (d, 1H), 6.79 (d, 1H), 6.54 (dd, 1H), 3.64 (brs, 2H), 3.45 (s, 2H), 2.30 (s, 6H)

MS (ESI$^+$, m/z): 185 [M+H]$^+$

<Step 3> Preparation of N-(4-chloro-3-((dimethylamino)methyl)phenyl)-6-methyl-5-nitroisoquinolin-1-amine 4-chloro-3-((dimethylamino)methyl)aniline (227 mg, 1.23 mmol) obtained in <Step 2> above and 1-chloro-6-methyl-5-nitroisoquinoline (300 mg, 1.35 mmol) obtained in <Step 4> of Preparation Example 2 were dissolved in 1,4-dioxane (6 mL), and added with Xantphos (73 mg, 0.123 mmol), $Pd_2$ $(dba)_3$ (75 mg, 0.0615 mmol) and $Cs_2CO_3$ (801.5 mg, 2.46 mmol). The reaction solution was sealed, and stirred for 3 hours at 130° C. The reaction mixture was cooled to room temperature, and subjected to extraction with water and ethyl acetate. The separated organic layer was washed with brine, dried over anhydrous sodium sulfate, filtered, and concentrated under reduced pressure. The concentrated compound was purified using silica gel chromatography (chloroform:methanol=30:1 (v/v)) to obtain the title compound (241.5 mg, 53%).

$^1$H-NMR Spectrum (300 MHz, $CDCl_3$): δ 8.18 (d, 1H), 7.99 (d, 1H), 7.81 (dd, 1H), 7.55 (d, 1H), 7.46 (d, 1H), 7.38 (d, 1H), 6.99 (d, 1H), 3.58 (s, 2H), 2.53 (s, 3H), 2.35 (s, 6H)

MS (ESI$^+$, m/z): 371 [M+H]$^+$

<Step 4> Preparation of N1-(4-chloro-3-((dimethylamino)methyl)phenyl)-6-methylisoquinolin-1,5-diamine Iron (202 mg, 3.25 mmol) and concentrated hydrochloric acid (0.02 mL) were added to ethanol/water (6.5 mL/6.5 mL), followed by refluxing for 1 hour. The mixed reaction solution was added with N-(4-chloro-3-((dimethylamino)methyl)phenyl)-6-methyl-5-nitroisoquinolin-1-amine (241.5 mg, 0.65 mmol) obtained in <Step 3> above, followed by refluxing for 1 hour. The reaction mixture was filtered through a Celite pad under reduced pressure, and washed with ethanol and chloroform/2-propanol=3/1 (v/v). The resulting filtrate was distilled under reduced pressure, and dissolved in chloroform/2-propanol=3/1 (v/v). The organic layer was washed with an aqueous solution of sodium bicarbonate and brine. The obtained organic layer was dried over anhydrous sodium sulfate, filtered, and concentrated under reduced pressure. The concentrated compound was purified using silica gel chromatography (dichloromethane:methanol=9:1 (v/v)) to obtain the title compound (130.9 mg, 59%).

$^1$H-NMR Spectrum (300 MHz, $CDCl_3$): δ 8.06 (d, 1H), 7.84 (dd, 1H), 7.54 (d, 1H), 7.35 (m, 3H), 7.11 (brs, 1H), 7.06 (d, 1H), 4.14 (brs, 2H), 3.57 (s, 2H), 2.35 (s, 3H), 2.34 (s, 6H)

MS (ESI$^+$, m/z): 341 [M+H]$^+$

<Step 5> Preparation of 4-amino-N-(1-((4-chloro-3-((dimethylamino)methyl)phenyl)amino)-6-methylisoquinolin-5-yl)thieno[3,2-d]pyrimidine-7-carboxamide 4-aminothieno[3,2-d]pyrimidine-7-carboxylic acid (90 mg, 0.461 mmol) obtained in <Step 7> of Preparation Example 1 was dissolved in dimethylformamide, and added with HATU (350.6 mg, 0.922 mmol) and DIPEA (0.3 mL, 1.536 mmol), followed by stirring for minutes. The mixed reaction solution was added with N1-(4-chloro-3-((dimethylamino)methyl)phenyl)-6-methylisoquinolin-1,5-diamine (130.9 mg, 0.384 mmol) obtained <Step 4> above, followed by stirring for 12 hours or more. The reaction mixture was diluted with ethyl acetate, and washed with a saturated aqueous solution of sodium bicarbonate and brine. The organic layer was dried over anhydrous sodium sulfate, filtered, and concentrated under reduced pressure. The concentrated solid was added with ethyl acetate, and stirred for 1 hour or more. The resulting solid was filtered under reduced pressure, and washed with ethyl acetate and diethyl ether. The filtered solid was dried under vacuum conditions for 3 hours or more to obtain the title compound (35.7 mg, 18%).

$^1$H-NMR Spectrum (300 MHz, DMSO-$d_6$): δ 11.56 (s, 1H), 9.33 (s, 1H), 8.94 (s, 1H), 8.58 (s, 1H), 8.49 (d, 1H), 8.00 (m, 4H), 7.90 (s, 1H), 7.62 (d, 1H), 7.36 (d, 1H), 7.18 (d, 1H), 3.48 (s, 2H), 2.42 (s, 3H), 2.24 (s, 6H)

MS (ESI$^+$, m/z): 519 [M+H]$^+$

Example 60

Preparation of 4-amino-N-(1-((4-chloro-3-(pyrrolidin-1-ylmethyl)phenyl)amino)-6-methylisoquinolin-5-yl)thieno[3,2-d]pyrimidine-7-carboxamide <Step 1> Preparation of 4-chloro-3-(pyrrolidin-1-ylmethyl)aniline The procedures of <Steps 1 and 2> of Example 59 were repeated, except for using pyrrolidine instead of dimethylamine in <Step 1> of Example 59 to obtain the title compound (973.7 mg, 96%).

$^1$H-NMR Spectrum (300 MHz, $CDCl_3$): δ 7.11 (d, 1H), 6.84 (d, 1H), 6.52 (dd, 1H), 3.67 (s, 2H), 3.64 (brs, 2H), 2.62 (m, 4H), 1.83 (m, 4H)

MS (ESI$^+$, m/z): 211 [M+H]$^+$

<Step 2> Preparation of 4-amino-N-(1-((4-chloro-3-(pyrrolidin-1-ylmethyl)phenyl)amino)-6-methylisoquinolin-5-yl)thieno[3,2-d]pyrimidine-7-carboxamide The procedures of <Steps 3, 4 and 5> of Example 59 were repeated in sequence, except for using 4-chloro-3-(pyrrolidin-1-ylmethyl)aniline obtained in <Step 1> above instead of 4-chloro-3-((dimethylamino)methyl)aniline in <Step 3> of Example 59 to obtain the title compound (147.4 mg, 29%).

$^1$H-NMR Spectrum (300 MHz, DMSO-$d_6$): δ 11.56 (s, 1H), 9.33 (s, 1H), 8.94 (s, 1H), 8.58 (s, 1H), 8.49 (d, 1H), 7.99 (m, 5H), 7.62 (d, 1H), 7.35 (d, 1H), 7.17 (d, 1H), 3.55 (s, 2H), 2.50 (m, 4H), 2.42 (s, 3H), 1.74 (m, 4H)

MS (ESI$^+$, m/z): 545 [M+H]$^+$

Example 61

Preparation of 4-amino-N-(1-((4-chloro-3-((diethylamino)methyl)phenyl)amino)-6-methylisoquinolin-5-yl)thieno[3,2-d]pyrimidine-7-carboxamide <Step 1> Preparation of 4-chloro-3-((diethylamino)methyl)aniline The procedures of <Steps 1 and 2> of Example 59 were repeated in sequence, except for using diethylamine instead of dimethylamine in <Step 1> of Example 59 to obtain the title compound (839 mg, 99%).

$^1$H-NMR Spectrum (300 MHz, $CDCl_3$): δ 7.09 (d, 1H), 6.91 (d, 1H), 6.51 (dd, 1H), 3.63 (brs, 2H), 3.57 (s, 2H), 2.60 (q, 4H), 1.08 (t, 6H)

MS (ESI$^+$, m/z): 213 $[M+H]^+$

<Step 2> Preparation of 4-amino-N-(1-((4-chloro-3-((diethylamino)methyl)phenyl)amino)-6-methylisoquinolin-5-yl)thieno[3,2-d]pyrimidine-7-carboxamide The procedures of <Steps 3, 4 and 5> of Example 59 were repeated in sequence, except for using 4-chloro-3-((diethylamino)methyl)aniline obtained in <Step 1> above instead of 4-chloro-3-((dimethylamino)methyl)aniline in <Step 3> of Example 59 to obtain the title compound (18.3 mg, 5%).

$^1$H-NMR Spectrum (300 MHz, DMSO-$d_6$): δ 11.56 (s, 1H), 9.34 (s, 1H), 8.94 (s, 1H), 8.58 (s, 1H), 8.50 (d, 1H), 7.98 (m, 5H), 7.62 (d, 1H), 7.34 (d, 1H), 7.18 (d, 1H), 3.60 (s, 2H), 2.58 (q, 4H), 2.42 (s, 3H), 1.05 (t, 6H)

MS (ESI$^+$, m/z): 547 $[M+H]^+$

Example 62

Preparation of 4-amino-N-(1-((1,4-diethyl-1,2,3,4-tetrahydroquinoxalin-6-yl)amino)-6-methylisoquinolin-5-yl)thieno[3,2-d]pyrimidine-7-carboxamide The procedures of <Steps 1, 2 and 3> of Example 1 were repeated in sequence, except for using 1,4-diethyl-1,2,3,4-tetrahydroquinoxalin-6-amine instead of 4-chloroaniline in <Step 1> of Example 1 to obtain the title compound (6 mg, 1%).

$^1$H-NMR Spectrum (300 MHz, DMSO-$d_6$): δ 11.60 (s, 1H), 8.97 (s, 1H), 8.61 (m, 2H), 8.41 (d, 1H), 7.98 (s, 2H), 7.61 (d, 1H), 7.26 (s, 1H), 7.10 (d, 1H), 6.89 (s, 1H), 3.41 (m, 8H), 2.41 (s, 3H), 1.16 (s, 6H)

MS (ESI$^+$, m/z): 539 $[M+H]^+$

Example 63

Preparation of 4-amino-N-(1-((4-chloro-3-(piperidin-1-ylmethyl)phenyl)amino)-6-methylisoquinolin-5-yl)thieno[3,2-d]pyrimidine-7-carboxamide <Step 1> Preparation of 4-chloro-3-(piperidin-1-ylmethyl)aniline The procedures of <Steps 1 and 2> of Example 59 were repeated in sequence, except for using piperidine instead of dimethylamine in <Step 1> of Example 59 to obtain the title compound (630 mg, 89%).

$^1$H-NMR Spectrum (300 MHz, DMSO-$d_6$): δ 6.99 (d, 1H), 6.70 (s, 1H), 6.45 (d, 1H), 5.17 (s, 2H), 3.31 (s, 2H), 2.34 (m, 4H), 1.49 (m, 4H), 1.23 (m, 2H)

MS (ESI$^+$, m/z): 225 $[M+H]^+$

<Step 2> Preparation of 4-amino-N-(1-((4-chloro-3-(piperidin-1-ylmethyl)phenyl)amino)-6-methylisoquinolin-5-yl)thieno[3,2-d]pyrimidine-7-carboxamide The procedures of <Steps 3, 4 and 5> of Example 59 were repeated in sequence, except for using 4-chloro-3-(piperidin-1-ylmethyl)aniline obtained in <Step 1> above instead of 4-chloro-3-((dimethylamino)methyl)aniline in <Step 3> of Example 59 to obtain the title compound (1 mg, 1%).

$^1$H-NMR Spectrum (300 MHz, DMSO-$d_6$): δ 11.54 (s, 1H), 8.92 (s, 1H), 8.56 (s, 1H), 7.97 (m, 5H), 7.60 (d, 1H), 7.35 (m, 3H), 7.17 (d, 1H), 3.77 (s, 2H), 2.40 (s, 3H),1.54 (m, 6H), 1.42 (m, 4H)

MS (ESI$^+$, m/z): 558 $[M+H]^+$

Example 64

Preparation of 4-amino-N-(1-((4-chloro-3-(morpholinomethyl)phenyl)amino)-6-methylisoquinolin-5-yl)thieno[3,2-d]pyrimidine-7-carboxamide The procedures of <Steps 1, 2, 3, 4 and 5> of Example 59 were repeated in sequence, except for using morpholine instead of dimethylamine in <Step 1> of Example 59 to obtain the title compound (2 mg, 2.3%)

$^1$H-NMR Spectrum (300 MHz, DMSO-$d_6$): δ 11.56 (s, 1H), 9.35 (s, 1H), 8.94 (s, 1H), 8.58 (s, 1H), 8.49 (d, 1H), 7.99 (m, 5H), 7.62 (d, 1H), 7.37 (d, 1H), 7.18 (d, 1H), 3.63 (m, 4H), 3.55 (s, 2H), 2.48 (s, 3H), 2.42 (m, 4H)

MS (ESI$^+$, m/z): 560 $[M+H]^+$

Example 65

Preparation of 4-amino-N-(1-((4-chloro-3-((4-methylpiperazin-1-yl)methyl)phenyl)amino)-6-methylisoquinolin-5-yl)thieno[3,2-d]pyrimidine-7-carboxamide The procedures of <Steps 1, 2, 3, 4 and 5> of Example 59 were repeated in sequence, except for using 1-methylpiperazine instead of dimethylamine in <Step 1> of Example 59 to obtain the title compound (14 mg, 6.5%)

$^1$H-NMR Spectrum (300 MHz, DMSO-$d_6$): δ 11.56 (s, 1H), 9.34 (s, 1H), 8.94 (s, 1H), 8.58 (s, 1H), 8.49 (d, 1H), 7.98 (m, 5H), 7.62 (d, 1H), 7.35 (d, 1H), 7.18 (d, 1H), 3.54 (s, 2H), 2.42 (s, 3H), 2.31 (m, 4H), 2.27 (m, 4H), 2.16 (s, 3H)

MS (ESI$^+$, m/z): 573 $[M+H]^+$

Example 66

Preparation of 4-amino-N-(1-((4-chloro-3-((diisopropylamino)methyl)phenyl)amino)-6-methylisoquinolin-5-yl)thieno[3,2-d]pyrimidine-7-carboxamide <Step 1> Preparation of 4-chloro-3-((diisopropylamino)methyl)aniline The procedures of <Steps 1 and 2> of Example 59 were repeated in sequence, except for using diisopropylamine instead of dimethylamine in <Step 1> of Example 59 to obtain the title compound (196.6 mg, 41%).

$^1$H-NMR Spectrum (300 MHz, $CDCl_3$): δ 7.07 (m, 2H), 6.48 (dd, 1H), 3.62 (s, 4H), 3.08 (quin, 2H), 1.03 (d, 12H)

MS (ESI$^+$, m/z): 241 $[M+H]^+$

<Step 2> Preparation of 4-amino-N-(1-((4-chloro-3-((diisopropylamino)methyl)phenyl)amino)-6-methylisoquinolin-5-yl)thieno[3,2-d]pyrimidine-7-carboxamide The procedures of <Steps 3, 4 and 5> of Example 59 were repeated in sequence, except for using 4-chloro-3-((diisopropylamino)methyl)aniline obtained in <Step 1> above instead of 4-chloro-3-((dimethylamino)methyl)aniline in <Step 3> of Example 59 to obtain the title compound (8.4 mg, 5%).

$^1$H-NMR Spectrum (300 MHz, DMSO-$d_6$): δ 9.30 (s, 1H), 8.94 (s, 1H), 8.58 (s, 1H), 8.48 (d, 1H), 8.20 (d, 1H), 7.96 (m, 3H), 7.74 (dd, 1H), 7.62 (d, 1H), 7.29 (d, 1H), 7.18 (d, 1H), 3.67 (s, 2H), 3.07 (quin, 2H), 2.42 (s, 3H), 1.23 (s, 3H), 1.04 (d, 12H)

MS (ESI$^+$, m/z): 575 [M+H]$^+$

Example 67

Preparation of 4-amino-N-(6-methyl-1-((3-(methylsulfonamido)phenyl)amino)isoquinolin-5-yl)thieno[3,2-d]pyrimidine-7-carboxamide <Step 1> Preparation of N-(3-((6-methyl-5-nitroisoquinolin-1-yl)amino)phenyl)methanesulfonamide N-(3-aminophenyl)methanesulfonamide (382 mg, 2.05 mmol) and 1-chloro-6-methyl-5-nitroisoquinoline (500 mg, 2.25 mmol) obtained in <Step 4> of Preparation Example 2 were dissolved in isopropanol (10 mL), and the reaction solution was sealed, followed by stirring for 1.5 hours at 120° C. The reaction mixture was cooled to room temperature, and the resulting solid was filtered under reduced pressure, followed by washing with isopropanol and diethyl ether. The filtered solid was dried under vacuum conditions to obtain the title compound (752.8 mg, 99%).

$^1$H-NMR Spectrum (300 MHz, DMSO-$d_6$): δ 9.80 (brs, 1H), 8.75 (d, 1H), 8.05 (d, 1H), 7.75 (m, 2H), 7.58 (d, 1H), 7.35 (t, 1H), 6.94 (d, 1H), 6.89 (d, 1H), 3.04 (s, 3H), 2.50 (s, 3H)

MS (ESI$^+$, m/z): 373 [M+H]$^+$

<Step 2> Preparation of N-(3-((6-methyl-5-nitroisoquinolin-1-yl)amino)phenyl)methanesulfonamide Iron (627.4 mg, 10.11 mmol) and concentrated hydrochloric acid (0.07 mL) were added to ethanol/water (15 mL/15 mL), and refluxed for 1 hour. The mixed reaction solution was added with N-(3-((6-methyl-5-nitroisoquinolin-1-yl)amino)phenyl)methanesulfonamide (752.8 mg, 2.02 mmol) obtained in <Step 1> above, and refluxed for 3 hours. The reaction mixture was filtered through a Celite pad under reduced pressure, and washed with ethanol and chloroform/2-propanol=3/1 (v/v). The resulting filtrate was distilled under reduced pressure, and dissolved in chloroform/2-propanol=3/1 (v/v). The organic layer was washed with an aqueous solution of sodium bicarbonate and brine. The obtained organic layer was dried over anhydrous sodium sulfate, filtered, and concentrated under reduced pressure. The concentrated compound was purified using silica gel chromatography (ethyl acetate:hexane=1:1 (v/v)) to obtain the title compound (543 mg, 79%).

$^1$H-NMR Spectrum (300 MHz, DMSO-$d_6$): δ 9.65 (brs, 1H), 8.92 (brs, 1H), 7.86 (d, 1H), 7.78 (s, 1H), 7.64 (t, 2H), 7.42 (d, 1H), 7.25 (m, 2H), 6.79 (d, 1H), 5.47 (brs, 2H), 3.02 (s, 3H), 1.99 (s, 3H)

MS (ESI$^+$, m/z): 343 [M+H]$^+$

<Step 3> Preparation of 4-amino-N-(6-methyl-1-((3-(methylsulfonamido)phenyl)amino)isoquinolin-5-yl)thieno[3,2-d]pyrimidine-7-carboxamide 4-aminothieno[3,2-d]pyrimidine-7-carboxylic acid (206 mg, 1.051 mmol) obtained in <Step 7> of Preparation Example 1 was dissolved in dimethylformamide, and added with HATU (799 mg, 2.102 mmol) and DIPEA (0.6 mL, 3.504 mmol), followed by stirring for 30 minutes. The mixed reaction solution was added with N-(3-((6-methyl-5-nitroisoquinolin-1-yl)amino)phenyl)methanesulfonamide (300 mg, 0.876 mmol) obtained in <Step 2> above, followed by stirring for 12 hours or more. The reaction mixture was diluted with ethyl acetate, and washed with a saturated aqueous solution of sodium bicarbonate and brine. The organic layer was dried over anhydrous sodium sulfate, filtered, and concentrated under reduced pressure. The concentrated solid was added with ethyl acetate, followed by stirring for 1 hour or more. The resulting solid was filtered under reduced pressure, and washed with ethyl acetate and diethyl ether. The filtered solid was dried under vacuum conditions for 3 hours or more to obtain the title compound (103 mg, 23%).

$^1$H-NMR Spectrum (300 MHz, DMSO-$d_6$): δ 11.56 (brs, 1H), 9.70 (brs, 1H), 9.29 (brs, 1H), 8.94 (s, 1H), 8.58 (s, 1H), 8.48 (d, 1H), 7.99 (m, 3H), 7.80 (s, 1H), 7.64 (t, 2H), 7.28 (t, 1H), 7.18 (d, 1H), 6.84 (d, 1H), 3.03 (s, 3H), 2.42 (s, 3H)

MS (ESI$^+$, m/z): 520 [M+H]$^+$

Example 68

Preparation of tert-butyl 4-(5-((5-(4-aminothieno[3,2-d]pyrimidine-7-carboxamido)-6-methylisoquinolin-1-yl)amino)-2-chlorobenzyl)piperazine-1-carboxylate <Step 1> Preparation of tert-butyl 4-(2-chloro-5-nitrobenzyl)piperazine-1-carboxylate 2-chloro-5-nitrobenzaldehyde (1.03 g, 5.39 mmol) was dissolved in dichloromethane (20 mL), and added with tert-butyl-piperazine-1-carboxylate (1 g, 5.39 mmol). The reaction solution was cooled to 0° C., and slowly added with $NaBH(OAc)_3$ (1.6 g, 7.55 mmol), followed by stirring for 3 hours at room temperature. The reaction mixture was added with water, and subjected to extraction with dichloromethane. The separated organic layer was dried over anhydrous sodium sulfate, filtered, and concentrated under reduced pressure. The concentrated compound was purified using silica gel chromatography (ethyl acetate:hexane=1:7 (v/v)) to obtain the title compound (1.9 g, 99%).

$^1$H-NMR Spectrum (300 MHz, $CDCl_3$): δ 8.42 (d, 1H), 8.10 (dd, 1H), 7.54 (d, 1H), 3.67 (s, 2H), 3.50 (t, 4H), 2.51 (t, 4H), 1.47 (s, 9H)

MS (ESI$^+$, m/z): 356 [M+H]$^+$

<Step 2> Preparation of tert-butyl 4-(5-amino-2-chlorobenzyl)piperazine-1-carboxylate Iron (1.7 g, 26.7 mmol) and concentrated hydrochloric acid (0.2 mL) were added to ethanol/water (45 mL/45 mL), and refluxed for 1 hour. The mixed reaction solution was added with tert-butyl 4-(2-chloro-5-nitrobenzyl)piperazine-1-carboxylate (1.9 g, 5.34 mmol) obtained in <Step 1> above, and further refluxed for 1 hour. The reaction mixture was filtered through a Celite pad under reduced pressure, and washed with ethanol and chloroform/2-propanol=3/1 (v/v). The resulting filtrate was distilled under reduced pressure and dissolved in ethanol and chloroform/2-propanol=3/1 (v/v). The organic layer was washed with an aqueous solution of sodium bicarbonate and brine. The obtained organic layer was dried over anhydrous sodium sulfate, filtered, and concentrated under reduced pressure. The concentrated compound was purified using silica gel chromatography (chloroform:methanol=30:1 (v/v)) to obtain the title compound (1.5 g, 86%).

$^1$H-NMR Spectrum (300 MHz, $CDCl_3$): δ 7.12 (d, 1H), 6.82 (d, 1H), 6.54 (dd, 1H), 3.65 (brs, 2H), 3.53 (s, 2H), 3.46 (t, 4H), 2.47 (t, 4H), 1.46 (s, 9H)

MS (ESI$^+$, m/z): 326 $[M+H]^+$

<Step 3> Preparation of tert-butyl 4-(2-chloro-5-((6-methyl-5-nitroisoquinolin-1-yl)amino)benzyl) piperazine-1-carboxylate tert-butyl 4-(5-amino-2-chlorobenzyl)piperazine-1-carboxylate (500 mg, 1.53 mmol) obtained in <Step 2> above and 1-chloro-6-methyl-5-nitroisoquinoline (375 mg, 1.683 mmol) obtained in <Step 4> of Preparation Example 2 were dissolved in 1,4-dioxane (15 mL), and added with Xantphos (91.3 mg, 0.153 mmol), $Pd_2(dba)_3$ (94 mg, 0.077 mmol) and $Cs_2CO_3$ (997 mg, 3.06 mmol). The reaction solution was sealed, and stirred for 3 hours at 130° C. The reaction mixture was cooled to room temperature, and subjected to extraction with water and ethyl acetate. The separated organic layer was washed with brine, dried over anhydrous sodium sulfate, filtered, and concentrated under reduced pressure. The concentrated compound was purified using silica gel chromatography (ethyl acetate:hexane=1:2 (v/v)) to obtain the title compound (424 mg, 54%).

$^1$H-NMR Spectrum (300 MHz, $CDCl_3$): δ 8.18 (d, 1H), 8.00 (d, 1H), 7.67 (m, 2H), 7.47 (d, 1H) 7.37 (d, 1H), 7.13 (brs, 1H), 7.01 (d, 1H), 3.65 (s, 2H), 3.46 (t, 4H) 2.55 (m, 7H), 1.46 (s, 9H)

MS (ESI$^+$, m/z): 513 $[M+H]^+$

<Step 4> Preparation of tert-butyl 4-(5-((5-amino-6-methylisoquinolin-1-yl)amino)-2-chlorobenzyl) piperazine-1-carboxylate Iron (257 mg, 4.145 mmol) and concentrated hydrochloric acid (0.03 mL) were added to ethanol/water (10 mL/10 mL), and refluxed for 1 hour. The mixed reaction solution was added with tert-butyl 4-(2-chloro-5-((6-methyl-5-nitroisoquinolin-1-yl)amino)benzyl)piperazine-1-carboxylate (424.5 mg, 0.829 mmol) obtained in <Step 3> above, and refluxed for 3 hours. The reaction mixture was filtered a Celite pad under reduced pressure, and washed with ethanol and chloroform/2-propanol=3/1 (v/v). The filtrate obtained was distilled under reduced pressure, and dissolved in chloroform/2-propanol=3/1 (v/v). The organic layer was washed with an aqueous solution of sodium bicarbonate and brine. The obtained organic layer was dried over anhydrous sodium sulfate, filtered, and concentrated under reduced pressure. The concentrated compound was purified using silica gel chromatography (ethyl acetate:hexane=1:3→1:2 (v/v)) to obtain the title compound (286 mg, 72%).

$^1$H-NMR Spectrum (300 MHz, $CDCl_3$): δ 8.06 (d, 1H), 7.68 (m, 2H), 7.34 (m, 3H), 7.07 (d, 2H), 4.15 (brs, 2H), 3.64 (s, 2H), 3.46 (t, 4H), 2.36 (s, 3H), 1.46 (s, 9H)

MS (ESI$^+$, m/z): 483 $[M+H]^+$

<Step 5> Preparation of tert-butyl 4-(5-((5-(4-aminothieno[3,2-d]pyrimidine-7-carboxamido)-6-methylisoquinolin-1-yl)amino)-2-chlorobenzyl)piperazine-1-carboxylate 4-aminothieno[3,2-d]pyrimidin-7-carboxylic acid (140 mg, 0.713 mmol) obtained in <Step 7> of Preparation Example 1 was dissolved in dimethylformamide, and added with HATU (543 mg, 1.426 mmol) and DIPEA (0.4 mL, 2.376 mmol), followed by stirring for 30 minutes. The mixed reaction solution was added with tert-butyl 4-(5-((5-amino-6-methylisoquinolin-1-yl)amino)-2-chlorobenzyl) piperazine-1-carboxylate (286.5 mg, 0.594 mmol) obtained in <Step 4> above, followed by stirring for 12 hours or more. The reaction mixture was diluted with ethyl acetate, and washed with a saturated aqueous solution of sodium bicarbonate and brine. The organic layer was dried over anhydrous sodium sulfate, filtered, and concentrated under reduced pressure. The concentrated solid was added with ethyl acetate, and stirred for 1 hour or more. The resulting solid was filtered under reduced pressure, and washed with ethyl acetate and diethyl ether. The filtered solid was dried under vacuum conditions for 3 hours or more to obtain the title compound (84.5 mg, 22%).

$^1$H-NMR Spectrum (300 MHz, DMSO-$d_6$): δ 11.56 (brs, 1H), 9.34 (brs, 1H), 8.94 (s, 1H), 8.58 (s, 1H), 8.48 (d, 1H), 8.00 (m, 5H), 7.63 (d, 1H), 7.37 (d, 1H), 7.19 (d, 1H), 3.58 (s, 2H), 3.33 (m, 4H), 2.50 (m, 4H), 2.42 (s, 3H), 1.39 (s, 9H)

MS (ESI$^+$, m/z): 660 $[M+H]^+$

Example 69

Preparation of 4-amino-N-(1-((4-chloro-3-(piperazin-1-ylmethyl)phenyl)amino)-6-methylisoquinolin-5-yl)thieno[3,2-d]pyrimidine-7-carboxamide hydrochloride Tert-butyl 4-(5-((5-(4-aminothieno[3,2-d]pyrimidine-7-carboxamido)-6-methylisoquinolin-1-yl)amino)-2-chlorobenzyl)piperazine-1-carboxylate (84.5 mg, 0.128 mmol) obtained in <Step 5> of Example 68 was dissolved in ethyl acetate (6 mL), and added with a hydrochloric acid solution (0.65 mL, 2.56 mmol, 4 N dioxane solution). The reaction solution was stirred for 12 hours or more at room temperature. The resulting solid was filtered under reduced pressure, washed with ethyl acetate and diethyl ether, and dried under reduced pressure to obtain the title compound (78.3 mg, 100%).

MS (ESI$^+$, m/z): 560 $[M+H]^+$

Example 70

Preparation of 4-amino-N-(1-((3-chloro-4-methoxyphenyl)amino)-6-methylisoquinolin-5-yl)thieno[3,2-d]pyrimidine-7-carboxamide The procedures of <Steps 1, 2 and 3> of Example 1 were repeated in sequence, except for using 3-chloro-4-methoxyaniline instead of 4-chloroaniline in <Step 1> of Example 1 to obtain the title compound (135 mg, 23%).

$^1$H-NMR Spectrum (300 MHz, DMSO-$d_6$): δ 11.55 (s, 1H), 9.19 (s, 1H), 8.93 (s, 1H), 8.57 (s, 1H), 8.44 (d, 1H), 8.07 (d, 1H), 7.97 (d, 3H), 7.78 (d, 1H), 7.61 (d, 1H), 7.15 (m, 2H), 3.83 (s, 3H), 2.41 (s, 3H)

MS (ESI$^+$, m/z): 491 $[M+H]^+$

Example 71

Preparation of 4-amino-N-(1-((3-(dimethylcarbamoyl)phenyl)amino)-6-methylisoquinolin-5-yl)thieno[3,2-d]pyrimidine-7-carboxamide The procedures of <Steps 1, 2 and 3> of Example 1 were repeated in sequence, except for using 3-amino-N,N-dimethylbenzamide instead of 4-chloroaniline in <Step 1> of Example 1 to obtain the title compound (20 mg, 5%).

$^1$H-NMR Spectrum (300 MHz, DMSO-$d_6$): δ 11.57 (br, 1H), 9.34 (br, 1H), 8.94 (s, 1H), 8.58 (s, 1H), 8.49-8.46 (d, 1H), 8.02-7.96 (m, 5H), 7.63-7.61 (d, 1H), 7.40-7.35 (t, 1H), 7.18 (d, 1H), 7.00 (d, 1H), 2.99 (s, 6H), 2.42 (s, 3H)

MS (ESI$^+$, m/z): 497 [M+H]$^+$

Example 72

Preparation of 4-amino-N-(6-methyl-1-((3-(methylcarbamoyl)phenyl)amino)isoquinolin-5-yl)thieno[3,2-d]pyrimidine-7-carboxamide The procedures of <Steps 1, 2 and 3> of Example 1 were repeated in sequence, except for using 3-amino-N-methylbenzamide instead of 4-chloroaniline in <Step 1> of Example 1 to obtain the title compound (36 mg, 11%).

$^1$H-NMR Spectrum (300 MHz, DMSO-$d_6$): δ 11.56 (br, 1H), 9.37 (br, 1H), 8.94 (s, 1H), 8.58 (s, 1H), 8.51 (d, 1H), 8.38 (d, 1H), 8.28 (s, 1H), 8.10 (d, 1H), 8.01 (m, 2H), 7.62 (d, 1H), 7.41 (m, 2H), 7.18 (d, 1H), 2.80 (d, 3H), 2.42 (s, 3H)

MS (ESI$^+$, m/z): 483 [M+H]$^+$

Example 73

Preparation of 4-amino-N-(1-((4-chloro-2-fluorophenyl)amino)-6-methylisoquinolin-5-yl)thieno[3,2-d]pyrimidine-7-carboxamide The procedures of <Steps 1, 2 and 3> of Example 1 were repeated in sequence, except for using 4-chloro-2-fluoroaniline instead of 4-chloroaniline in <Step 1> of Example 1 to obtain the title compound (28.5 mg, 9.3%).

$^1$H-NMR Spectrum (300 MHz, DMSO-$d_6$): δ 11.55 (s, 1H), 9.13 (s, 1H), 8.94 (s, 1H), 8.58 (s, 1H), 8.36 (d, 1H), 7.95 (s, 2H), 7.88 (d, 1H), 7.66 (m, 2H), 7.49 (dd, 1H), 7.31 (dd, 1H), 7.16 (d, 1H), 2.42 (s, 3H)

MS (ESI$^+$, m/z): 479 [M+H]$^+$

Example 74

Preparation of 4-amino-N-(1-((4-bromo-2-fluorophenyl)amino)-6-methylisoquinolin-5-yl)thieno[3,2-d]pyrimidine-7-carboxamide The procedures of <Steps 1, 2 and 3> of Example 1 were repeated in sequence, except for using 4-bromo-2-fluoroaniline instead of 4-chloroaniline in <Step 1> of Example 1 to obtain the title compound (51.8 mg, 12.5%).

$^1$H-NMR Spectrum (300 MHz, DMSO-$d_6$): δ 11.55 (s, 1H), 9.15 (s, 1H), 8.94 (s, 1H), 8.58 (s, 1H), 8.35 (d, 1H), 7.95 (s, 2H), 7.87 (d, 1H), 7.62 (m, 3H), 7.41 (d, 1H), 7.14 (d, 1H), 2.42 (s, 3H)

MS (ESI$^+$, m/z): 523 [M+H]$^+$

Example 75

Preparation of 4-amino-N-(1-((4-methoxybenzyl)amino)-6-methylisoquinolin-5-yl)thieno[3,2-d]pyrimidine-7-carboxamide The procedures of <Step 1> of Example 15 and <Steps 2 and 3> of Example 1 were repeated in sequence, except for using 4-methoxybenzylamine instead of 4-(trifluoromethyl) pyridine-2-amine in <Step 1> of Example 15 to obtain the title compound (20 mg, 11%).

$^1$H-NMR Spectrum (300 MHz, DMSO-$d_6$): δ 11.45 (s, 1H), 8.90 (s, 1H), 8.54 (s, 1H), 8.20 (d, 1H), 7.97 (m, 3H), 7.80 (d, 1H), 7.46 (d, 1H), 7.27 (d, 2H), 6.85 (m, 3H), 4.66 (d, 2H), 3.68 (s, 3H), 2.34 (s, 3H)

MS (ESI$^+$, m/z): 471 [M+H]$^+$

Example 76

Preparation of 4-amino-N-(1-((4-chlorobenzyl)amino)-6-methylisoquinolin-5-yl)thieno[3,2-d]pyrimidine-7-carboxamide The procedures of <Step 1> of Example 15 and <Steps 2 and 3> of Example 1 were repeated in sequence, except for using 4-chlorobenzylamine instead of 4-(trifluoromethyl) pyridine-2-amine in <Step 1> of Example 15 to obtain the title compound (20 mg, 11%).

$^1$H-NMR Spectrum (300 MHz, DMSO-$d_6$): δ 11.47 (s, 1H), 8.90 (s, 1H), 8.54 (s, 1H), 8.21 (d, 1H), 8.08 (m, 1H), 7.93 (s, 2H), 7.78 (d, 1H), 7.48 (d, 1H), 7.33 (m, 4H), 6.87 (d, 1H), 4.71 (d, 2H), 2.35 (s, 3H)

MS (ESI$^+$, m/z): 475 [M+H]$^+$

Example 77

Preparation of 4-amino-N-(1-(2-(4-chlorophenyl)hydrazinyl)-6-methylisoquinolin-5-yl)thieno[3,2-d]pyrimidine-7-carboxamide The procedures of <Steps 1, 2 and 3> of Example 1 were repeated in sequence, except for using (4-chlorophenyl) hydrazine instead of 4-chloroaniline in <Step 1> of Example 1 to obtain the title compound (53 mg, 25%).

$^1$H-NMR Spectrum (300 MHz, DMSO-$d_6$): δ 11.57 (br, 1H), 9.34 (br, 1H), 8.94 (s, 1H), 8.58 (s, 1H), 8.47 (d, 1H), 8.01 (m, 5H), 7.64 (d, 1H), 7.38 (d, 2H), 7.19 (d, 1H), 2.42 (s, 3H)

MS (ESI$^+$, m/z): 475 [M+H]$^+$

Example 78

Preparation of 4-amino-N-(1-((3-((dimethylamino)methyl)phenyl)amino)-6-methylisoquinolin-5-yl)thieno[3,2-d]pyrimidine-7-carboxamide The procedures of <Step 1> of Example 15 and <Steps 2 and 3> of Example 1 were repeated in sequence, except for using 3-((dimethylamino)methyl)aniline instead of 4-(trifluoromethyl)pyridine-2-amine in <Step 1> of Example 15 to obtain the title compound (34 mg, 12%).

$^1$H-NMR Spectrum (300 MHz, DMSO-$d_6$): δ 11.55 (s, 1H), 9.19 (s, 1H), 8.94 (s, 1H), 8.58 (s, 1H), 8.49 (d, 1H), 7.98 (m, 3H), 7.89 (d, 1H), 7.74 (s, 1H), 7.60 (d, 1H), 7.28 (t, 1H), 7.14 (d, 1H), 6.91 (d, 1H), 3.38 (s, 2H), 2.41 (s, 3H), 2.17 (s, 6H)

MS (ESI$^+$, m/z): 484 [M+H]$^+$

Example 79

Preparation of 4-amino-N-(6-methyl-1-((4-oxo-4H-chromen-6-yl)amino)isoquinolin-5-yl)thieno[3,2-d]pyrimidine-7-carboxamide The procedures of <Steps 1, 2 and 3> of Example 1 were repeated in sequence, except for using 6-amino-4H-chromen-4-one instead of 4-chloroaniline in <Step 1> of Example 1 to obtain the title compound (10 mg, 2%).

$^1$H-NMR Spectrum (300 MHz, DMSO-$d_6$): δ 11.58 (brs, 1H), 9.56 (brs, 1H), 8.95 (s, 1H), 8.61 (m, 2H), 8.49 (d, 1H), 8.35 (dd, 1H), 8.30 (d, 1H), 8.05 (d, 1H), 7.96 (brs, 2H), 7.67 (m, 2H), 7.23 (d, 1H), 6.34 (d, 1H), 2.43 (s, 3H)

MS (ESI$^+$, m/z): 494 [M+H]$^+$

Example 80

Preparation of N-(1-((3-acetylphenyl)amino)-6-methylisoquinolin-5-yl)-4-aminothieno[3,2-d]pyrimidine-7-carboxamide The procedures of <Steps 1, 2 and 3> of Example 1 were repeated in sequence, except for using 3-aminoacetophenone instead of 4-chloroaniline in <Step 1> of Example 1 to obtain the title compound (25 mg, 16%).

$^1$H-NMR Spectrum (300 MHz, DMSO-$d_6$): δ 11.59 (s, 1H), 9.44 (s, 1H), 9.03 (s, 1H), 8.59 (s, 1H), 8.51 (d, 1H), 8.44 (s, 1H), 8.29 (d, 1H), 8.03 (d, 1H), 7.97 (s, 2H), 7.70 (m, 2H), 7.51 (d, 1H), 7.21 (d, 1H), 2.60 (s, 3H), 2.43 (s, 3H)

MS (ESI$^+$, m/z): 469 [M+H]$^+$

Example 81

Preparation of 4-amino-N-(1-((4-(2-methoxyethoxy)phenyl)amino)-6-methylisoquinolin-5-yl)thieno[3,2-d]pyrimidine-7-carboxamide The procedures of <Steps 1, 2 and 3> of Example 1 were repeated in sequence, except for using 4-(2-methoxyethoxy)aniline instead of 4-chloroaniline in <Step 1> of Example 1 to obtain the title compound (90 mg, 19.4%).

$^1$H-NMR Spectrum (300 MHz, DMSO-$d_6$): δ 11.55 (s, 1H), 8.93 (s, 1H), 8.56 (s, 1H), 8.49 (d, 1H), 7.96 (s, 2H), 7.70 (m, 2H), 7.61 (d, 2H), 7.13 (d, 1H), 7.04 (d, 2H), 4.12 (m, 2H), 3.68 (m, 2H), 3.35 (s, 3H), 2.43 (s, 3H)

MS (ESI$^+$, m/z): 501 [M+H]$^+$

Example 82

Preparation of 4-amino-N-(6-methyl-1((3-trifluoromethoxy)phenyl)amino)isoquinolin-5-yl)thieno[3,2-d]pyrimidine-7-carboxamide The procedures of <Steps 1, 2 and 3> of Example 1 were repeated in sequence, except for using 3-(trifluoromethoxy)aniline instead of 4-chloroaniline in <Step 1> of Example 1 to obtain the title compound (71 mg, 15%).

$^1$H-NMR Spectrum (300 MHz, DMSO-$d_6$): δ 11.57 (s, 1H), 9.55 (s, 1H), 8.96 (s, 1H), 8.59 (s, 1H), 8.49 (d, 1H), 8.09 (s, 1H), 8.03 (m, 2H), 7.93 (d, 1H), 7.66 (d, 1H), 7.45 (t, 1H), 7.23 (d, 1H), 6.97 (d, 1H), 2.43 (s, 3H)

MS (ESI$^+$, m/z): 511 [M+H]$^+$

Example 83

Preparation of N-(1-((4-acetylphenyl)amino)-6-methylisoquinolin-5-yl)-4-aminothieno[3,2-d]pyrimidine-7-carboxamide The procedures of <Steps 1, 2 and 3> of Example 1 were repeated in sequence, except for using 4-aminoacetophenone instead of 4-chloroaniline in <Step 1> of Example 1 to obtain the title compound (46.7 mg, 14.5%).

$^1$H-NMR Spectrum (300 MHz, DMSO-$d_6$): δ 11.58 (s, 1H), 9.61 (s, 1H), 8.94 (s, 1H), 8.57 (s, 1H), 8.48 (d, 1H), 8.08 (m, 3H), 7.96 (m, 4H), 7.64 (d, 1H), 7.27 (d, 1H), 2.52 (s, 3H), 2.42 (s, 3H)

MS (ESI$^+$, m/z): 469 [M+H]$^+$

Example 84

Preparation of 4-amino-N-(6-methyl-1-((4-(methylsulfonamido)phenyl)amino)isoquinolin-5-yl)thieno[3,2-d]pyrimidine-7-carboxamide The procedures of <Steps 1, 2 and 3> of Example 1 were repeated in sequence, except for using N-(4-aminophenyl)methanesulfonamide instead of 4-chloroaniline in <Step 1> of Example 1 to obtain the title compound (5 mg, 3%).

$^1$H-NMR Spectrum (300 MHz, DMSO-$d_6$): δ 11.56 (brs, 1H), 9.45 (brs, 1H), 9.23 (brs, 1H), 8.94 (s, 1H), 8.58 (s, 1H), 8.46 (d, 1H), 7.97 (brs, 2H), 7.97 (d, 1H), 7.84 (d, 2H), 7.61 (d, 1H), 7.20 (d, 1H), 2.94 (s, 3H), 2.41 (s, 3H)

MS (ESI$^+$, m/z): 519 [M+H]$^+$

Example 85

Preparation of 4-amino-N-(6-methyl-1-((3-(methylsulfonyl)phenyl)amino)isoquinolin-5-yl)thieno[3,2-d]pyrimidine-7-carboxamide The procedures of <Steps 1, 2 and 3> of Example 1 were repeated in sequence, except for using 3-(methylsulfonyl)aniline instead of 4-chloroaniline in <Step 1> of Example 1 to obtain the title compound (8 mg, 17%).

$^1$H-NMR Spectrum (300 MHz, DMSO-$d_6$): δ 11.59 (brs, 1H), 9.63 (brs, 1H), 8.95 (s, 1H), 8.59 (s, 1H), 8.52 (m, 2H), 8.36 (d, 1H), 8.06 (d, 1H), 7.97 (brs, 2H), 7.67 (m, 3H), 7.25 (d, 1H), 3.22 (s, 3H), 2.43 (s, 3H)

MS (ESI$^+$, m/z): 504 [M+H]$^+$

Example 86

Preparation of 4-amino-N-(1-((4-chloro-3-(methoxymethyl)phenyl)amino)-6-methylisoquinolin-5-yl)thieno[3,2-d]pyrimidine-7-carboxamide The procedures of <Steps 1, 2 and 3> of Example 1 were repeated in sequence, except for using 4-chloro-3-(methoxymethyl)aniline instead of 4-chloroaniline in <Step 1> of Example 1 to obtain the title compound.

MS (ESI$^+$, m/z): 505 [M+H]$^+$

Example 87

Preparation of 4-amino-N-(1-((4-methoxy-3-(methylsulfonamido)phenyl)amino)-6-methylisoquinolin-5-yl)thieno[3,2-d]pyrimidine-7-carboxamide The procedures of <Steps 1, 2 and 3> of Example 1 were repeated in sequence, except for using N-(5-amino-2-methoxyphenyl)methanesulfonamide instead of 4-chloroaniline in <Step 1> of Example 1 to obtain the title compound (132 mg, 16%).

$^1$H-NMR Spectrum (300 MHz, DMSO-$d_6$): δ 11.55 (brs, 1H), 9.18 (brs, 1H), 8.94 (s, 1H), 8.91 (brs, 1H), 8.58 (s, 1H), 8.46 (d, 2H), 7.98 (brs, 2H), 7.94 (d, 1H), 7.76 (s, 1H), 7.73 (d, 1H), 7.59 (d, 1H), 7.11 (d, 1H), 7.06 (d, 1H), 3.82 (s, 3H), 3.00 (s, 3H), 2.41 (s, 3H)

MS ($ESI^+$, m/z): 549 $[M+H]^+$

Example 88

Preparation of 4-amino-N-(1-((4-chloro-3-(methylsulfonamido)phenyl)amino)-6-methylisoquinolin-5-yl)thieno[3,2d]pyrimidine-7-carboxamide The procedures of <Steps 1, 2 and 3> of Example 1 were repeated in sequence, except for using N-(5-amino-2-chlorophenyl)methanesulfonamide instead of 4-chloroaniline in <Step 1> of Example 1 to obtain the title compound (70 mg, 11%).

$^1$H-NMR Spectrum (300 MHz, DMSO-$d_6$): δ 11.58 (brs, 1H), 9.43 (brs, 2H), 8.95 (s, 1H), 8.58 (s, 1H), 8.48 (d, 2H), 8.02 (m, 3H), 7.92 (d, 1H), 7.64 (d, 1H), 7.45 (d, 1H), 7.21 (d, 1H), 3.08 (s, 3H), 2.42 (s, 3H)

MS ($ESI^+$, m/z): 553 $[M+H]^+$

Example 89

Preparation of 4-amino-N-(1-((6-chloropyridin-3-yl)amino)-6-methylisoquinolin-5-yl)thieno[3,2-d]pyrimidine-7-carboxamide The procedures of <Step 1> of Example 15 and <Steps 2 and 3> of Example 1 were repeated in sequence, except for using 5-amino-2-chloropyridine instead of aniline in <Step 1> of Example 15 to obtain the title compound (10 mg, 3.1%).

$^1$H-NMR Spectrum (300 MHz, DMSO-$d_6$): δ 11.57 (s, 1H), 9.66 (s, 1H), 9.16 (s, 1H), 8.88 (d, 1H), 8.57 (s, 1H), 8.45 (m, 2H), 8.02 (d, 1H), 7.96 (s, 2H), 7.66 (d, 1H), 7.49 (d, 1H), 7.23 (d, 1H), 2.41 (s, 3H)

MS ($ESI^+$, m/z): 462 $[M+H]^+$

Example 90

Preparation of 4-amino-N-(1-((2-chloropyridin-4-yl)amino)-6-methylisoquinolin-5-yl)thieno[3,2-d]pyrimidine-7-carboxamide The procedures of <Step 1> of Example 15 and <Steps 2 and 3> of Example 1 were repeated in sequence, except for using 4-amino-2-chloropyridine instead of aniline in <Step 1> of Example 15 to obtain the title compound (61.1 mg, 21%).

$^1$H-NMR Spectrum (300 MHz, DMSO-$d_6$): δ 11.62 (s, 1H), 9.86 (s, 1H), 8.95 (s, 1H), 8.59 (s, 1H), 8.45 (d, 1H), 8.21 (m, 3H), 7.97 (s, 2H), 7.88 (dd, 1H), 7.72 (d, 1H), 7.39 (d, 1H), 2.45 (s, 3H)

MS ($ESI^+$, m/z): 462 $[M+H]^+$

Example 91

Preparation of 4-amino-N-(6-methyl-1-((4-(methylsulfonamidomethyl)phenyl)amino)isoquinolin-5-yl)thieno[3,2-d]pyrimidine-7-carboxamide The procedures of <Steps 1, 2 and 3> of Example 1 were repeated in sequence, except for using N-(4-aminobenzyl)methanesulfonamide instead of 4-chloroaniline in <Step 1> of Example 1 to obtain the title compound (123 mg, 34%).

$^1$H-NMR Spectrum (300 MHz, DMSO-$d_6$): δ 11.56 (brs, 1H), 8.94 (s, 1H), 8.58 (s, 1H), 8.48 (d, 2H), 7.99 (m, 3H), 7.87 (d, 2H), 7.62 (d, 1H), 7.51 (br, 1H), 7.31 (d, 2H), 7.15 (d, 1H), 4.12 (m, 2H), 2.84 (s, 3H), 2.42 (s, 3H)

MS ($ESI^+$, m/z): 533 $[M+H]^+$

Example 92

Preparation of 4-amino-N-(6-methyl-1-((3-(methylsulfonamidomethyl)phenyl)amino)isoquinolin-5-yl)thieno[3,2-d]pyrimidine-7-carboxamide The procedures of <Steps 1, 2 and 3> of Example 1 were repeated in sequence, except for using N-(3-aminobenzyl)methanesulfonamide instead of 4-chloroaniline in <Step 1> of Example 1 to obtain the title compound (205 mg, 31%).

$^1$H-NMR Spectrum (300 MHz, DMSO-$d_6$): δ 11.56 (brs, 1H), 9.27 (brs, 1H), 8.94 (s, 1H), 8.58 (s, 1H), 8.50 (d, 1H), 7.99 (m, 3H), 7.85 (m, 2H), 7.62 (m, 2H), 7.33 (t, 1H), 7.16 (d, 1H), 6.99 (d, 1H), 4.17 (d, 2H), 2.90 (s, 3H), 2.42 (s, 3H)

MS ($ESI^+$, m/z): 534 $[M+H]^+$

Example 93

Preparation of 4-amino-N-(1-((4-chloro-3-fluorophenyl)amino)-6-methylisoquinolin-5-yl)thieno[3,2-d]pyrimidine-7-carboxamide The procedures of <Steps 1, 2 and 3> of Example 1 were repeated in sequence, except for using 4-chloro-3-fluoroaniline instead of 4-chloroaniline in <Step 1> of Example 1 to obtain the title compound (200 mg, 29%).

$^1$H-NMR Spectrum (300 MHz, DMSO-$d_6$): δ 11.58 (s, 1H), 9.51 (s, 1H), 8.94 (s, 1H), 8.58 (s, 1H), 8.46 (d, 1H), 8.22 (dd, 1H), 8.06 (d, 1H), 7.96 (br, 2H), 7.74 (dd, 1H), 7.65 (d, 1H), 7.49 (t, 1H), 7.24 (d, 1H), 2.42 (s, 3H)

MS ($ESI^+$, m/z): 479 $[M+H]^+$

Example 94

Preparation of 4-amino-N-(1-((3-bromo-4-chlorophenyl)amino)-6-methylisoquinolin-5-yl)thieno[3,2-d]pyrimidine-7-carboxamide The procedures of <Steps 1, 2 and 3> of Example 1 were repeated in sequence, except for using 3-bromo-4-chloroaniline instead of 4-chloroaniline in <Step 1> of Example 1 to obtain the title compound (269 mg, 35%).

$^1$H-NMR Spectrum (300 MHz, DMSO-$d_6$): δ 11.59 (brs, 1H), 9.47 (brs, 1H), 8.95 (s, 1H), 8.58 (s, 1H), 8.49 (m, 2H), 8.07 (d, 1H), 8.01 (m, 3H), 7.66 (d, 1H), 7.57 (d, 1H), 7.24 (d, 1H), 2.43 (s, 3H)

MS ($ESI^+$, m/z): 538 $[M+H]^+$

Example 95

Preparation of 4-amino-N-(1-((4-(dimethylcarbamoyl)phenyl)amino)-6-methylisoquinolin-5-yl)thieno[3,2-d]pyrimidine-7-carboxamide The procedures of <Steps 1, 2 and 3> of Example 1 were repeated in sequence, except for using 4-amino-N,N-dimthylbenzamide instead of 4-chloroaniline in <Step 1> of Example 1 to obtain the title compound (6.7 mg, 2.1%).

$^1$H-NMR Spectrum (300 MHz, DMSO-$d_6$): δ 11.58 (s, 1H), 9.40 (s, 1H), 8.95 (s, 1H), 8.59 (s, 1H), 8.48 (d, 1H), 8.02 (d, 1H), 7.97 (d, 4H), 7.63 (d, 1H), 7.40 (d, 2H), 7.21 (d, 1H), 2.992 (s, 6H), 2.43 (s, 3H)

MS (ESI$^+$, m/z): 498 [M+H]$^+$

Example 96

Preparation of 4-amino-N-(1-((3-acetylaminophenyl)amino)-6-methylisoquinolin-5-yl)thieno[3,2-d]pyrimidine-7-carboxamide The procedures of <Steps 1, 2 and 3> of Example 1 were repeated in sequence, except for using N-(3-aminophenyl)-acetamide instead of 4-chloroaniline in <Step 1> of Example 1 to obtain the title compound (42 mg, 41%).

$^1$H-NMR Spectrum (300 MHz, DMSO-$d_6$): δ 11.59 (brs, 1H), 9.51 (brs, 1H), 8.94 (s, 1H), 5.60 (s, 1H), 8.44 (s, 1H), 8.11 (m, 4H), 7.67 (s, 1H), 7.27 (s, 1H), 7.14 (s, 1H), 2.44 (s, 3H)

MS (ESI$^+$, m/z): 484 [M+H]$^+$

Example 97

Preparation of 4-amino-N-(6-methyl-1-((1-methyl-1H-indazol-6-yl)amino)isoquinolin-5-yl)thieno[3,2-d]pyrimidine-7-carboxamide <Step 1> Preparation of 1-methyl-6-nitro-1H-indazole NaH (1.47 g, 0.037 mol) was added to THF (25 mL) at 0° C. Separately, 6-nitro-1H-indazole (5.0 g, 0.031 mol) was dissolved in THF (25 mL) and the solution was slowly added to the solution prepared. Iodomethane (2.48 mL, 0.040 mol) was slowly added to the mixed solution at the same temperature, followed by stirring for 2 hours. The reaction solution was concentrated under reduced pressure, and added with water and ethyl acetate. The organic layer was washed with a saturated aqueous solution of sodium chloride, dried over anhydrous sodium sulfate, and concentrated under reduced pressure. The concentrated compound (1-methyl added ($R_f$=0.8):2-methyl added ($R_f$=0.3)=1:1) was purified using silica gel chromatography (ethyl acetate: hexane=1:1 (v/v)) to obtain the title compound ($R_f$=0.8, 2.22 g, 41%).

$^1$H-NMR Spectrum (300 MHz, DMSO-$d_6$): δ 8.73 (m, 1H), 8.29 (d, 1H), 8.01 (dd, 1H), 7.94 (dd, 1H), 4.19 (s, 3H)

MS (ESI$^+$, m/z): 177 [M+H]$^+$

<Step 2> Preparation of 1-methyl-1H-indazol-ylamine 1-methyl-6-nitro-1H-indazole obtained in <Step 1> above and Pd/C were added to THF (50 mL), and stirred for 5 hours under hydrogen conditions. The reaction solution was filtered through a Celite pad so as to remove Pd/C, followed by washing with methanol. The organic solvent was concentrated under reduced pressure and purified using silica gel chromatography (dichloromethane:methanol=99:1 (v/v)) to obtain the title compound (1.72 g, 93%).

<Step 3> Preparation of 4-amino-N-(6-methyl-1-((1-methyl-1H-indazol-6-yl)amino)isoquinolin-5-yl)thieno[3,2-d]pyrimidine-7-carboxamide The procedures of <Steps 1, 2 and 3> of Example 1 was repeated in sequence, except for using 1-methyl-1H-indazol-6-ylamine obtained in <Step 2> above instead of 4-chloroaniline in <Step 1> of Example 1 to obtain the title compound (89 mg, 22%).

$^1$H-NMR Spectrum (300 MHz, DMSO-$d_6$): δ 11.56 (s, 1H), 9.38 (s, 1H), 8.94 (s, 1H), 8.57 (s, 1H), 8.52 (d, 1H), 8.35 (s, 1H), 8.04 (d, 1H), 7.95 (br, 2H), 7.91 (s, 1H), 7.64 (m, 2H), 7.53 (m, 1H), 7.19 (d, 1H), 3.98 (s, 3H), 2.42 (s, 3H)

MS (ESI$^+$, m/z): 481 [M+H]$^+$

Example 98

Preparation of 4-amino-N-(6-methyl-1-((4-(methylsulfinyl)phenyl)amino)isoquinolin-5-yl)thieno[3,2-d]pyrimidine-7-carboxamide The procedures of <Step 1> of Example 15 and <Steps 2 and 3> of Example 1 were repeated in sequence, except for using 4-methanesulfonylaniline instead of 4-(trifluoromethyl)pyridine-2-amine in <Step 1> of Example 15 to obtain the title compound (19.5 mg, 6.2%).

$^1$H-NMR Spectrum (300 MHz, DMSO-$d_6$): δ 11.58 (s, 1H), 9.51 (s, 1H), 8.95 (s, 1H), 8.58 (s, 1H), 8.50 (d, 1H), 8.12 (m, 2H), 8.05 (d, 1H), 7.97 (s, 2H), 7.65 (d, 3H), 7.24 (d, 1H), 2.73 (s, 3H), 2.43 (s, 3H)

MS (ESI$^+$, m/z): 489 [M+H]$^+$

Example 99

Preparation of 4-amino-N-(6-methyl-1-((2-methyl-1,3-dioxoisoindolin-5-yl)amino)isoquinolin-5-yl)thieno[3,2-d]pyrimidine-7-carboxamide The procedures of <Steps 1, 2 and 3> of Example 1 were repeated in sequence, except for using 4-amino-N-methylphthalimide instead of 4-chloroaniline in <Step 1> of Example 1 to obtain the title compound (3 mg, 1.2%).

$^1$H-NMR Spectrum (300 MHz, DMSO-$d_6$): δ 11.61 (s, 1H), 9.87 (s, 1H), 8.95 (s, 1H), 8.59 (s, 1H), 8.53 (m, 3H), 8.28 (d, 1H), 8.15 (d, 1H), 7.91 (s, 2H), 7.82 (d, 1H), 7.70 (d, 1H), 3.02 (s, 3H), 2.44 (s, 3H)

MS (ESI$^+$, m/z): 510 [M+H]$^+$

Example 100

Preparation of 4-amino-N-(1-((6-methoxypyridin-3-yl)amino)-6-methylisoquinolin-5-yl)thieno[3,2-d]pyrimidine-7-carboxamide The procedures of <Steps 1, 2 and 3> of Example 1 were repeated in sequence, except for using 5-amino-2-methoxypyridine instead of 4-chloroaniline in <Step 1> of Example 1 to obtain the title compound (75 mg, 9.2%).

$^1$H-NMR Spectrum (300 MHz, DMSO-$d_6$): δ 11.55 (s, 1H), 9.22 (s, 1H), 8.94 (s, 1H), 8.58 (s, 1H), 8.54 (d, 1H), 8.43 (d, 1H), 8.14 (d, 1H), 7.96 (s, 2H), 7.92 (d, 1H), 7.61 (d, 1H), 7.12 (d, 1H), 6.84 (d, 1H), 3.84 (s, 3H), 2.41 (s, 3H)

MS (ESI$^+$, m/z): 458 [M+H]$^+$

Example 101

Preparation of 4-amino-N-(6-methyl-1-((3-(2,2,2-trifluoroacetyl)phenyl)amino)isoquinolin-5-yl)thieno[3,2-d]pyrimidine-7-carboxamide <Step 1> Preparation of 2,2,2-trifluoro-1-(3-nitrophenyl)ethanone 2,2,2-trifluoroacetophenone (0.5 mL, 3.68 mmol) was dissolved in sulfuric acid (3 mL), and added with $NaNO_3$ (0.31 g, 3.68 mmol). The reaction solution was stirred for about 1 hour at 0° C. The reaction mixture was calibrated to yield pH a range of 8 to 9 by adding an aqueous solution of 5 N NaOH. The reaction mixture was diluted with chloroform/2-propanol=4/1 (v/v), and washed with distilled water. The organic layer was dried over anhydrous sodium sulfate, filtered, and concentrated under reduced pressure. The concentrated compound was purified using silica gel chromatography to obtain the title compound (720 mg, 89%).

$^1$H-NMR Spectrum (300 MHz, DMSO-$d_6$): δ 8.29 (s, 1H), 8.24 (d, 1H), 7.96 (d, 1H), 7.69 (t, 1H)

MS (ESI$^+$, m/z): 220 [M+H]$^+$

<Step 2> Preparation of 1-(3-aminophenyl)-2,2,2-trifluoroethanone 2,2,2-trifluoro-1-(3-nitrophenyl)ethanone (0.7 g, 3.26 mmol) obtained in <Step 1> above was dissolved in methanol, followed by stirring. The reaction solution was added with Pd/C (0.09 g, 0.82 mmol), and further stirred under hydrogen conditions for about 12 hours at room temperature. The reaction mixture was filtered through a Celite pad under reduced pressure, and washed with methanol. The filtered solid was dried with warm wind in an oven (40° C.) for 3 hour or more to obtain the title compound (400 mg, 68%).

$^1$H-NMR Spectrum (300 MHz, DMSO-$d_6$): δ 7.02 (t, 1H), 6.97 (s, 1H), 6.56 (m, 2H), 5.15 (s, 2H)

MS (ESI$^+$, m/z): 190 [M+H]$^+$

<Step 3> Preparation of 4-amino-N-(6-methyl-1-((3-(2,2,2-trifluoroacetyl)phenyl)amino)isoquinolin-5-yl)thieno[3,2-d]pyrimidine-7-carboxamide The procedures of <Steps 1, 2 and 3> of Example 1 were repeated in sequence, except for using 1-(3-aminophenyl)-2,2,2-trifluoroethanone obtained in <Step 2> above instead of 4-chloroaniline in <Step 1> of Example 1 to obtain the title compound (19.4 mg, 5%).

$^1$H-NMR Spectrum (300 MHz, DMSO-$d_6$): δ 11.54 (s, 1H), 9.30 (s, 1H), 8.92 (s, 1H), 8.58 (s, 1H), 8.49 (d, 1H), 7.99 (m, 4H), 7.60 (d, 1H), 7.35 (t, 1H), 7.15 (d, 1H), 7.09 (d, 1H), 6.83 (d, 1H), 2.40 (s, 3H)

MS (ESI$^+$, m/z): 523 [M+H]$^+$

Example 102

Preparation of 4-amino-N-(6-methyl-1-((4-propionylphenyl)amino)isoquinolin-5-yl)thieno[3,2-d]pyrimidine-7-carboxamide The procedures of <Steps 1, 2 and 3> of Example 1 were repeated in sequence, except for using 4-aminopropiophenone instead of 4-chloroaniline in <Step 1> of Example 1 to obtain the title compound (72 mg, 23%).

$^1$H-NMR Spectrum (300 MHz, DMSO-$d_6$): δ 11.59 (s, 1H), 9.60 (s, 1H), 8.94 (s, 1H), 8.58 (s, 1H), 8.50 (d, 1H), 8.09 (m, 3H), 7.96 (m, 4H), 7.66 (d, 1H), 7.28 (d, 1H), 3.01 (q, 2H), 2.43 (s, 3H), 1.11 (t, 3H)

MS (ESI$^+$, m/z): 483 [M+H]$^+$

Example 103

Preparation of 4-amino-N-(1-((4-hexanoylphenyl)amino)-6-methylisoquinolin-yl)thieno[3,2-d]pyrimidine-7-carboxamide The procedures of <Steps 1, 2 and 3> of Example 1 were repeated in sequence, except for using 4-aminohexanophenone instead of 4-chloroaniline in <Step 1> of Example 1 to obtain the title compound (10 mg, 6.6%).

$^1$H-NMR Spectrum (300 MHz, DMSO-$d_6$): δ 11.59 (s, 1H), 9.62 (s, 1H), 8.95 (s, 1H), 8.58 (s, 1H), 8.50 (d, 1H), 8.09 (m, 4H), 7.98 (m, 3H), 7.66 (d, 1H), 7.28 (d, 1H), 2.95 (t, 2H), 2.43 (s, 3H), 1.33 (m, 2H), 1.09 (m, 4H), 0.89 (t, 3H)

MS (ESI$^+$, m/z): 525 [M+H]$^+$

Example 104

Preparation of N-(1-((1-acetyl-1H-indazol-6-yl)amino)-6-methylisoquinolin-5-yl)-4-aminothieno[3,2-d]pyrimidine-7-carboxamide <Step 1> Preparation of 1-(6-nitro-1H-indazol-1-yl)ethanone 6-nitroindazole (1 g, 6.13 mmol) was dissolved in dimethylformamide (15 mL), and added with triethylamine (1.7 mL, 12.2 mmol), $Ac_2O$ (0.69 mL, 7.4 mmol) and 18-Crown-6 (0.38 g, 1.23 mmol). The reaction solution was stirred for about 4 hours at room temperature. The reaction mixture was added with distilled water, and further stirred for about 1 hour. The resulting solid was filtered under reduced pressure, and washed with distilled water. The filtered solid was dried with warm wind in an oven (40° C.) for 3 hours or more to obtain the title compound (0.9 g, 75%).

$^1$H-NMR Spectrum (300 MHz, DMSO-$d_6$): δ 9.01 (s, 1H), 8.69 (s, 1H), 8.26 (d, 1H), 8.18 (d, 1H), 2.76 (s, 3H)

MS (ESI$^+$, m/z): 206 [M+H]$^+$

<Step 2> Preparation of 1-(6-amino-1H-indazol-1-yl)ethanone 1-(6-nitro-1H-indazol-1-yl)ethanone obtained in <Step 1> above was dissolved in ethanone (2.2 g, 10.7 mmol), and stirred. The reaction solution was added with Pd/C (0.28 g, 2.68 mmol), followed by stirring under hydrogen conditions for about 12 hours or more at room temperature. The reaction mixture was filtered through a Celite pad under reduced pressure, and washed with methanol. The filtered solid was dried with warm wind in an oven (40° C.) for 3 hours or more to obtain the title compound (1.7 g, 90%).

MS (ESI$^+$, m/z): 176 [M+H]$^+$

<Step 3> Preparation of N-(1-((1-acetyl-1H-indazol-6-yl)amino)-6-methylisoquinolin-5-yl)-4-aminothieno[3,2-d]pyrimidine-7-carboxamide The procedures of <Steps 1, 2 and 3> of Example 1 were repeated in sequence, except for using 1-(6-amino-1H-indazol-1-yl)ethanone obtained in <Step 2> above instead of 4-chloroaniline in <Step 1> of Example 1 to obtain the title compound (21 mg, 13.7%).

$^1$H-NMR Spectrum (300 MHz, DMSO-$d_6$): δ 11.59 (s, 1H), 9.64 (s, 1H), 8.98 (d, 2H), 8.59 (s, 1H), 8.54 (d, 1H), 8.34 (s, 1H), 8.06 (m, 4H), 7.80 (d, 1H), 7.65 (d, 1H), 7.25 (d, 1H), 2.71 (s, 3H), 2.43 (s, 3H)

MS (ESI$^+$, m/z): 509 [M+H]$^+$

Example 105

Preparation of 4-amino-N-(1-((3-chloro-4-fluorophenyl)amino)-6-methylisoquinolin-5-yl)thieno[3,2-d]pyrimidine-7-carboxamide The procedures of <Steps 1, 2 and 3> of Example 1 were repeated in sequence, except for using 3-chloro-4-fluoroaniline instead of 4-chloroaniline in <Step 1> of Example 1 to obtain the title compound (332 mg, 35%).

$^1$H-NMR Spectrum (300 MHz, DMSO-$d_6$): δ 11.56 (s, 1H), 9.37 (s, 1H), 8.85 (s, 1H), 8.58 (s, 1H), 8.45 (d, 1H), 8.27 (dd, 1H), 8.02 (d, 1H), 7.95 (s, 2H), 7.88 (m, 1H), 7.40 (t, 1H), 7.20 (d, 1H), 2.42 (s, 3H)

MS (ESI$^+$, m/z): 479 [M+H]$^+$

Example 106

Preparation of 4-amino-N-(6-methyl-1-((5-oxo-5,6,7,8-tetrahydronaphthalen-2-yl)amino)isoquinolin-5-yl)thieno[3,2-d]pyrimidine-7-carboxamide The procedures of <Steps 1, 2 and 3> of Example 1 were repeated in sequence, except for using 6-amino-3,4-dihydro-2H-naphthalen-1-one instead of 4-chloroaniline in <Step 1> of Example 1 to obtain the title compound (46 mg, 6%).

$^1$H-NMR Spectrum (300 MHz, DMSO-$d_6$): δ 11.58 (s, 1H), 9.55 (s, 1H), 8.93 (s, 1H), 8.70 (s, 1H), 8.47 (d, 1H), 8.08 (d, 1H), 7.94 (m, 3H), 7.84 (m, 2H), 7.64 (d, 1H), 7.26 (d, 1H), 2.90 (t, 3H), 2.49 (t, 3H), 2.42 (s, 3H), 2.02 (m, 3H)

MS (ESI$^+$, m/z): 495 [M+H]$^+$

Example 107

Preparation of 4-amino-N-(6-methyl-1-((2-methyl-2H-indazol-6-yl)amino)isoquinolin-5-yl)thieno[3,2-d]pyrimidine-7-carboxamide The procedures of <Steps 2 and 3> of Example 97 were repeated in sequence, except for using 6-nitro-2H-indazole to obtain methyl-6-nitro-2H-indazole ($R_f$=0.3) instead of 6-nitro-1H-indazole in <Step 1> of Example 97 to obtain the title compound (8 mg, 2.5%).

$^1$H-NMR Spectrum (300 MHz, DMSO-$d_6$): δ 11.55 (s, 1H), 8.93 (s, 1H), 8.57 (s, 1H), 8.50 (d, 1H), 8.27 (s, 1H), 8.20 (s, 1H), 7.98 (m, 1H), 7.95 (s, 1H), 7.60 (m, 2H), 7.41 (d, 1H), 7.14 (d, 1H), 4.10 (s, 3H), 2.41 (s, 3H)

MS (ESI$^+$, m/z): 481 [M+H]$^+$

Example 108

Preparation of methyl 4-((5-(4-aminothieno[3,2-d]pyrimidine-7-carboxamido)-6-methylisoquinolin-1-yl)amino)benzoate The procedures of <Steps 1, 2 and 3> of Example 1 were repeated in sequence, except for using methyl-4-aminobenzoate instead of 4-chloroaniline in <Step 1> of Example 1 to obtain the title compound (95 mg, 136%).

$^1$H-NMR Spectrum (300 MHz, DMSO-$d_6$): δ 11.59 (s, 1H), 9.61 (s, 1H), 9.02 (s, 1H), 8.58 (s, 1H), 8.50 (d, 1H), 8.08 (m, 3H), 7.97 (m, 4H), 7.66 (d, 1H), 7.28 (d, 1H), 3.82 (s, 3H), 2.42 (s, 3H)

MS (ESI$^+$, m/z): 485 [M+H]$^+$

Example 109

Preparation of 4-amino-N-(6-methyl-1-((1-methyl-1H-indazol-5-yl)amino)isoquinolin-5-yl)thieno[3,2-d]pyrimidine-7-carboxamide <Step 1> Preparation of 1-methyl-5-nitro-1H-indazole NaH (1.47 g, 36.8 mmol) was added to THF (40 mL) at 0° C. Separately, 5-nitroindazole (5.0 g, 30.6 mmol) was dissolved in THF (30 mL), and the mixed solution was slowly added to the prepared solution. Iodomethane (2.1 mL, 33.7 mmol) was added to the reaction solution at the same temperature, followed by stirring for 3 hours at room temperature. The reaction solution was concentrated under reduced pressure, and added with water and ethyl acetate. The reaction mixture was added with distilled water for quenching, diluted with ethyl acetate, and washed with distilled water. The organic layer was dried over anhydrous sodium sulfate, and concentrated under reduced pressure. The concentrated compound (1-methyl added ($R_f$=0.3), 2-methyl added ($R_f$=0.1)) was purified using silica gel chromatography (ethyl acetate:hexane=1:1 (v/v)) to obtain the title compound ($R_f$=0.3, 2.29 g, 42%).

$^1$H-NMR Spectrum (300 MHz, DMSO-$d_6$): δ 8.74 (d, 1H), 8.31 (dd, 1H), 8.20 (s, 1H), 7.47 (d, 1H), 4.15 (s, 3H)

MS (ESI$^+$, m/z): 178 [M+H]$^+$

<Step 2> Preparation of 1-methyl-1H-indazol-5-amine

Iron (3.62 g, 64.7 mmol) and concentrated hydrochloric acid (0.1 mL) were added to ethanol/water (20 mL/20 mL), and refluxed for 1 hour. The mixed reaction solution was added with 1-methyl-5-nitro-1H-indazole (2.29 g, 12.9 mmol) obtained in <Step 1> above, and further refluxed for 3 hours or more. The reaction mixture was filtered through a Celite pad under reduced pressure, and washed with chloroform/2-propanol=4/1(v/v). The filtrate obtained was distilled under reduced pressure, and dissolved in chloroform/2-propanol=4/1 (v/v). The organic layer was washed with an aqueous solution of sodium bicarbonate and brine. The obtained organic layer was dried over anhydrous sodium sulfate, filtered, and concentrated under reduced pressure to obtain the title compound (1.35 g, 71%).

$^1$H-NMR Spectrum (300 MHz, DMSO-$d_6$): δ 7.65 (d, 1H), 7.31 (d, 1H), 6.80 (d, 1H), 6.71 (d, 1H), 4.78 (s, 2H), 3.89 (s, 3H)

MS (ESI$^+$, m/z): 148 [M+H]$^+$

<Step 3> Preparation of 4-amino-N-(6-methyl-1-((1-methyl-1H-indazol-5-yl)amino)isoquinolin-5-yl)thieno[3,2-d]pyrimidine-7-carboxamide The procedures of <Steps 1, 2 and 3> of Example 1 were repeated in sequence, except for using 1-methyl-1H-indazol-5-amine obtained in <Step 2> above instead of 4-chloroaniline in <Step 1> of Example 1 to obtain the title compound (15 mg, 6.3%).

$^1$H-NMR Spectrum (300 MHz, DMSO-$d_6$): δ 11.54 (s, 1H), 9.23 (s, 1H), 8.84 (s, 1H), 8.57 (s, 1H), 8.49 (d, 1H), 8.31 (s, 1H), 7.98 (m, 4H), 7.74 (d, 1H), 7.60 (d, 1H), 7.10 (d, 1H), 4.00 (s, 3H), 2.40 (s, 3H)

MS (ESI$^+$, m/z): 481 [M+H]$^+$

Example 110

Preparation of 4-amino-N-(6-methyl-1-((2-methyl-2H-indazol-5-yl)amino)isoquinolin-5-yl)thieno[3,2-d]pyrimidine-7-carboxamide <Step 1> Preparation of 2-methyl-5-nitro-2H-indazole The procedures of <Step 1> of Example 109 were repeated to obtain the title compound ($R_f$=0.1, 1.51 g, 28%).

$^1$H-NMR Spectrum (300 MHz, DMSO-$d_6$): δ 8.73 (d, 1H), 8.20 (s, 1H), 8.09 (dd, 1H), 7.74 (d, 1H), 4.29 (s, 3H)
MS (ESI$^+$, m/z): 178 [M+H]$^+$ <Step 2> Preparation of 2-methyl-2H-indazol-5-amine The procedures of <Step 2> of Example 109 were repeated to obtain the title compound (0.6 g, 48%).
$^1$H-NMR Spectrum (300 MHz, DMSO-$d_6$): δ 7.82 (s, 1H), 7.51 (d, 1H), 6.72 (dd, 1H), 6.53 (d, 1H), 4.74 (s, 2H), 4.01 (s, 3H)
MS (ESI$^+$, m/z): 148 [M+H]$^+$ <Step 3> Preparation of 4-amino-N-(6-methyl-1-((2-methyl-2H-indazol-5-yl)amino)isoquinolin-5-yl) thieno[3,2-d]pyrimidine-7-carboxamide The procedures of <Steps 1, 2 and 3> of Example 1 were repeated in sequence, except for using 2-methyl-2H-indazol-5-amine obtained in <Step 2> above instead of 4-chloroaniline in <Step 1> of Example 1 to obtain the title compound (24.2 mg, 10%).
$^1$H-NMR Spectrum (300 MHz, DMSO-$d_6$): δ 11.54 (s, 1H), 9.47 (s, 1H), 8.93 (s, 1H), 8.49 (s, 1H), 8.46 (d, 1H), 8.31 (s, 1H), 7.98 (m, 3H), 7.74 (d, 1H), 7.60 (m, 2H), 7.10 (d, 1H), 4.02 (s, 3H), 2.40 (s, 3H)
MS (ESI$^+$, m/z): 481 [M+H]$^+$ Example 111

Preparation of 4-amino-N-(6-methyl-1-((6-methylpyridin-3-yl)amino)isoquinolin-5-yl)thieno[3,2-d] pyrimidine-7-carboxamide The procedures of <Step 1> of Example 15 and <Steps 2 and 3> of Example 1 were repeated in sequence, except for using 5-amino-2-methylpyridine instead of aniline in <Step 1> of Example 15 to obtain the title compound (5 mg, 3%).
$^1$H-NMR Spectrum (300 MHz, DMSO-$d_6$): δ 11.61 (s, 1H), 9.34 (s, 1H), 8.98 (s, 1H), 8.90 (s, 1H), 8.62 (s, 1H), 8.51 (d, 1H), 8.27 (m, 1H), 8.02 (m, 3H), 7.68 (d, 1H), 7.27 (m, 2H), 2.54 (s, 3H), 2.48 (s, 3H)
MS (ESI$^+$, m/z): 442 [M+H]$^+$ Example 112

Preparation of 4-amino-N-(6-methyl-1-((1-methyl-1H-indol-6-yl)amino)isoquinolin-5-yl)thieno[3,2-d] pyrimidine-7-carboxamide <Step 1> Preparation of 1-methyl-1H-indol-6-ylamine The procedures of <Step 1> of Example 97 were repeated, except for using 1H-indol-6-ylamine instead of 6-nitro-1H-indazole in <Step 1> of Example 97 to obtain the title compound (151 mg, 33%).

<Step 2> Preparation of 4-amino-N-(6-methyl-1-((1-methyl-1H-indol-6-yl)amino)isoquinolin-5-yl) thieno[3,2-d]pyrimidine-7-carboxamide The procedures of <Steps 1, 2 and 3> of Example 1 were repeated in sequence, except for using 1-methyl-1H-indol-6-ylamine obtained in <Step 1> above instead of 4-chloroaniline in <Step 1> of Example 1 to obtain the title compound (65 mg, 31%).
$^1$H-NMR Spectrum (300 MHz, DMSO-$d_6$): δ 11.53 (s, 1H), 9.21 (br, 1H), 8.93 (s, 1H), 8.57 (s, 1H), 8.49 (d, 1H), 8.02 (s, 1H), 7.95-7.92 (m, 3H), 7.58 (d, 1H), 7.44 (m, 2H), 7.23 (d, 1H), 7.07 (d, 1H), 6.35 (d, 1H), 3.75 (s, 3H), 2.40 (s, 3H)
MS (ESI$^+$, m/z): 480 [M+H]$^+$ Example 113

Preparation of tert-butyl 6-((5-(4-aminothieno[3,2-d]pyrimidine-7-carboxamido)-6-methylisoquinolin-1-yl)amino)-1H-indazol-1-carboxylate <Step 1> Preparation of (1H-indazol-6-yl)-(6-methyl-5-nitro-isoquinolin-1-yl)-amine The procedures of <Step 1> of Example 1 were repeated, except for using 1H-indazol-6-amine instead of 4-chloroaniline in <Step 1> of Example 1 to obtain the title compound (639 mg, 68%).
$^1$H-NMR Spectrum (300 MHz, DMSO-$d_6$): δ 9.01 (d, 1H), 8.12 (s, 1H), 8.01 (s, 1H), 7.88 (d, 2H), 7.79 (d, 1H), 7.33 (d, 1H), 6.93 (d, 1H), 2.52 (s, 3H)
MS (ESI$^+$, m/z): 319 [M+H]$^+$ <Step 2> Preparation of 6-(6-methyl-5-nitro-isoquinolin-1-ylamino)-indazol-1-carboxylic acid tert-butyl ester (1H-indazol-6-yl)-(6-methyl-5-nitro-isoquinolin-1-yl)-amine (300 mg, 0.942 mmol) obtained in <Step 1> above, triethylamine (0.131 mL, 0.942 mmol) and DMAP (58 mg, 0.471 mmol) were dissolved in $CH_2Cl_2$ (10 mL), and slowly added with di-tert-butyl dicarbonate (0.216 mL, 0.942 mmol) at 0° C. The reaction solution was stirred for 3 hour at room temperature, diluted with ethyl acetate, and washed with a saturated aqueous solution of sodium bicarbonate and brine. The organic layer was dried over anhydrous sodium sulfate, filtered, and concentrated under reduced pressure to obtain the title compound (395 mg, 99%).
MS (ESI$^+$, m/z): 419 [M+H]$^+$ <Step 3> Preparation of tert-butyl 6-((5-(4-aminothieno[3,2-d]pyrimidine-7-carboxamido)-6-methylisoquinolin-1-yl)amino)-1H-indazol-1-carboxylate The procedures of <Steps 2 and 3> of Example 1 were repeated in sequence, except for using 6-(6-methyl-5-nitroisoquinolin-1-ylamino)-indazol-1-carboxylic acid tert-butyl ester obtained in <Step 2> above instead of N-(4-chlorophenyl)-6-methyl-5-nitroisoquinolin-1-amine in <Step 2> of Example 1 to obtain the title compound (130 mg, 30%).
MS (ESI$^+$, m/z): 566 [M+H]$^+$ Example 114

Preparation of N-(1-((1H-indazol-6-yl)amino)-6-methylisoquinolin-5-yl)-4-aminothieno[3,2-d]pyrimidine-7-carboxamide hydrochloride tert-butyl 6-((5-(4-aminothieno[3,2-d]pyrimidine-7-carboxamido)-6-methylisoquinolin-1-yl)amino)-1H-indazol-1-carboxylate (50 mg, 0.088 mmol) obtained in Example 113 was dissolved in ethyl acetate (5 mL), and added with 4 M HCl (dioxane solution, 0.5 mL). The reaction solution was stirred for 5 hours, and then the filtrate was filtered to obtain the title compound (40 mg, 90%).

MS (ESI$^+$, m/z): 467 [M+H]$^+$

Example 115

Preparation of 4-amino-N-(1-((5-chloro-2-fluorophenyl)amino)-6-methylisoquinolin-5-yl)thieno[3,2-d]pyrimidine-7-carboxamide The procedures of <Steps 1, 2 and 3> of Example 1 were repeated in sequence, except for using 5-chloro-2-fluoroaniline instead of 4-chloroaniline in <Step 1> of Example 1 to obtain the title compound (380 mg, 6%).

$^1$H-NMR Spectrum (300 MHz, DMSO-$d_6$): δ 11.55 (s, 1H), 9.14 (s, 1H), 8.93 (s, 1H), 8.56 (s, 1H), 8.32 (m, 1H), 7.92 (m, 3H), 7.77 (dd, 1H), 7.61 (d, 1H), 7.30 (t, 1H), 7.20 (m, 2H), 2.41 (m, 3H)

MS (ESI$^+$, m/z): 479 [M+H]$^+$

Example 116

Preparation of 4-amino-N-(1-((3-chloro-2-fluorophenyl)amino)-6-methylisoquinolin-5-yl)thieno[3,2-d]pyrimidine-7-carboxamide The procedures of <Steps 1, 2 and 3> of Example 1 were repeated in sequence, except for using 3-chloro-2-fluoroaniline instead of 4-chloroaniline in <Step 1> of Example 1 to obtain the title compound (10 mg, 6.3%).

$^1$H-NMR Spectrum (300 MHz, DMSO-$d_6$): δ 11.56 (s, 1H), 9.24 (s, 1H), 8.93 (s, 1H), 8.57 (s, 1H), 8.36 (d, 1H), 7.95 (s, 2H), 7.90 (d, 1H), 7.63 (d, 1H), 7.57 (t, 1H), 7.37 (t, 1H), 7.24 (m, 2H), 2.42 (s, 3H)

MS (ESI$^+$, m/z): 479 [M+H]$^+$

Example 117

Preparation of 4-amino-N-(1-((3-fluoro-4-(4-methylpiperazin-1-yl)phenyl)amino)-6-methylisoquinolin-5-yl)thieno[3,2-d]pyrimidine-7-carboxamide The procedures of <Steps 1, 2 and 3> of Example 1 were repeated in sequence, except for using 3-fluoro-4-(4-methylpiperazin-1-yl)aniline instead of 4-chloroaniline in <Step 1> of Example 1 to obtain the title compound (20 mg, 16%).

$^1$H-NMR Spectrum (300 MHz, DMSO-$d_6$): δ 11.53 (s, 1H), 9.19 (s, 1H), 8.92 (s, 1H), 8.57 (s, 1H), 8.43 (d, 1H), 7.98-7.85 (m, 4H), 7.59 (d, 1H), 7.54 (dd, 1H), 7.12 (d, 1H), 7.00 (t, 1H), 3.31 (m, 4H), 2.96 (m, 4H), 2.40 (s, 3H), 2.21 (s, 3H)

MS (ESI$^+$, m/z): 543 [M+H]$^+$

Example 118

Preparation of 4-amino-N-(1-((3-chloro-1-methyl-1H-indazol-6-yl)amino)-6-methylisoquinolin-5-yl)thieno[3,2-d]pyrimidine-7-carboxamide The procedures of <Steps 1, 2 and 3> of Example 1 were repeated in sequence, except for using 3-chloro-1-methyl-1H-indazol-6-amine instead of 4-chloroaniline in <Step 1> of Example 1 to obtain the title compound (143 mg, 16%).

$^1$H-NMR Spectrum (300 MHz, DMSO-$d_6$): δ 11.57 (s, 1H), 9.48 (s, 1H), 8.93 (s, 1H), 8.57 (s, 1H), 8.52 (d, 1H), 8.44 (s, 1H), 8.08 (d, 1H), 7.94 (s, 2H), 7.63 (m, 2H), 7.56 (d, 1H), 7.22 (d, 1H), 3.95 (s, 3H), 2.42 (s, 3H)

MS (ESI$^+$, m/z): 515 [M+H]$^+$

Example 119

Preparation of 4-amino-N-(6-methyl-1-((4-(prop-2-yn-1-yloxy)phenyl)amino)isoquinolin-5-yl)thieno[3,2-d]pyrimidine-7-carboxamide The procedures of <Steps 1, 2 and 3> of Example 1 were repeated in sequence, except for using 4-(2-propyn-1-yloxy)aniline instead of 4-chloroaniline in <Step 1> of Example 1 to obtain the title compound (22 mg, 9.3%).

$^1$H-NMR Spectrum (300 MHz, DMSO-$d_6$): δ 11.53 (s, 1H), 9.10 (s, 1H), 8.93 (s, 1H), 8.57 (s, 1H), 8.44 (d, 1H), 7.94 (m, 3H), 7.76 (d, 1H), 7.58 (d, 1H), 7.09 (d, 1H), 6.98 (d, 1H), 4.77 (d, 2H), 3.55 (t, 1H), 2.40 (s, 3H)

MS (ESI$^+$, m/z): 481 [M+H]$^+$

Example 120

Preparation of 4-amino-N-(1-((2-methoxy-4-morpholinophenyl)amino)-6-methylisoquinolin-5-yl)thieno[3,2-d]pyrimidine-7-carboxamide The procedures of <Steps 1, 2 and 3> of Example 1 were repeated in sequence, except for using 2-methoxy-4-morpholinoaniline instead of 4-chloroaniline in <Step 1> of Example 1 to obtain the title compound (29 mg, 6.5%).

$^1$H-NMR Spectrum (300 MHz, DMSO-$d_6$): δ 11.50 (s, 1H), 8.93 (s, 1H), 8.57 (s, 1H), 8.42 (s, 1H), 8.30 (d, 1H), 7.94 (s, 2H), 7.67 (m, 2H), 6.99 (d, 1H), 6.67 (d, 1H), 6.48 (d, 1H), 3.78 (m, 7H), 3.12 (m, 4H), 2.40 (s, 3H)

MS (ESI$^+$, m/z): 542 [M+H]$^+$

Example 121

Preparation of 4-amino-N-(1-(benzo[d]thiazol-6-ylamino)-6-methylisoquinolin-5-yl)thieno[3,2-d]pyrimidine-7-carboxamide The procedures of <Steps 1, 2 and 3> of Example 1 were repeated in sequence, except for using 6-aminobenzothiazole instead of 4-chloroaniline in <Step 1> of Example 1 to obtain the title compound (37 mg, 15.7%).

$^1$H-NMR Spectrum (300 MHz, DMSO-$d_6$): δ 11.57 (s, 1H), 9.47 (s, 1H), 9.21 (s, 1H), 8.94 (s, 1H), 8.85 (s, 1H), 8.58 (s, 1H), 8.50 (d, 1H), 8.05 (m, 2H), 8.01 (s, 1H), 7.94 (m, 2H), 7.65 (d, 1H), 7.21 (d, 1H), 2.43 (s, 3H)

MS (ESI$^+$, m/z): 484 [M+H]$^+$

Example 122

Preparation of N-(1-((1H-indazol-5-yl)amino)-6-methylisoquinolin-5-yl)-4-aminothieno[3,2-d]pyrimidine-7-carboxamide hydrochloride The procedures of <Steps 1, 2 and 3> of Example 113 and Example 114 were repeated in sequence, except for using 1H-indazol-5-amine instead of 1H-indazol-6-amine in <Step 1> of Example 113 to obtain the title compound (5 mg, 5%).

MS (ESI$^+$, m/z): 466 [M+H]$^+$

Example 123

Preparation of 4-amino-N-(1-((3-chloro-2,4-difluorophenyl)amino)-6-methylisoquinolin-5-yl)thieno[3,2-d]pyrimidine-7-carboxamide The procedures of <Steps 1, 2 and 3> of Example 1 were repeated in sequence, except for using 3-chloro-2,4-difluoroaniline instead of 4-chloroaniline in <Step 1> of Example 1 to obtain the title compound (95 mg, 6%).

$^1$H-NMR Spectrum (300 MHz, DMSO-$d_6$): δ 11.51 (s, 1H), 8.93 (s, 1H), 8.57 (s, 1H), 8.34 (d, 1H), 7.94 (s, 2H), 7.87 (d, 1H), 7.63 (m, 2H), 7.37 (m, 1H), 7.14 (d, 1H), 2.43 (s, 3H)

MS (ESI$^+$, m/z): 515 [M+H]$^+$

Example 124

Preparation of 4-amino-N-(1-((3-(dimethylamino)propyl)amino)-6-methylisoquinolin-5-yl)thieno[3,2-d]pyrimidine-7-carboxamide The procedures of <Steps 1, 2 and 3> of Example 1 were repeated in sequence, except for using N1,N1-dimethylpropan-1,3-diamine instead of 4-chloroaniline in <Step 1> of Example 1 to obtain the title compound (25 mg, 8%).

$^1$H-NMR Spectrum (300 MHz, DMSO-$d_6$): δ 11.46 (s, 1H), 8.90 (s, 1H), 8.55 (s, 1H), 8.11 (d, 1H), 7.92 (s, 2H), 7.84 (d, 1H), 7.60 (m, 1H), 7.47 (d, 1H), 6.87 (d, 1H), 3.62 (m, 2H), 2.87 (m, 2H), 2.67 (s, 3H), 2.58 (s, 6H), 1.89 (m, 2H)

MS (ESI$^+$, m/z): 436 [M+H]$^+$

Example 125

Preparation of 4-amino-N-(6-methyl-1-(piperidin-1-yl)isoquinolin-5-yl)thieno[3,2-d]pyrimidine-7-carboxamide The procedures of <Steps 1, 2 and 3> of Example 1 were repeated in sequence, except for using piperidine instead of 4-chloroaniline in <Step 1> of Example 1 to obtain the title compound (8 mg, 2%).

$^1$H-NMR Spectrum (300 MHz, DMSO-$d_6$): δ 11.42 (s, 1H), 9.10 (s, 1H), 8.62 (s, 1H), 8.05 (m, 3H), 7.93 (s, 1H), 7.54 (m, 1H), 7.30 (d, 1H), 3.21 (m, 4H), 2.48 (s, 3H), 1.77 (m, 4H), 1.64 (m, 2H)

MS (ESI$^+$, m/z): 419 [M+H]$^+$

The compounds obtained in Examples 1 to 125 are represented by the following structural formula, as shown in Table 1 below.

TABLE 1

| Ex. | Name | Formula |
|---|---|---|
| 1 | 4-amino-N-(1-((4-chlorophenyl)amino)-6-methylisoquinolin-5-yl)thieno[3,2-d]pyrimidine-7-carboxamide | 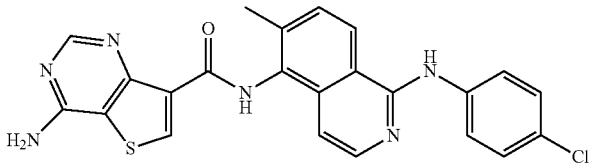 |
| 2 | 4-amino-N-(6-methyl-1-((3-(trifluoromethyl)phenyl)amino)isoquinolin-5-yl)thieno[3,2-d]pyrimidine-7-carboxamide | 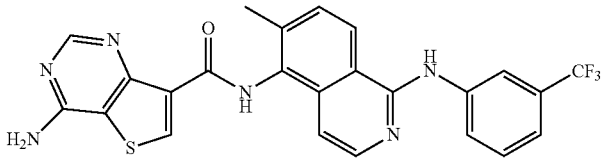 |
| 3 | N-(1-((4-chlorophenyl)amino)-6-methylisoquinolin-5-yl)-4-(cyclopropylamino)thieno[3,2-d]pyrimidine-7-carboxamide | 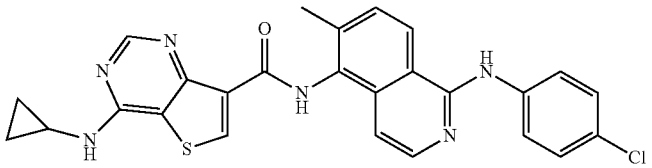 |
| 4 | 4-(cyclopropylamino)-N-(6-methyl-1-((3-(trifluoromethyl)phenyl)amino)isoquinolin-5-yl)thieno[3,2-d]pyrimidine-7-carboxamide | 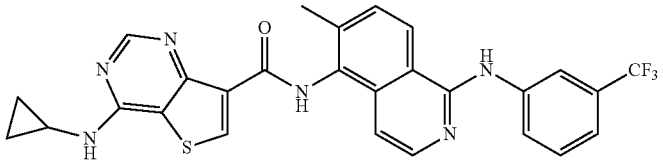 |

TABLE 1-continued

| Ex. | Name | Formula |
|---|---|---|
| 5 | 4-amino-N-(6-methyl-1-((3-(4-methyl-1H-imidazol-1-yl)-5-(trifluoromethyl)phenyl)amino)isoquinolin-5-yl)thieno[3,2-d]pyrimidine-7-carboxamide | 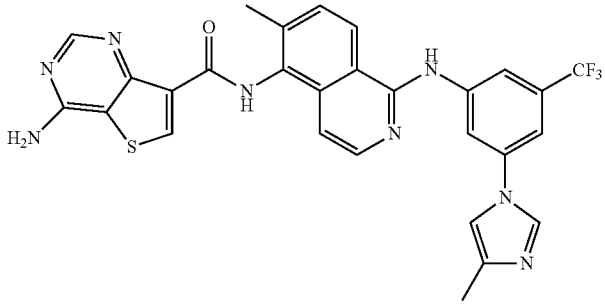 |
| 6 | 4-(cyclopropylamino)-N-(6 methyl-1-((3-(4-methyl-1H-imidazol-1-yl)-5-(trifluoromethyl)phenyl)amino)isoquinolin-5-yl)thieno[3,2-d]pyrimidine-7-carboxamide | 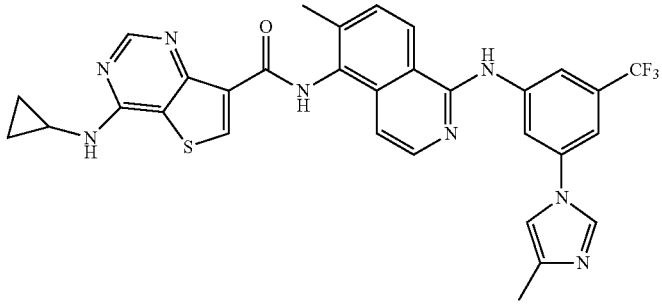 |
| 7 | 4-amino-N-(1-((4-((4-ethylpiperazin-1-yl)methyl)-3-(trifluoromethyl)phenyl)amino)-6-methylisoquinolin-5-yl)thieno[3,2-d]pyrimidine-7-carboxamide | 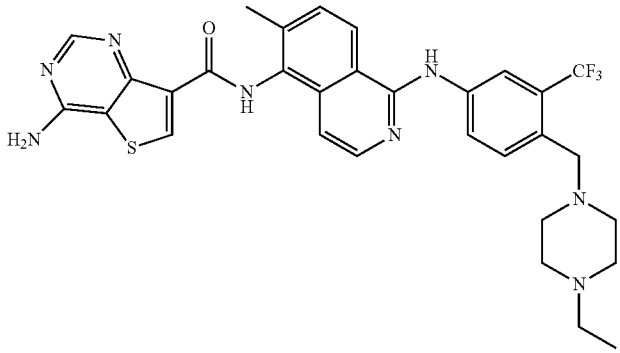 |
| 8 | 4-(cyclopropylamino)-N-(1-((4-((4-ethylpiperazin-1-yl)methyl)-3-(trifluoromethyl)phenyl)amino)-6-methylisoquinolin-5-yl)thieno[3,2-d]pyrimidine-7-carboxamide | 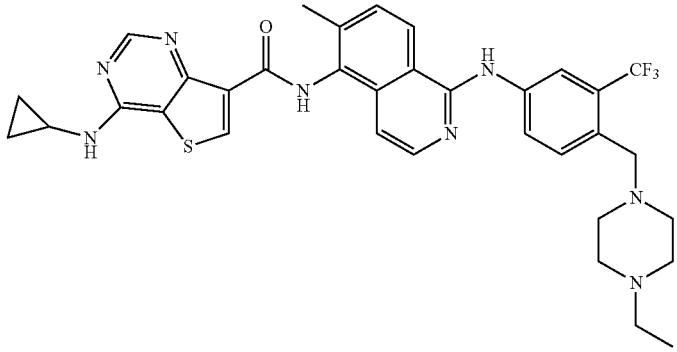 |

TABLE 1-continued

| Ex. | Name | Formula |
|---|---|---|
| 9 | N-(1-((4-((4-ethylpiperazin-1-yl)methyl)-3-(trifluoromethyl)phenyl)amino)-6-methylisoquinolin-5-yl)-4-(methylamino)thieno[3,2-d]pyrimidine-7-carboxamide | 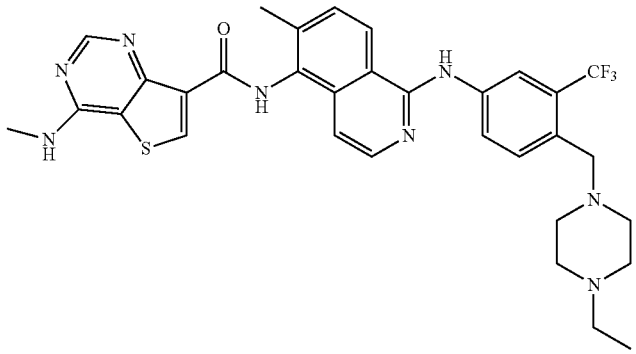 |
| 10 | 4-amino-N-(1-((4-(4-ethylpiperazin-1-yl)phenyl)amino)-6-methylisoquinolin-5-yl)thieno[3,2-d]pyrimidine-7-carboxamide | 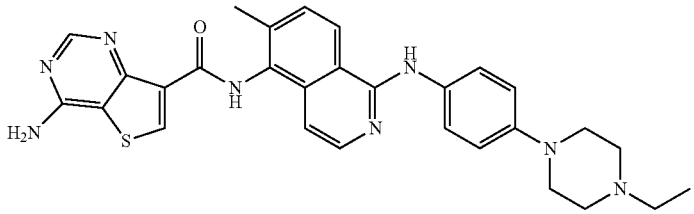 |
| 11 | 4-amino-N-(1-((4-((4-ethylpiperazin-1-yl)methyl)phenyl)amino)-6-methylisoquinolin-5-yl)thieno[3,2-d]pyrimidine-7-carboxamide | 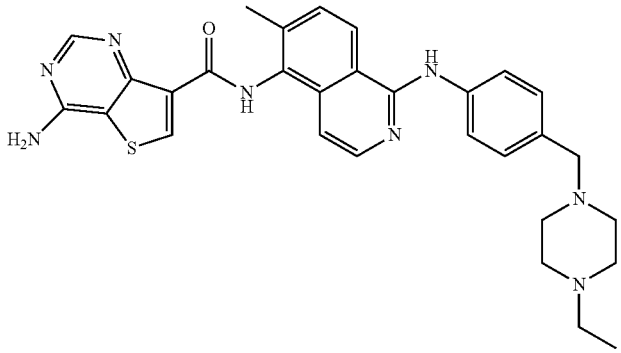 |
| 12 | 4-amino-N-(6-methyl-1-(phenylamino)isoquinolin-5-yl)thieno[3,2-d]pyrimidine-7-carboxamide | 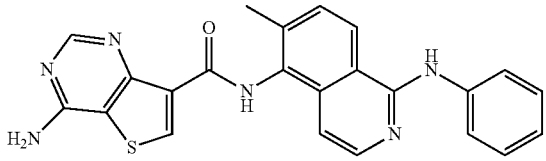 |
| 13 | 4-amino-N-(1-((4-chloro-3-(trifluoromethyl)phenyl)amino)-6-methylisoquinolin-5-yl)thieno[3,2-d]pyrimidine-7-carboxamide | 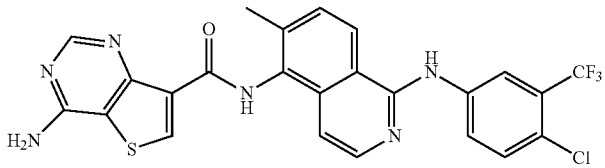 |
| 14 | 4-amino-N-(1-((2-methoxy-5-(trifluoromethyl)phenyl)amino)-6-methylisoquinolin-5-yl)thieno[3,2-d]pyrimidine-7-carboxamide | 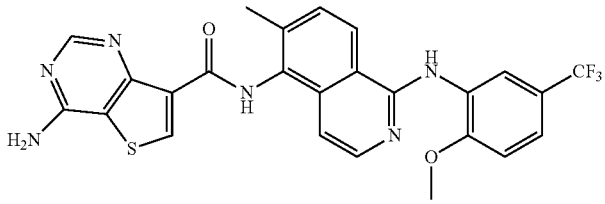 |

TABLE 1-continued

| Ex. | Name | Formula |
|---|---|---|
| 15 | 4-amino-N-(6-methyl-1-((4-(trifluoromethyl)phenyl)amino)isoquinolin-5-yl)thieno[3,2-d]pyrimidine-7-carboxamide | 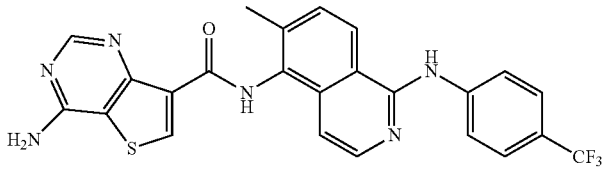 |
| 16 | 4-amino-N-(1-((4-methoxyphenyl)amino)-6-methylisoquinolin-5-yl)thieno[3,2-d]pyrimidine-7-carboxamide | 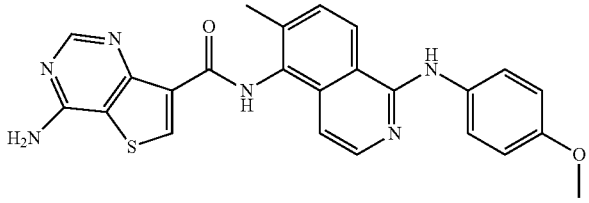 |
| 17 | 4-amino-N-(6-methyl-1-(p-tolylamino)isoquinolin-5-yl)thieno[3,2-d]pyrimidine-7-carboxamide | 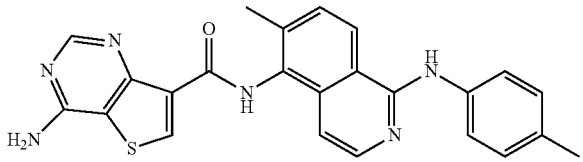 |
| 18 | 4-amino-N-(1-((4-isopropylphenyl)amino)-6-methylisoquinolin-5-yl)thieno[3,2-d]pyrimidine-7-carboxamide | 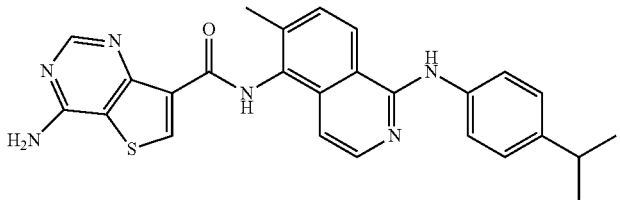 |
| 19 | 4-amino-N-(1-((5-(t-butyl)isoxazol-3-yl)amino)-6-methylisoquinolin-5-yl)thieno[3,2-d]pyrimidine-7-carboxamide | 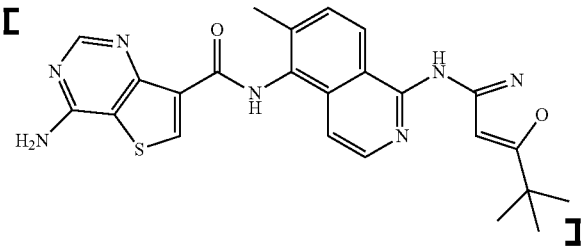 |
| | | 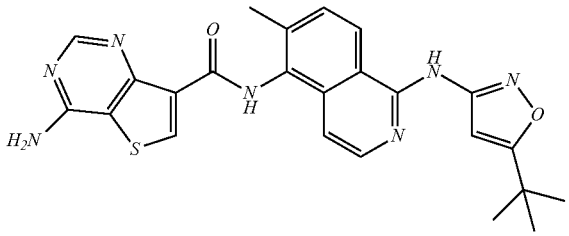 |
| 20 | 4-amino-N-(1-((4-fluorophenyl)amino)-6-methylisoquinolin-5-yl)thieno[3,2-d]pyrimidine-7-carboxamide | 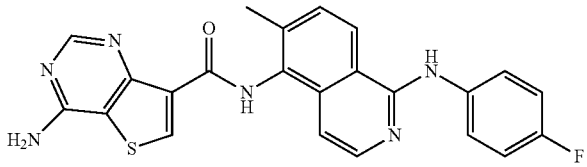 |

TABLE 1-continued

| Ex. | Name | Formula |
|---|---|---|
| 21 | 4-amino-N-(6-methyl-1-(thiazol-2-ylamino)isoquinolin-5-yl)thieno[3,2-d]pyrimidine-7-carboxamide | 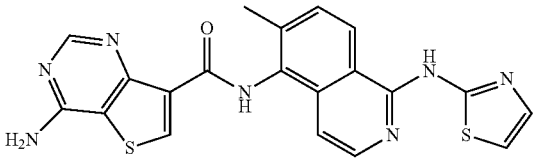 |
| 22 | 4-amino-N-(1-((4-cyanophenyl)amino)-6-methylisoquinolin-5-yl)thieno[3,2-d]pyrimidine-7-carboxamide | 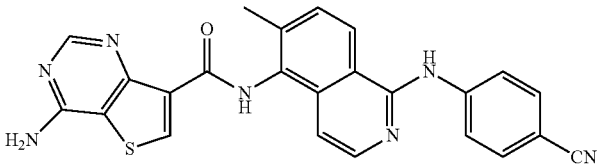 |
| 23 | 4-amino-N-(6-methyl-1-(quinolin-5-ylamino)isoquinolin-5-yl)thieno[3,2-d]pyrimidine-7-carboxamide | 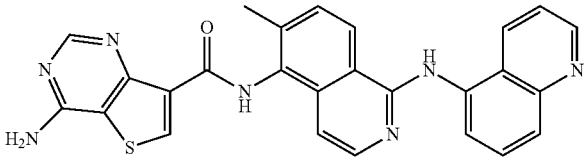 |
| 24 | 4-amino-N-(1-((4-ethoxyphenyl)amino)-6-methylisoquinolin-5-yl)thieno[3,2-d]pyrimidine-7-carboxamide | 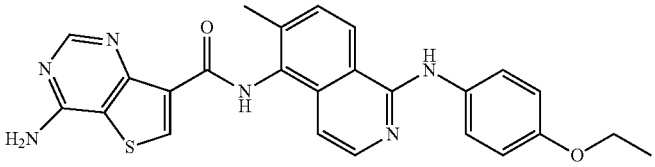 |
| 25 | 4-amino-N-(6-methyl-1-((4-phenoxyphenyl)amino)isoquinolin-5-yl)thieno[3,2-d]pyrimidine-7-carboxamide | 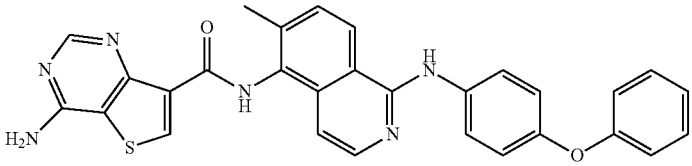 |
| 26 | 4-amino-N-(1-((4-hydroxyphenyl)amino)-6-methylisoquinolin-5-yl)thieno[3,2-d]pyrimidine-7-carboxamide | 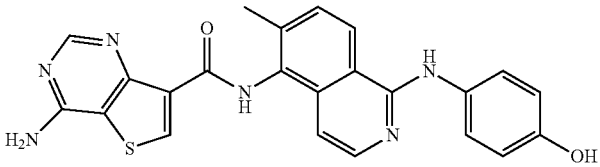 |
| 27 | 4-amino-N-(1-((4-isopropoxyphenyl)amino)-6-methylisoquinolin-5-yl)thieno[3,2-d]pyrimidine-7-carboxamide | 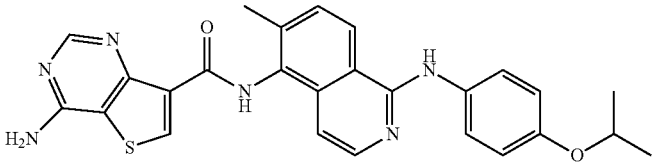 |
| 28 | Preparation of 4-amino-N-(1-((4-(dimethylaminophenyl)amino)-6-methylisoquinolin-5-yl)thieno[3,2-d]pyrimidine-7-carboxamide [4-amino-N-(1-((4-(dimethylamino)-6-methylisoquinolin-5-yl)thieno[3,2-d]-pyrimidine-7-carboxamide] | 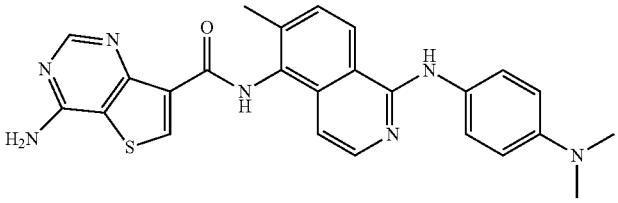 |
| 29 | 4-amino-N-(1-((2,3-dihydrobenzo[b][1,4]dioxin-6-yl)amino)-6-methylisoquinolin-5-yl)thieno[3,2-d]pyrimidine-7-carboxamide | 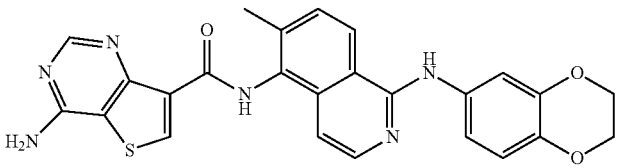 |

TABLE 1-continued

| Ex. | Name | Formula |
|---|---|---|
| 30 | 4-amino-N-(1-((3,4-dimethoxyphenyl)amino)-6-methylisoquinolin-5-yl)thieno[3,2-d]pyrimidine-7-carboxamide | 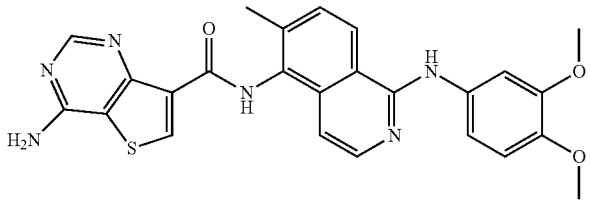 |
| 31 | 4-amino-N-(1-((3-fluoro-4-methoxyphenyl)amino)-6-methylisoquinolin-5-yl)thieno[3,2-d]pyrimidine-7-carboxamide | 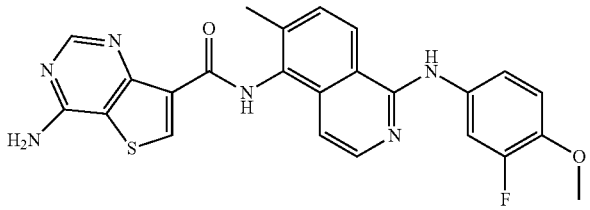 |
| 32 | 4-amino-N-(6-methyl-1-((3,4,5-trimethoxyphenyl)amino)isoquinolin-5-yl)thieno[3,2-d]pyrimidine-7-carboxamide | 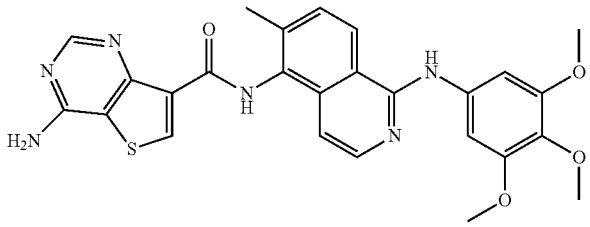 |
| 33 | 4-amino-N-(6-methylisoquinolin-5-yl)thieno[3,2-d]pyrimidine-7-carboxamide | 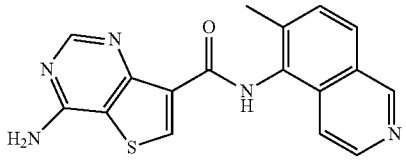 |
| 34 | 4-amino-N-(1-(benzo[d][1,3]dioxol-5-ylamino)-6-methylisoquinolin-5-yl)thieno[3,2-d]pyrimidine-7-carboxamide | 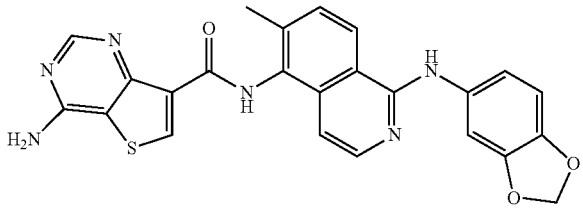 |
| 35 | 4-amino-N-(6-methyl-1-((5,6,7,8-tetrahydronaphthalen-2-yl)amino)isoquinolin-5-yl)thieno[3,2-d]pyrimidine-7-carboxamide | 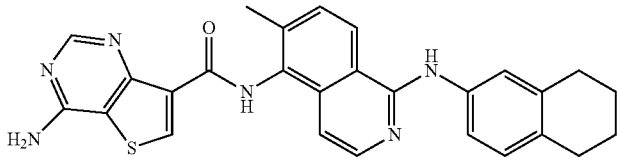 |
| 36 | 4-amino-N-(4-((4-chlorophenyl)amino)-7-methylquinazolin-8-yl)thieno[3,2-d]pyrimidine-7-carboxamide | 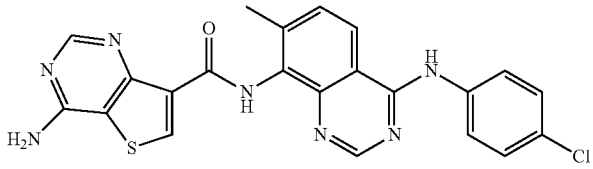 |

TABLE 1-continued

| Ex. | Name | Formula |
|---|---|---|
| 37 | 4-(cyclopropylamino)-N-(1-((4-methoxyphenyl)amino)-6-methylisoquinolin-5-yl)thieno[3,2-d]pyrimidine-7-carboxamide | 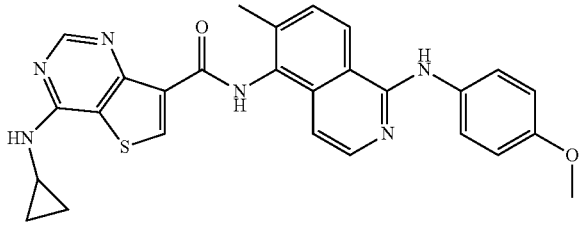 |
| 38 | 4-amino-N-(1-((3-chlorophenyl)amino)-6-methylisoquinolin-5-yl)thieno[3,2-d]pyrimidine-7-carboxamide | 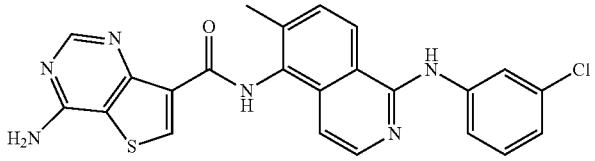 |
| 39 | 4-amino-N-(1-((3-bromophenyl)amino)-6-methylisoquinolin-5-yl)thieno[3,2-d]pyrimidine-7-carboxamide | 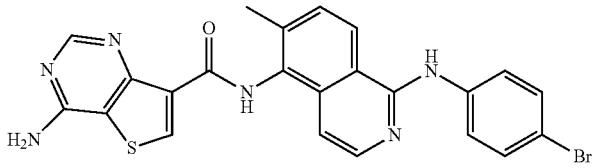 |
| 40 | 4-amino-N-(1-((2,4-dichlorophenyl)amino)-6-methylisoquinolin-5-yl)thieno[3,2-d]pyrimidine-7-carboxamide | 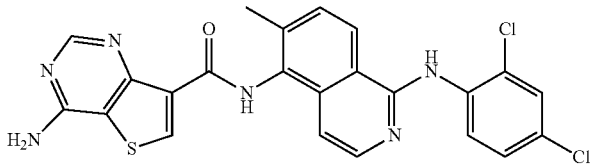 |
| 41 | 4-amino-N-(1-((3,4-dichlorophenyl)amino)-6-methylisoquinolin-5-yl)thieno[3,2-d]pyrimidine-7-carboxamide | 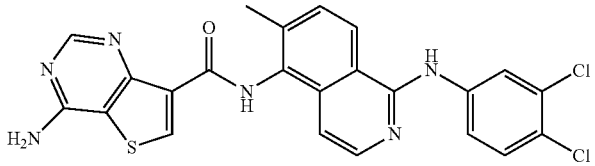 |
| 42 | 4-amino-N-(1-((3,5-dichlorophenyl)amino)-6-methylisoquinolin-5-yl)thieno[3,2-d]pyrimidine-7-carboxamide | 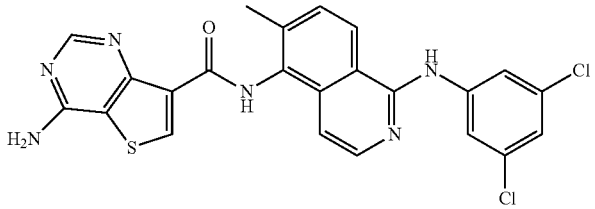 |
| 43 | 4-amino-N-(6-methyl-1-((3,4,5-trichlorophenyl)amino)isoquinolin-5-yl)thieno[3,2-d]pyrimidine-7-carboxamide | 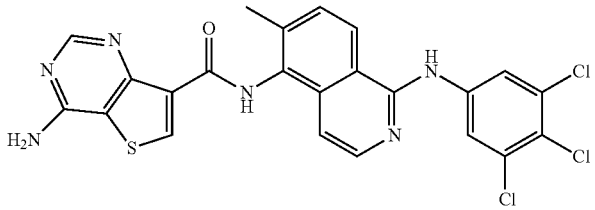 |
| 44 | 4-amino-N-(1-((4-chloro-3-methoxyphenyl)amino)-6-methylisoquinolin-5-yl)thieno[3,2-d]pyrimidine-7-carboxamide | 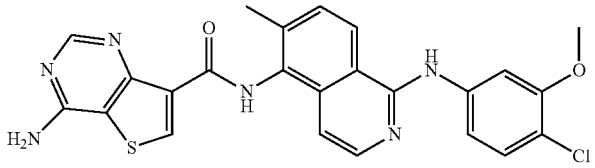 |

TABLE 1-continued

| Ex. | Name | Formula |
|---|---|---|
| 45 | 4-amino-N-(1-benzylamino-6-methylisoquinolin-5-yl)thieno[3,2-d]pyrimidine-7-carboxamide | 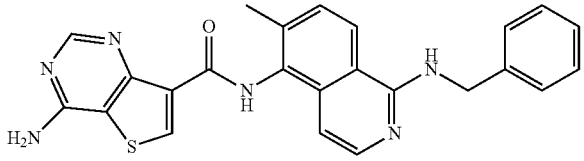 |
| 46 | 4-amino-N-(6-methyl-1-phenoxyisoquinolin-5-yl)thieno[3,2-d]pyrimidine-7-carboxamide | 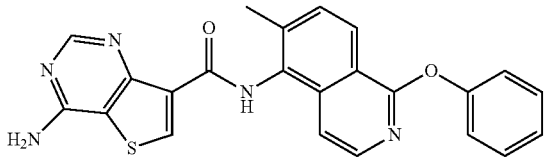 |
| 47 | 4-amino-N-(6-methyl-1-((4-morpholinophenyl)amino)isoquinolin-5-yl)thieno[3,2-d]pyrimidine-7-carboxamide | 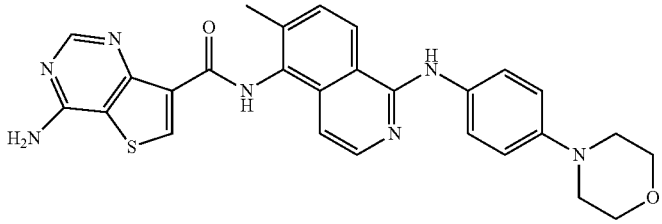 |
| 48 | N-(1-((4-(1H-pyrrol-1-yl)phenyl)amino)-6-methylisoquinolin-5-yl)-4-aminothieno[3,2-d]pyrimidine-7-carboxamide | 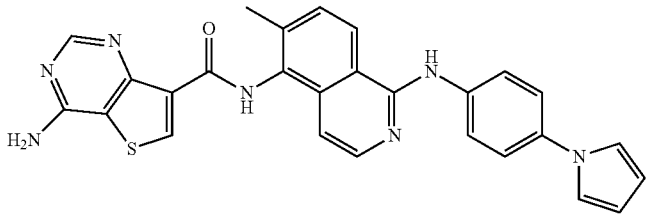 |
| 49 | 4-amino-N-(6-methyl-1-(pyrimidin-4-ylamino)isoquinolin-5-yl)thieno[3,2-d]pyrimidine-7-carboxamide | 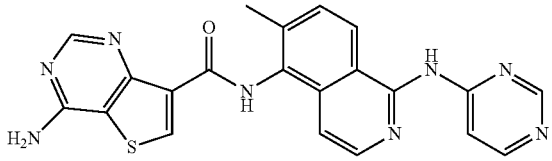 |
| 50 | 4-amino-N-(1-((4-(difluoromethoxy)phenyl)amino)-6-methylisoquinolin-5-yl)thieno[3,2-d]pyrimidine-7-carboxamide | 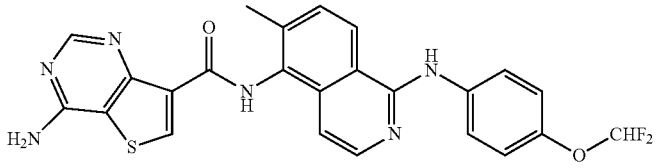 |
| 51 | 4-amino-N-(6-methyl-1-((4-(trifluoromethoxy)phenyl)amino)isoquinolin-5-yl)thieno[3,2-d]pyrimidine-7-carboxamide | 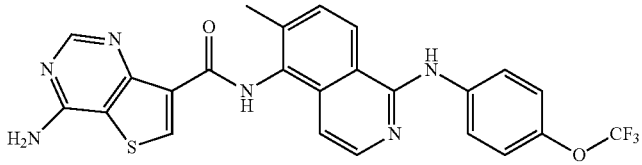 |
| 52 | 4-amino-N-(1-((4-chlorophenyl)amino)isoquinolin-5-yl)thieno[3,2-d]pyrimidine-7-carboxamide | 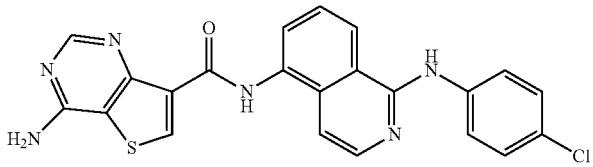 |

TABLE 1-continued

| Ex. | Name | Formula |
|---|---|---|
| 53 | 4-amino-N-(5-((4-chlorophenyl)amino)naphthalen-1-yl)thieno[3,2-d]pyrimidine-7-carboxamide | 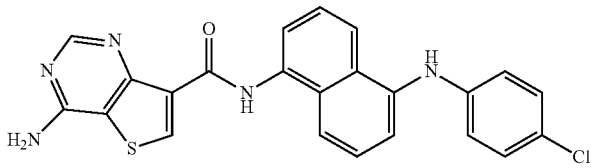 |
| 54 | 4-amino-N-(1-((4-ethynylphenyl)amino)-6-methylisoquinolin-5-yl)thieno[3,2-d]pyrimidine-7-carboxamide | 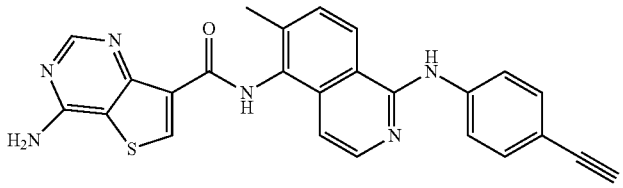 |
| 55 | 4-amino-N-(1-(isopropylamino)-6-methylisoquinolin-5-yl)thieno[3,2-d]pyrimidine-7-carboxamide | 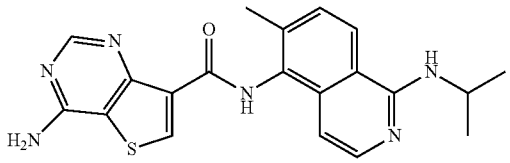 |
| 56 | 4-amino-N-(1-(indolin-6-ylamino)-6-methylisoquinolin-5-yl)thieno[3,2-d]pyrimidine-7-carboxamide | 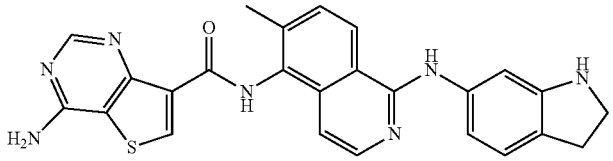 |
| 57 | 4-amino-N-(1-((4-(fluoromethoxy)phenyl)amino)-6-methylisoquinolin-5-yl)thieno[3,2-d]pyrimidine-7-carboxamide | 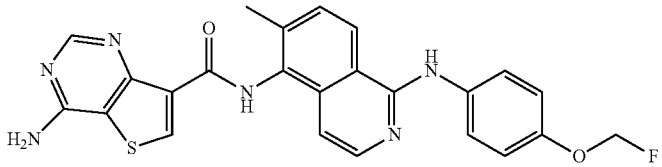 |
| 58 | N-(1-(4-chlorophenylamino)-6-methylisoquinolin-5-yl)thieno[3,2-d]pyrimidine-7-carboxamide | 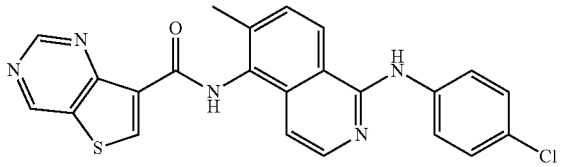 |
| 59 | 4-amino-N-(1-((4-chloro-3-((dimethylamino)methyl)phenyl)amino)-6-methylisoquinolin-5-yl)thieno[3,2-d]pyrimidine-7-carboxamide | 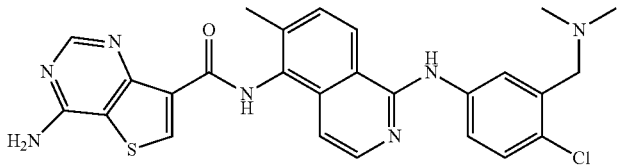 |
| 60 | 4-amino-N-(1-((4-chloro-3-(pyrrolidin-1-ylmethyl)phenyl)amino)-6-methylisoquinolin-5-yl)thieno[3,2-d]pyrimidine-7-carboxamide | 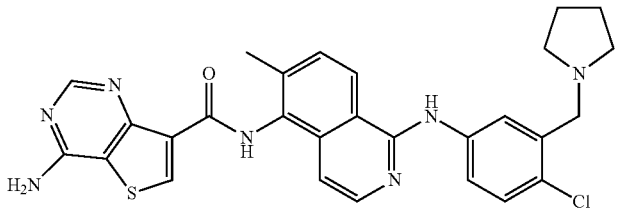 |

TABLE 1-continued

| Ex. | Name | Formula |
|---|---|---|
| 61 | 4-amino-N-(1-((4-chloro-3-((diethylamino)methyl)phenyl)amino)-6-methylisoquinolin-5-yl)thieno[3,2-d]pyrimidine-7-carboxamide | 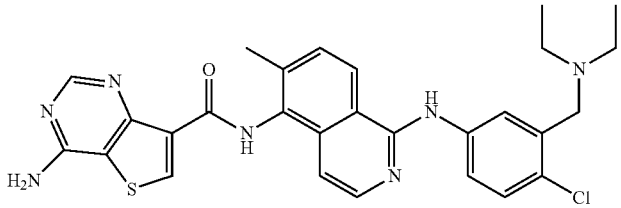 |
| 62 | 4-amino-N-(1-((1,4-diethyl-1,2,3,4-tetrahydroquinoxalin-6-yl)amino)-6-methylisoquinolin-5-yl)thieno[3,2-d]pyrimidine-7-carboxamide | 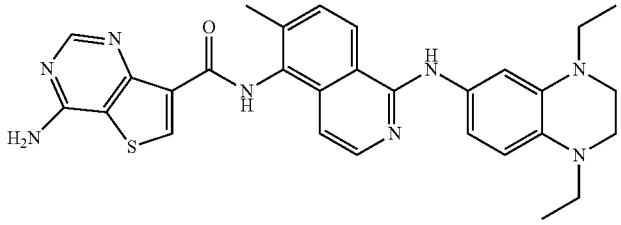 |
| 63 | 4-amino-N-(1-((4-chloro-3-(piperidin-1-ylmethyl)phenyl)amino)-6-methylisoquinolin-5-yl)thieno[3,2-d]pyrimidine-7-carboxamide | 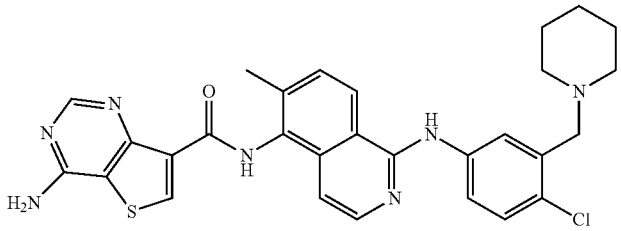 |
| 64 | 4-amino-N-(1-((4-chloro-3-(morpholinomethyl)phenyl)amino)-6-methylisoquinolin-5-yl)thieno[3,2-d]pyrimidine-7-carboxamide | 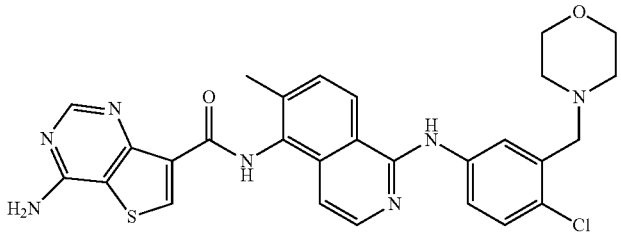 |
| 65 | 4-amino-N-(1-((4-chloro-3-((4-methylpiperazin-1-yl)methyl)phenyl)amino)-6-methylisoquinolin-5-yl)thieno[3,2-d]pyrimidine-7-carboxamide | 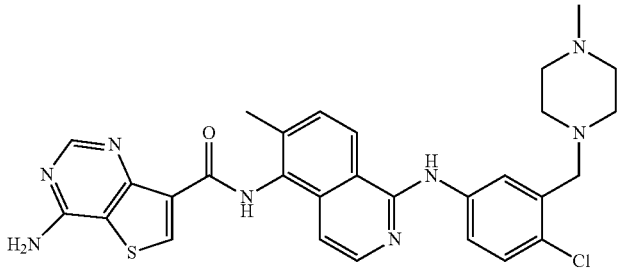 |
| 66 | 4-amino-N-(1-((4-chloro-3-((diisopropylamino)methyl)phenyl)amino)-6-methylisoquinolin-5-yl)thieno[3,2-d]pyrimidine-7-carboxamide | 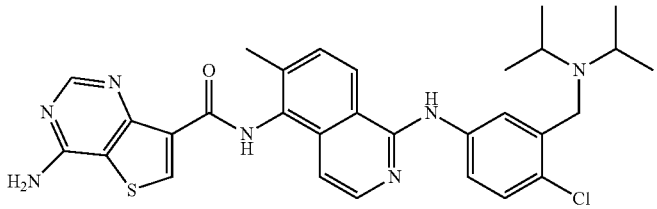 |
| 67 | 4-amino-N-(6-methyl-1-((3-(methylsulfonamido)phenyl)amino)isoquinolin-5-yl)thieno[3,2-d]pyrimidine-7-carboxamide | 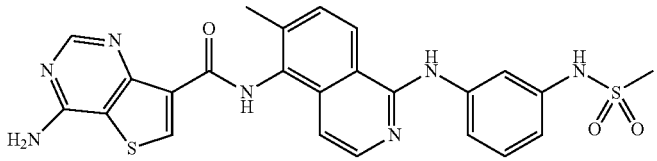 |

TABLE 1-continued

| Ex. | Name | Formula |
|---|---|---|
| 68 | tert-butyl 4-(5-((5-(4-aminothieno[3,2-d]pyrimidine-7-carboxamido)-6-methylisoquinolin-1-yl)amino)-2-chlorobenzyl)piperazine-1-carboxylate | 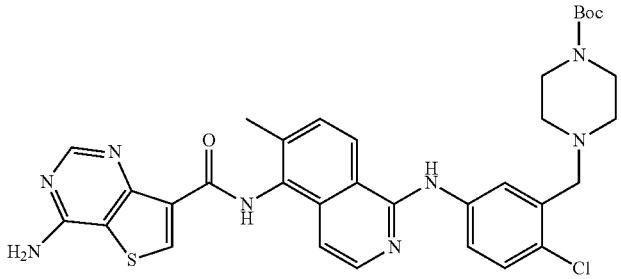 |
| 69 | 4-amino-N-(1-((4-chloro-3-(piperazin-1-ylmethyl)phenyl)amino)-6-methylisoquinolin-5-yl)thieno[3,2-d]pyrimidine-7-carboxamide | 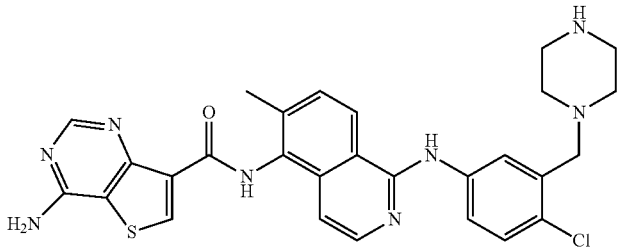 |
| 70 | 4-amino-N-(1-((3-chloro-4-methoxyphenyl)amino)-6-methylisoquinolin-5-yl)thieno[3,2-d]pyrimidine-7-carboxamide | 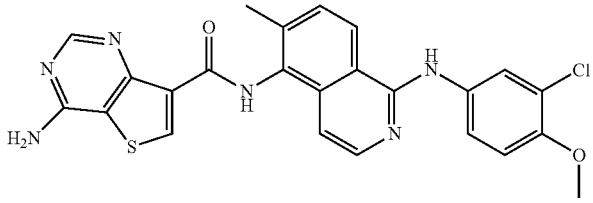 |
| 71 | 4-amino-N-(1-((3-(dimethylcarbamoyl)phenyl)amino)-6-methylisoquinolin-5-yl)thieno[3,2-d]pyrimidine-7-carboxamide | 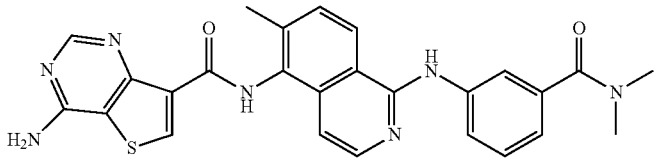 |
| 72 | 4-amino-N-(6-methyl-1-((3-(methylcarbamoyl)phenyl)amino)isoquinolin-5-yl)thieno[3,2-d]pyrimidine-7-carboxamide | 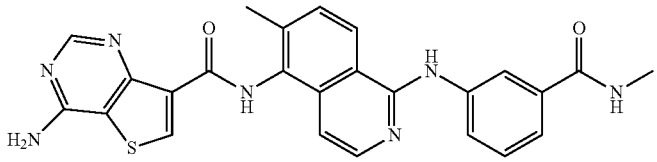 |
| 73 | 4-amino-N-(1-((4-chloro-2-fluorophenyl)amino)-6-methylisoquinolin-5-yl)thieno[3,2-d]pyrimidine-7-carboxamide | 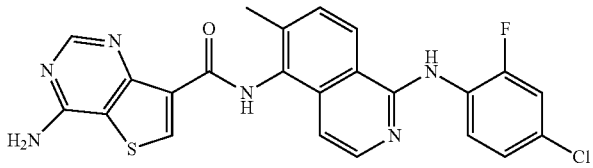 |
| 74 | 4-amino-N-(1-((4-bromo-2-fluorophenyl)amino)-6-methylisoquinolin-5-yl)thieno[3,2-d]pyrimidine-7-carboxamide | 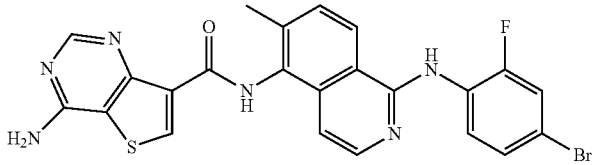 |

TABLE 1-continued

| Ex. | Name | Formula |
|---|---|---|
| 75 | 4-amino-N-(1-((4-methoxybenzyl)amino)-6-methylisoquinolin-5-yl)thieno[3,2-d]pyrimidine-7-carboxamide | 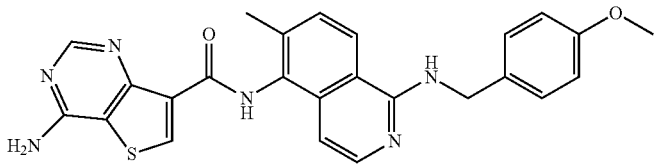 |
| 76 | 4-amino-N-(1-((4-chlorobenzyl)amino)-6-methylisoquinolin-5-yl)thieno[3,2-d]pyrimidine-7-carboxamide | 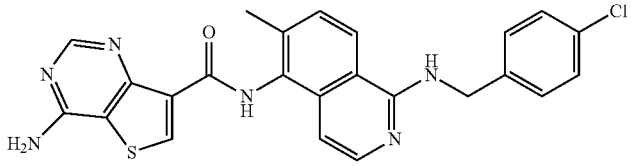 |
| 77 | 4-amino-N-(1-(2-(4-chlorophenyl)hydrazinyl)-6-methylisoquinolin-5-yl)thieno[3,2-d]pyrimidine-7-carboxamide | 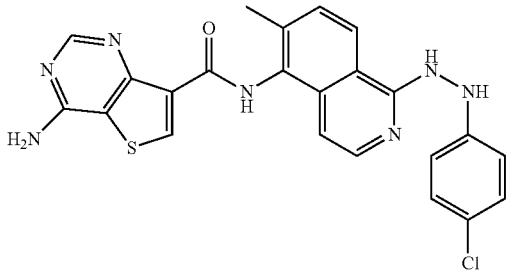 |
| 78 | 4-amino-N-(1-((3-((dimethylamino)methyl)phenyl)amino)-6-methylisoquinolin-5-yl)thieno[3,2-d]pyrimidine-7-carboxamide | 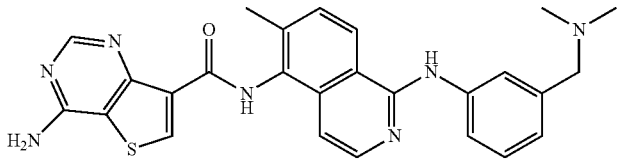 |
| 79 | 4-amino-N-(6-methyl-1-((4-oxo-4H-chromen-6-yl)amino)isoquinolin-5-yl)thieno[3,2-d]pyrimidine-7-carboxamide | 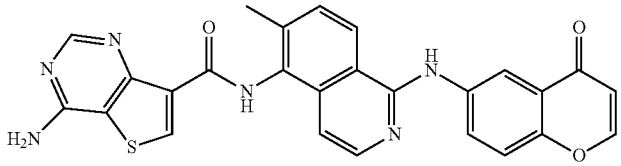 |
| 80 | N-(1-((3-acetylphenyl)amino)-6-methylisoquinolin-5-yl)-4-aminothieno[3,2-d]pyrimidine-7-carboxamide | 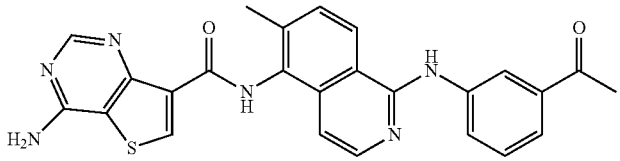 |
| 81 | 4-amino-N-(1-((4-(2-methoxyethoxy)phenyl)amino)-6-methylisoquinolin-5-yl)thieno[3,2-d]pyrimidine-7-carboxamide | 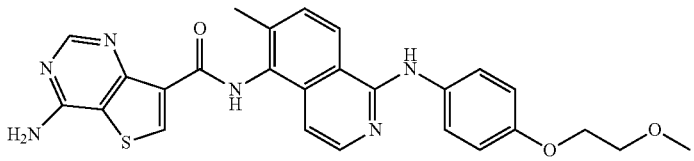 |
| 82 | 4-amino-N-(6-methyl-1-((3-(trifluoromethoxy)phenyl)amino)isoquinolin-5-yl)thieno[3,2-d]pyrimidine-7-carboxamide | 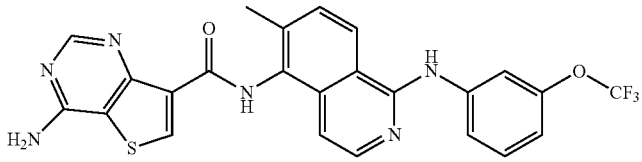 |

TABLE 1-continued

| Ex. | Name | Formula |
|---|---|---|
| 83 | N-(1-((4-acetylphenyl)amino)-6-methylisoquinolin-5-yl)-4-aminothieno[3,2-d]pyrimidine-7-carboxamide | 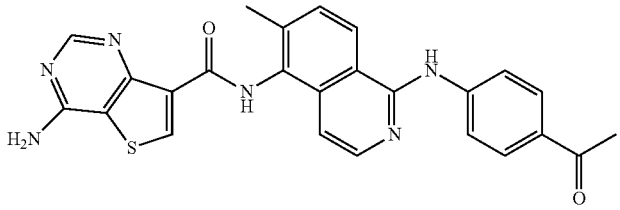 |
| 84 | 4-amino-N-(6-methyl-1-((4-(methylsulfonamido)phenyl)amino)isoquinolin-5-yl)thieno[3,2-d]pyrimidine-7-carboxamide | 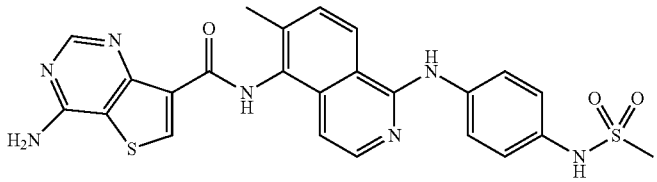 |
| 85 | 4-amino-N-(6-methyl-1-((3-(methylsulfonyl)phenyl)amino)isoquinolin-5-yl)thieno[3,2-d]pyrimidine-7-carboxamide | 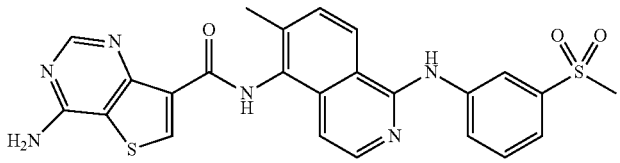 |
| 86 | 4-amino-N-(1-((4-chloro-3-(methoxymethyl)phenyl)amino)-6-methylisoquinolin-5-yl)thieno[3,2-d]pyrimidine-7-carboxamide | 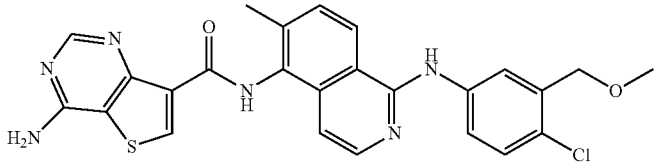 |
| 87 | 4-amino-N-(1-((4-methoxy-3-(methylsulfonamido)phenyl)amino)-6-methylisoquinolin-5-yl)thieno[3,2-d]pyrimidine-7-carboxamide | 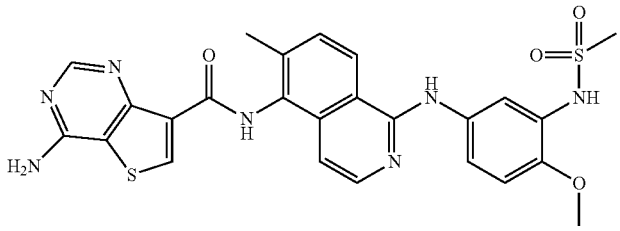 |
| 88 | 4-amino-N-(1-((4-chloro-3-(methylsulfonamido)phenyl)amino)-6-methylisoquinolin-5-yl)thieno[3,2-d]pyrimidine-7-carboxamide | 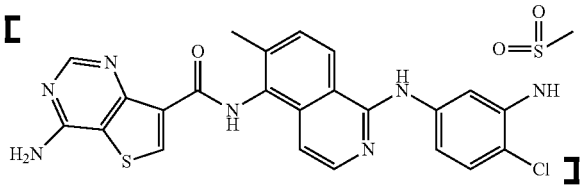 |
| | | 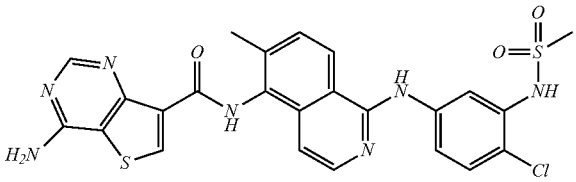 |
| 89 | 4-amino-N-(1-((6-chloropyridin-3-yl)amino)-6-methylisoquinolin-5-yl)thieno[3,2-d]pyrimidine-7-carboxamide | 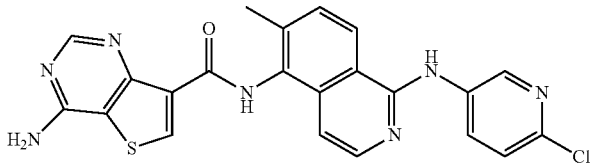 |

TABLE 1-continued

| Ex. | Name | Formula |
|---|---|---|
| 90 | 4-amino-N-(1-((2-chloropyridin-4-yl)amino)-6-methylisoquinolin-5-yl)thieno[3,2-d]pyrimidine-7-carboxamide | 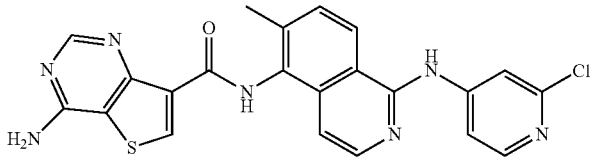 |
| 91 | 4-amino-N-(6-methyl-1-((4-(methylsulfonamidomethyl)phenyl)amino)isoquinolin-5-yl)thieno[3,2-d]pyrimidine-7-carboxamide | 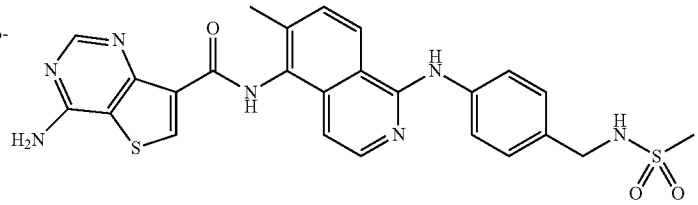 |
| 92 | 4-amino-N-(6-methyl-1-((3-(methylsulfonamidomethyl)phenyl)amino)isoquinolin-5-yl)thieno[3,2-d]pyrimidine-7-carboxamid | 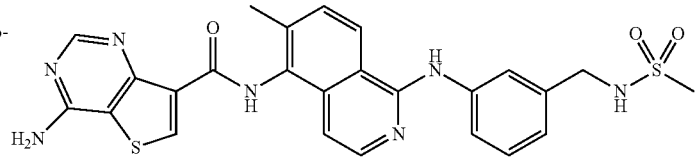 |
| 93 | 4-amino-N-(1-((4-chloro-3-fluorophenyl)amino)-6-methylisoquinolin-5-yl)thieno[3,2-d]pyrimidine-7-carboxamide | 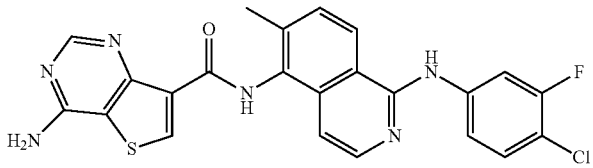 |
| 94 | 4-amino-N-(1-((3-bromo-4-chlorophenyl)amino)-6-methylisoquinolin-5-yl)thieno[3,2-d]pyrimidine-7-carboxamide | 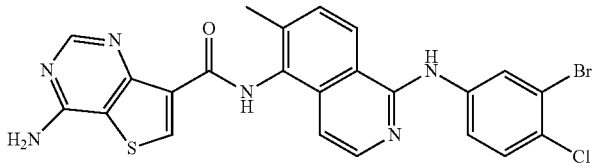 |
| 95 | 4-amino-N-(1-((4-(dimethylcarbamoyl)phenyl)amino)-6-methylisoquinolin-5-yl)thieno[3,2-d]pyrimidine-7-carboxamide | 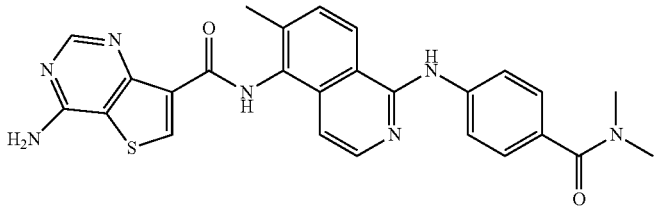 |
| 96 | N-(1-((3-acetamidophenyl)amino)-6-methylisoquinolin-5-yl)-4-aminothieno[3,2-d]pyrimidine-7-carboxamide | 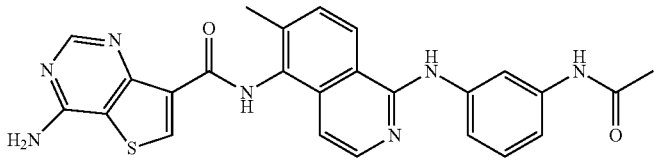 |
| 97 | 4-amino-N-(6-methyl-1-((1-methyl-1H-indazol-6-yl)amino)isoquinolin-5-yl)thieno[3,2-d]pyrimidine-7-carboxamide | 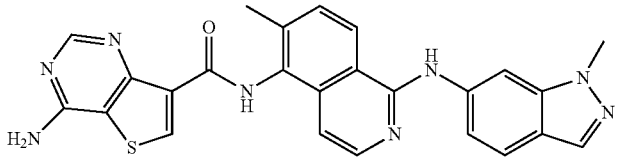 |

TABLE 1-continued

| Ex. | Name | Formula |
|---|---|---|
| 98 | 4-amino-N-(6-methyl-1-((4-(methylsulfinyl)phenyl)amino)isoquinolin-5-yl)thieno[3,2-d]pyrimidine-7-carboxamide | 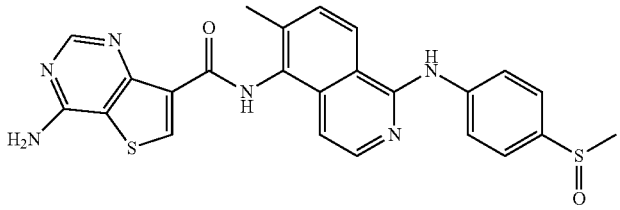 |
| 99 | 4-amino-N-(6-methyl-1-((2-methyl-1,3-dioxoisoindolin-5-yl)amino)isoquinolin-5-yl)thieno[3,2-d]pyrimidine-7-carboxamide | 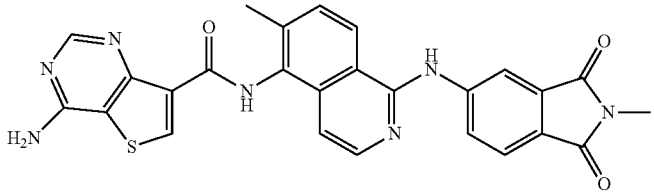 |
| 100 | 4-amino-N-(1-((6-methoxypyridin-3-yl)amino)-6-methylisoquinolin-5-yl)thieno[3,2-d]pyrimidine-7-carboxamide | 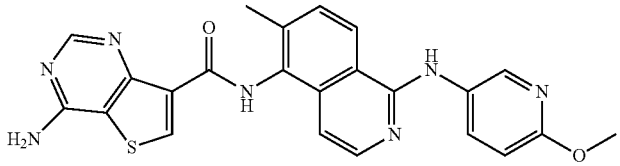 |
| 101 | 4-amino-N-(6-methyl-1-((3-(2,2,2-trifluoroacetyl)phenyl)amino)isoquinolin-5-yl)thieno[3,2-d]pyrimidine-7-carboxamide | 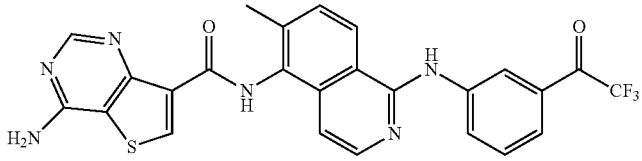 |
| 102 | 4-amino-N-(6-methyl-1-((4-propionylphenyl)amino)isoquinolin-5-yl)thieno[3,2-d]pyrimidine-7-carboxamide | 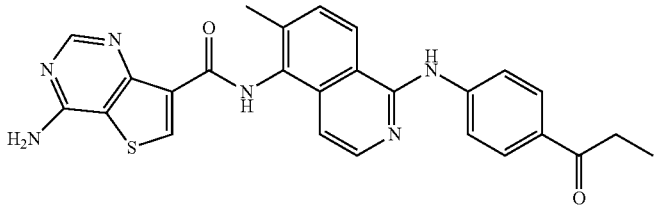 |
| 103 | 4-amino-N-(1-((4-hexanoylphenyl)amino)-6-methylisoquinolin-yl)thieno[3,2-d]pyrimidine-7-carboxamide | 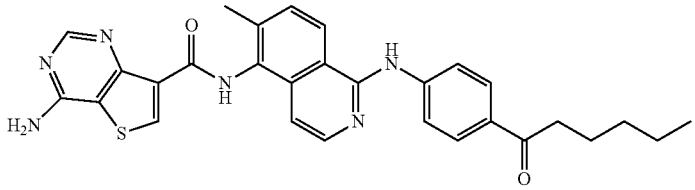 |
| 104 | N-(1-((1-acetyl-1H-indazol-6-yl)amino)-6-methylisoquinolin-5-yl)-4-aminothieno[3,2-d]pyrimidine-7-carboxamide | 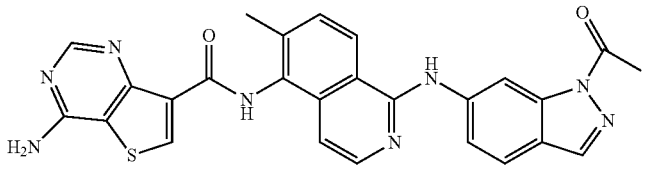 |
| 105 | 4-amino-N-(1-((3-chloro-4-fluorophenyl)amino)-6-methylisoquinolin-5-yl)thieno[3,2-d]pyrimidine-7-carboxamide | 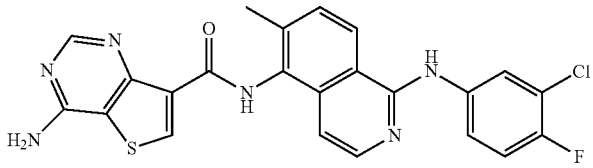 |

TABLE 1-continued

| Ex. | Name | Formula |
|---|---|---|
| 106 | 4-amino-N-(6-methyl-1-((5-oxo-5,6,7,8-tetrahydronaphthalen-2-yl)amino)isoquinolin-5-yl)thieno[3,2-d]pyrimidine-7-carboxamide | 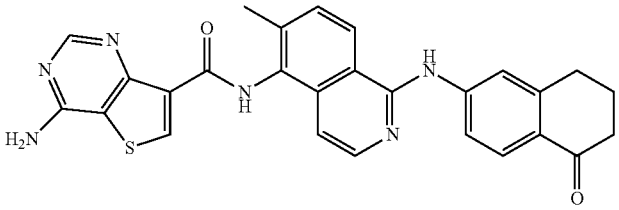 |
| 107 | 4-amino-N-(6-methyl-1-((2-methyl-2H-indazol-6-yl)amino)isoquinolin-5-yl)thieno[3,2-d]pyrimidine-7-carboxamide | 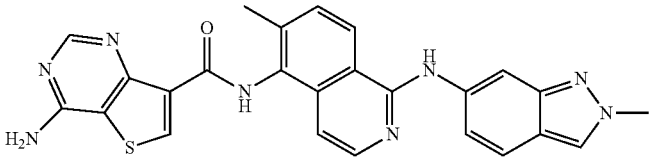 |
| 108 | methyl 4-((5-(4-aminothieno[3,2-d]pyrimidine-7-carboxamido)-6-methylisoquinolin-1-yl)amino)benzoate | 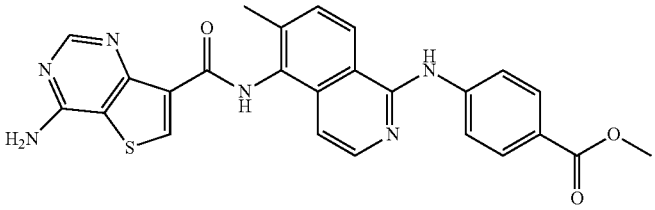 |
| 109 | 4-amino-N-(6-methyl-1-((1-methyl-1H-indazol-5-yl)amino)isoquinolin-5-yl)thieno[3,2-d]pyrimidine-7-carboxamide | 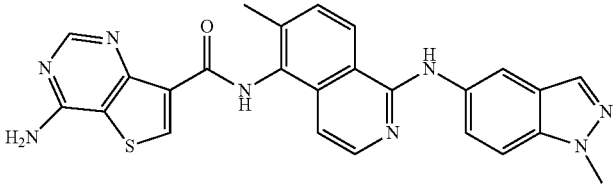 |
| 110 | 4-amino-N-(6-methyl-1-42-methyl-2H-indazol-5-yl)amino)isoquinolin-5-yl)thieno[3,2-d]pyrimidine-7-carboxamide | 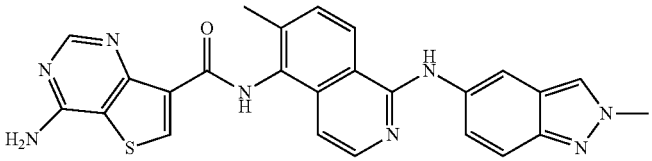 |
| 111 | 4-amino-N-(6-methyl-1-((6-methylpyridin-3-yl)amino)isoquinolin-5-yl)thieno[3,2-d]pyrimidine-7-carboxamide | 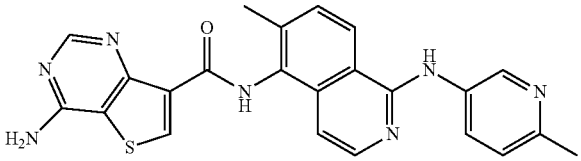 |
| 112 | 4-amino-N-(6-methyl-1-((1-methyl-1H-indol-6-yl)amino)isoquinolin-5-yl)thieno[3,2-d]pyrimidine-7-carboxamide | 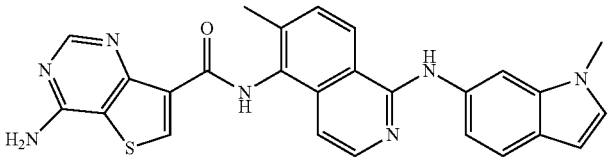 |
| 113 | tert-butyl 6-((5-(4-aminothieno[3,2-d]pyrimidine-7-carboxamido)-6-methylisoquinolin-1-yl)amino)-1H-indazol-1-carboxylate | 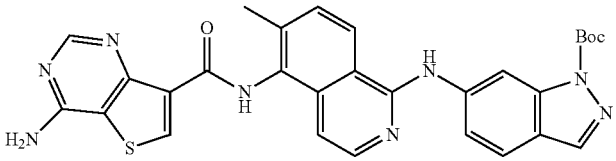 |

TABLE 1-continued

| Ex. | Name | Formula |
|---|---|---|
| 114 | N-(1-((1H-indazol-6-yl)amino)-6-methylisoquinolin-5-yl)-4-aminothieno[3,2-d]pyrimidine-7-carboxamide hydrochloride | 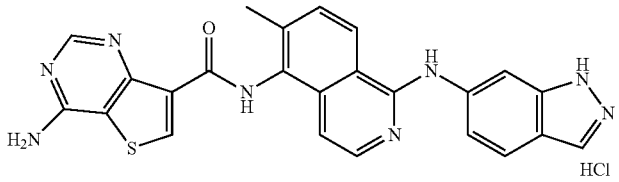 |
| 115 | 4-amino-N-(1-((5-chloro-2-fluorophenyl)amino)-6-methylisoquinolin-5-yl)thieno[3,2-d]pyrimidine-7-carboxamide | 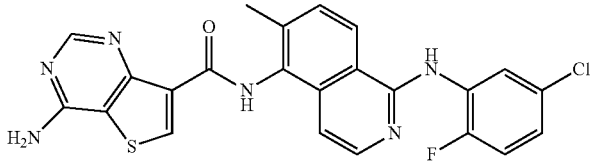 |
| 116 | 4-amino-N-(1-((3-chloro-2-fluorophenyl)amino)-6-methylisoquinolin-5-yl)thieno[3,2-d]pyrimidine-7-carboxamide | 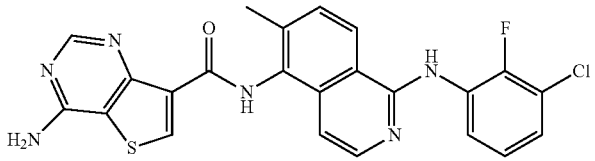 |
| 117 | 4-amino-N-(1-((3-fluoro-4-(4-methylpiperazin-1-yl)phenyl)amino)-6-methylisoquinolin-5-yl)thieno[3,2-d]pyrimidine-7-carboxamide | 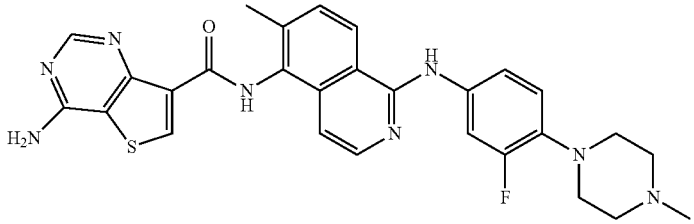 |
| 118 | 4-amino-N-(1-((3-chloro-1-methyl-1H-indazol-6-yl)amino)-6-methylisoquinolin-5-yl)thieno[3,2-d]pyrimidine-7-carboxamide | 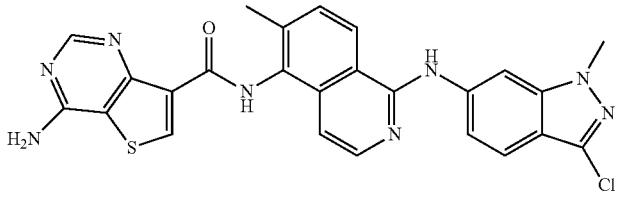 |
| 119 | 4-amino-N-(6-methyl-1-((4-(prop-2-yn-1-yloxy)phenyl)amino)isoquinolin-5-yl)thieno[3,2-d]pyrimidine-7-carboxamide | 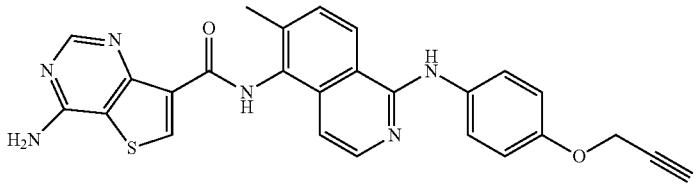 |
| 120 | 4-amino-N-(1-((2-methoxy-4-morpholinophenyl)amino)-6-methylisoquinolin-5-yl)thieno[3,2-d]pyrimidine-7-carboxamide | 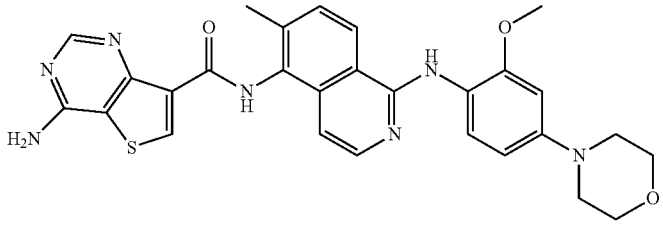 |
| 121 | 4-amino-N-(1-(benzo[d]thiazol-6-ylamino)-6-methylisoquinolin-5-yl)thieno[3,2-d]pyrimidine-7-carboxamide | 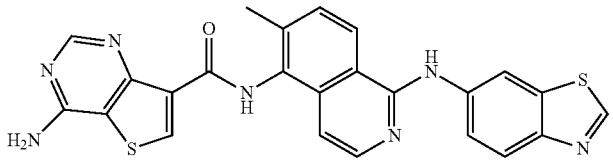 |

TABLE 1-continued

| Ex. | Name | Formula |
|---|---|---|
| 122 | N-(1-((1H-indazol-5-yl)amino)-6-methylisoquinolin-5-yl)-4-aminothieno[3,2-d]pyrimidine-7-carboxamide | 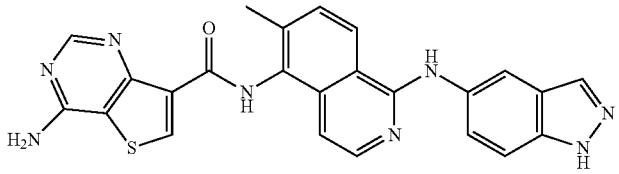 |
| 123 | 4-amino-N-(1-((3-chloro-2,4-difluorophenyl)amino)-6-methylisoquinolin-5-yl)thieno[3,2-d]pyrimidine-7-carboxamide | 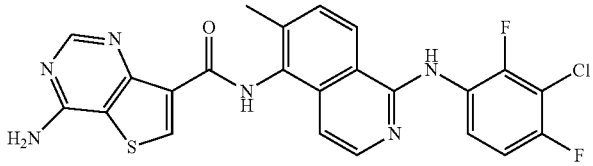 |
| 124 | 4-amino-N-(1-((3-(dimethylamino)propyl)amino)-6-methylisoquinolin-5-yl)thieno[3,2-d]pyrimidine-7-carboxamide | 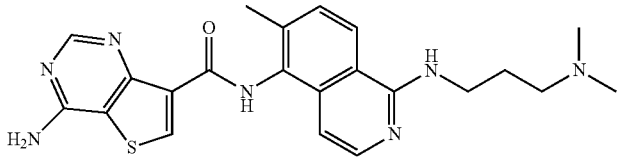 |
| 125 | 4-amino-N-(6-methyl-1-(piperidin-1-yl)isoquinolin-5-yl)thieno[3,2-d]pyrimidine-7-carboxamide | 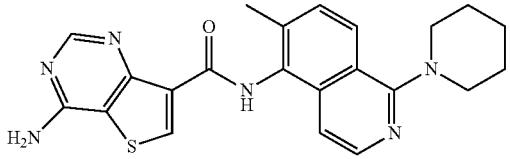 |

The compounds prepared in Examples were tested for biological assays as follows.

Experimental Example 1

Evaluation of RAF Kinase Activity

The compounds prepared in Examples were tested for inhibitory activity against three subtypes of RAF, i.e., RAF1 Y340D Y341D (C-RAF), B-RAF normal type and B-RAF$^{V600E}$ using Kinase Profiling Service (Invitrogen, U.S.) according to the manufacturer's instructions. The levels of enzymatic inhibition of the compounds were calculated as percent inhibition at various concentrations. Based on percent inhibition, dose-response curves were plotted using GraphPad Prism software. The $IC_{50}$ values of representative compounds against C-RAF are listed in Table 2, and Vemurafenib (PLX-4032, Roche) was used as a control.

TABLE 2

| Example | B-RAF ($IC_{50}$, nM) | B-RAFv$^{600E}$ ($IC_{50}$, nM) | C-RAF ($IC_{50}$, nM) |
|---|---|---|---|
| Control | 344 | 160 | 128 |
| 1 | 121 | 22 | 23 |
| 16 | 15 | 32 | 5 |
| 38 | 66 | 9 | 5 |
| 50 | 128 | 26 | 32 |
| 59 | 42 | 7 | 6 |
| 83 | 12 | 5 | 7 |
| 105 | 179 | 31 | 15 |
| 116 | 56 | 7 | 5 |

Experimental Example 2

Evaluation of FMS, DDR1 and DDR2 Kinases Activity

As such, the compounds prepared in Examples were tested for inhibitory activity against FMS, DDR1 and DDR2 kinases using Kinase Screening and Profiling Service (Invitrogen, U.S.). The $IC_{50}$ values of representative compounds are listed in Table 3, and Vemurafenib (PLX-4032) was used as a control.

TABLE 3

| Example | FMS ($IC_{50}$, nM) | DDR1 ($IC_{50}$, nM) | DDR2 ($IC_{50}$, nM) |
|---|---|---|---|
| Control | >1,000 | >1,000 | >1,000 |
| 1 | 1 | 2 | 5 |
| 38 | 57 | 40 | 93 |
| 83 | 4 | 5 | 10 |
| 105 | 50 | 71 | 181 |
| 116 | 10 | 23 | 44 |

Experimental Example 3

Evaluation of Inhibition on Cell Growth of N-RAS Mutant Cell $HepG_2$ (Hepatoma Carcinoma Cell)

The inventive compounds having an inhibitory activity for protein kinase, thieno[3,2-d]-pyrimidine derivatives or pharmaceutically acceptable salts thereof, were tested for inhibitory activities on proliferation of aberrant cells as follows.

N-RAS mutant cells $HepG_2$ cells (HCC) cell lines (ATCC # HB-8065™), were obtained from ATCC (American Type Culture Collection: Rockville, Md.). $HepG_2$ cell lines were incubated in a MEM medium supplemented with 10% FBS and 1% penicillin/streptomycin (Gibco BRL) under 37° C., 5% $CO_2$ and 95% air. The cell lines were transferred into 96-well plates at a density of 5,000 cells/well, and cultured for 18 hours or more. The cell lines were treated with 10 μl~0.1 nM of test compounds, and cultured for 72 hours.

To evaluate cell viabilities, $HepG_2$ cell lines were fixed with 10% TCA (trichloroacetic acid), stained with SRB (sulfohodamine B), and an absorbance was measured at 540 nm. Then, $GI_{50}$, i.e., the concentration of drug to cause 50% reduction in proliferation of cancer cells, were calculated therefrom. The growth rates of cancer cells were calculated by Equation 1 or 2.

$$[(Ti-Tz)/(C-Tz)]\times 100 \text{ (for } Ti>=Tz) \quad \text{[Equation 1]}$$

$$[(Ti-Tz/Tz)\times 100 \text{ (for } Ti<Tz) \quad \text{[Equation 2]}$$

In Equations 1 and 2, 'Tz' refers to a density of untreated cells, which is an absorbance in 0% cell growth groups. 'C' refers to a density of cells cultured by adding only medium, and 'Ti' refers to a density of cells treated with test compounds.

$GI_{50}$ value is the concentration of test compound when the value of Equation 1 is 50, which indicates the concentration of test compound needed to reduce the growth of cancer cells to 50%. On each measurement, test compounds were compared with a control. Vemurafenib (PLX-4032) was used as a control, and the $IC_{50}$ values of each compound were measured and shown in Table 4.

TABLE 4

| Example | HepG2 ($IC_{50}$, nM) |
|---|---|
| Control | >1,000 |
| 1 | 27 |
| 16 | 24 |
| 38 | 41 |
| 50 | 44 |
| 59 | 47 |
| 83 | 30 |
| 105 | 90 |
| 116 | 38 |

Experimental Example 4

Evaluation of Inhibition on Cell Growth of N-RAS Mutant Cell SK-Mel-2 (Melanoma)

The inventive compounds having an inhibitory activity for protein kinase, thieno[3,2-d]-pyrimidine derivatives or pharmaceutically acceptable salts thereof, were tested for their inhibitory activities on proliferation of aberrant cells as follows.

N-RAS mutant cells, SK-Mel-2 cell lines (ATCC #HTB-68™), were obtained from ATCC (American Type Culture Collection: Rockville, Md.). SK-Mel-2 cell lines were incubated in a MEM medium supplemented with 10% FBS and 1% penicillin/streptomycin (Gibco BRL) under 37° C., 5% $CO_2$ and 95% air. The cell lines were transferred into 96-well plates at a density of 5,000 cells/well, and cultured for 18 hours or more. The cells were treated with 10 μl~0.1 nM of test compounds, and cultured for 72 hours.

To evaluate cell viabilities, SK-Mel-2 cell lines were fixed with 10% TCA (trichloroacetic acid), stained with SRB (sulfohodamine B), and an absorbance was measured at 540 nm. Then, $GI_{50}$, i.e., the concentration of drug to cause 50% reduction in proliferation of cancer cells, were calculated therefrom. The growth rates of cancer cells were calculated by Equation 1 or 2.

$$[(Ti-Tz)/(C-Tz)]\times 100 \text{ (for } Ti>=Tz) \quad \text{[Equation 1]}$$

$$[(Ti-Tz/Tz)\times 100 \text{ (for } Ti<Tz) \quad \text{[Equation 2]}$$

In Equations 1 and 2, 'Tz' refers to a density of untreated cells, which is an absorbance in 0% cell growth groups. 'C' refers to a density of cells cultured by adding only medium, and 'Ti' refers to a density of cells treated with test compounds.

$GI_{50}$ value is the concentration of a test compound when the value of Equation 1 is 50, which indicates the concentration of test compound needed to reduce the growth of cancer cells to 50%. On each measurement, test compounds were compared with a control. Vemurafenib (PLX-4032) was used as a control, and the $IC_{50}$ values of each compound were measured and shown in Table 5.

TABLE 5

| Example | SK-Mel-2 ($IC_{50}$, nM) |
|---|---|
| Control | >1,000 |
| 1 | 56 |
| 16 | 52 |
| 38 | 97 |
| 50 | 163 |
| 59 | 236 |
| 83 | 60 |
| 105 | 210 |
| 116 | 76 |

As evidenced above, the inventive compounds, thieno[3,2-d]-pyrimidine derivative having inhibitory activity for protein kinases, can effectively inhibit various protein kinases including RAF, FMS, DDR1 and DDR2, and thus can be used, singly or in combination, for prevention and treatment of diseases associated with aberrant cell growth which are caused by mutation or overexpression of RAS protein or overactivation of its protein kinase.

What is claimed is:

1. A thieno[3,2-d]pyrimidine compound of formula (I) or a pharmaceutically acceptable salt thereof:

(I)

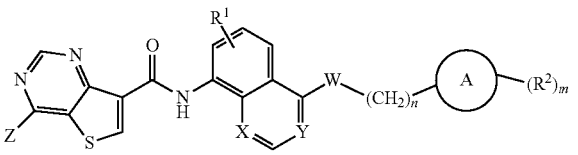

wherein,

A is [hydrogen, $C_{1-6}$ alkyl, $C_{3-6}$ cycloalkyl, 3- to 6-membered heterocycloalkyl,] $C_{6-10}$ aryl [or], 5- to 10-membered heteroaryl,

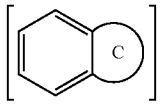

2,3-dihydrobenzo[b][1,4]dioxin-6-yl, benzo[d][1,3]dioxol-5-yl, 5,6,7,8-tetrahydronaphthalen-2-yl, idolin-6-yl, 1,4-diethyl-1,2,3,4[,]-tetrahydroquinoxalin-6-yl[;], 2-methyl-1,3-dioxoisoindolin-5-yl, or 5-oxo-5,6,7,-8-tetrahydronaphthalen-2-yl;

W is O, S, S(O), $S(O)_2$, NH, —NHNH— or 3- to 6-membered heterocycloalkyl;

X and Y are each independently CH or N;

Z is hydrogen, $C_{1-3}$ alkyl or $NR^3R^4$, wherein said $R^3$ and $R^4$ are each independently hydrogen, $C_{1-6}$ alkyl or —$(CH_2)$q-B—, B representing $NR^5R^6$, $C_{1-6}$ alkoxy, $C_{3-6}$ cycloalkyl or 3- to 6-membered heterocycloalkyl;

$R^1$ is hydrogen, halogen, $C_{1-3}$ alkyl or $C_{1-3}$ alkoxy, wherein said alkyl or alkoxy is unsubstituted or substituted with one or more halogen atoms;

$R^2$ is hydrogen, halogen, [=O,] —$CF_3$, —$NO_2$, —OH, —CN, $C_{1-6}$ alkoxy, $C_{1-6}$ alkyl, $C_{2-4}$ alkenyl, $C_{2-4}$ alkynyl, —$NR^7R^8$, —$NHSO_2R^9$, —$SO_2R^{10}$, —$C(O)R^{11}$, —$NHC(O)R^{12}$, —$NHC(O)OR^{13}$, —$S(O)R^{14}$, $C_{3-6}$ cycloalkyl, [5- to 10-membered heterocycloalkyl] *3- to 6-membered heterocycloalkyl*, $C_{6-10}$ aryl, $C_{6-10}$ aryloxy, 5- to 10-membered heteroaryl or [3- to 6-membered heteroaryloxy] *5- to 10-membered heteroaryloxy*, wherein said $R^2$ is connected to A by —$(CH_2)$p- or substituted with $C_{1-4}$ alkyl, $C_{2-4}$alkynyl, $C_{1-4}$ alkylcarbonyl or one or more halogen atoms;

$R^5$, $R^6$, $R^7$, $R^8$, $R^9$, $R^{10}$, $R^{11}$, $R^{12}$, $R^{13}$ and $R^{14}$ are each independently hydrogen, —$NH_2$, $C_{1-6}$ alkyl, $C_{1-6}$ alkoxy, $C_{3-6}$ cycloalkyl or 3- to 6-membered heterocycloalkyl, said alkyl, alkoxy, cycloalkyl or heterocycloalkyl being unsubstituted or substituted with one or more halogen atoms;

q is an integer ranging from 0 to 3;

p is an integer ranging from 0 to 3;

m is an integer ranging from 0 to 5; *and* n is an integer ranging from 0 to 2[; and when A is hydrogen, m is 0].

2. The thieno[3,2-d]pyrimidine compound [or its pharmaceutically acceptable salt] of claim 1, *or a pharmaceutically acceptable salt thereof,* wherein A is $C_{6-10}$ aryl or 5- to 10-membered heteroaryl.

3. The thieno[3,2-d]pyrimidine compound [or its pharmaceutically acceptable salt] of claim 1, *or a pharmaceutically acceptable salt thereof,* wherein W is NH.

4. The thieno[3,2-d]pyrimidine compound [or its pharmaceutically acceptable salt] of claim 1, *or a pharmaceutically acceptable salt thereof,* wherein Z is $NR^3R^4$.

5. The thieno[3,2-d]pyrimidine compound [or its pharmaceutically acceptable salt] of claim 1, *or a pharmaceutically acceptable salt thereof,* wherein X is CH and Y is N.

6. [The] *A* thieno[3,2-d]pyrimidine compound [or its pharmaceutically acceptable salt of claim 1, which is] selected from the group consisting of:

1) 4-amino-N-(1-((4-chlorophenyl)amino)-6-methylisoquinolin-5-yl)thieno[3,2-d]pyrimidine-7-carboxamide;

2) 4-amino-N-(6-methyl-1-((3-(trifluoromethyl)phenyl)amino)isoquinolin-5-yl)thieno[3,2-d]pyrimidine-7-carboxamide;

3) N-(1-((4-chlorophenyl)amino)-6-methylisoquinolin-5-yl)-4-(cyclopropylamino)thieno[3,2-d]pyrimidine-7-carboxamide;

4) 4-(cyclopropylamino)-N-(6-methyl-1-((3-(trifluoromethyl)phenyl)amino)isoquinolin-5-yl)thieno[3,2-d]pyrimidine-7-carboxamide;

5) 4-amino-N-(6-methyl-1-((3-(4-methyl-1H-imidazol-1-yl)-5-(trifluoromethyl)phenyl)amino)isoquinolin-5-yl)thieno[3,2-d]pyrimidine-7-carboxamide;

6) 4-(cyclopropylamino)-N-(6-methyl-1-((3-(4-methyl-1H-imidazol-1-yl)-5-(trifluoromethyl)phenyl)amino)isoquinolin-5-yl)thieno[3,2-d]pyrimidine-7-carboxamide;

7) 4-amino-N-(1-((4-((4-ethylpiperazin-1-yl)methyl)-3-(trifluoromethyl)phenyl)amino)-6-methylisoquinolin-5-yl)thieno[3,2-d]pyrimidine-7-carboxamide;

8) 4-(cyclopropylamino)-N-(1-((4-((4-ethylpiperazin-1-yl)methyl)-3-(trifluoromethyl)phenyl)amino)-6-methylisoquinolin-5-yl)thieno[3,2-d]pyrimidine-7-carboxamide;

9) N-(1-((4-((4-ethylpiperazin-1-yl)methyl)-3-(trifluoromethyl)phenyl)amino)-6-methylisoquinolin-5-yl)-4-(methylamino)thieno[3,2-d]pyrimidine-7-carboxamide;

10) 4-amino-N-(1-((4-(4-ethylpiperazin-1-yl)phenyl)amino)-6-methylisoquinolin-5-yl)thieno[3,2-d]pyrimidine-7-carboxamide;

11) 4-amino-N-(1-((4-((4-ethylpiperazin-1-yl)methyl)phenyl)amino)-6-methylisoquinolin-5-yl)thieno[3,2-d]pyrimidine-7-carboxamide;

12) 4-amino-N-(6-methyl-1-((3-(trifluoromethyl)phenyl)amino)isoquinolin-5-yl)thieno[3,2-d]pyrimidine-7-carboxamide;

13) 4-amino-N-(1-((4-chloro-3-(trifluoromethyl)phenyl)amino)-6-methylisoquinolin-5-yl)thieno[3,2-d]pyrimidine-7-carboxamide;

14) 4-amino-N-(1-((2-methoxy-5-(trifluoromethyl)phenyl)amino)-6-methylisoquinolin-5-yl)thieno[3,2-d]pyrimidine-7-carboxamide;

15) 4-amino-N-(6-methyl-1-((4-(trifluoromethyl)phenyl)amino)isoquinolin-5-yl)thieno[3,2-d]pyrimidine-7-carboxamide;

16) 4-amino-N-(1-((4-methoxyphenyl)amino)-6-methylisoquinolin-5-yl)thieno[3,2-d]pyrimidine-7-carboxamide;

17) 4-amino-N-(6-methyl-1-(p-tolylamino)isoquinolin-5-yl)thieno[3,2-d]pyrimidine-7-carboxamide;

18) 4-amino-N-(1-((4-isopropylphenyl)amino)-6-methylisoquinolin-5-yl)thieno[3,2-d]pyrimidine-7-carboxamide;

19) 4-amino-N-(1-((5-(t-butyl)isoxazol-3-yl)amino)-6-methylisoquinolin-5-yl)thieno[3,2-d]pyrimidine-7-carboxamide;

20) 4-amino-N-(1-((4-fluorophenyl)amino)-6-methylisoquinolin-5-yl)thieno[3,2-d]pyrimidine-7-carboxamide;

21) 4-amino-N-(6-methyl-1-(thiazol-2-ylamino)isoquinolin-5-yl)thieno[3,2-d]pyrimidine-7-carboxamide;

22) 4-amino-N-(1-((4-cyanophenyl)amino)-6-methylisoquinolin-5-yl)thieno[3,2-d]pyrimidine-7-carboxamide;

23) 4-amino-N-(6-methyl-1-(quinolin-5-ylamino)isoquinolin-5-yl)thieno[3,2-d]pyrimidine-7-carboxamide;

24) 4-amino-N-(1-((4-ethoxyphenyl)amino)-6-methylisoquinolin-5-yl)thieno[3,2-d]pyrimidine-7-carboxamide;

25) 4-amino-N-(6-methyl-1-((4-phenoxyphenyl)amino)isoquinolin-5-yl)thieno[3,2-d]pyrimidine-7-carboxamide;

26) 4-amino-N-(1-((4-hydroxyphenyl)amino)-6-methylisoquinolin-5-yl)thieno[3,2-d]pyrimidine-7-carboxamide;

27) 4-amino-N-(1-((4-isopropoxyphenyl)amino)-6-methylisoquinolin-5-yl)thieno[3,2-d]pyrimidine-7-carboxamide;

28) [4-amino-N-(1-((4-(dimethylamino)-6-methylisoquinolin-5-yl)thieno[3,2-d]pyrimidine-7-carboxamide]

*4-amino-N-(1-((4-dimethylaminophenyl)amino)-6-methylisoquinolin-5-yl)thieno[3,2-d]pyrimidine-7-carboxamide*;

29) 4-amino-N-(1-((2,3-dihydrobenzo[b][1,4]dioxin-6-yl)amino)-6-methylisoquinolin-5-yl)thieno[3,2-d]pyrimidine-7-carboxamide;

30) 4-amino-N-(1-((3,4-dimethoxyphenyl)amino)-6-methylisoquinolin-5-yl)thieno[3,2-d]pyrimidine-7-carboxamide;

31) 4-amino-N-(1-((3-fluoro-4-methoxyphenyl)amino)-6-methylisoquinolin-5-yl)thieno[3,2-d]pyrimidine-7-carboxamide;

32) 4-amino-N-(6-methyl-1-((3,4,5-trimethoxyphenyl)amino)isoquinolin-5-yl)thieno[3,2-d]pyrimidine-7-carboxamide;

[33) 4-amino-N-(6-methylisoquinolin-5-yl)thieno[3,2-d]pyrimidine-7-carboxamide;]

34) 4-amino-N-(1-(benzo[d][1,3]dioxol-5-ylamino)-6-methylisoquinolin-5-yl)thieno[3,2-d]pyrimidine-7-carboxamide;

35) 4-amino-N-(6-methyl-1-((5,6,7,8-tetrahydronaphthalen-2-yl)amino)isoquinolin-5-yl)thieno[3,2-d]pyrimidine-7-carboxamide;

36) 4-amino-N-(4-((4-chlorophenyl)amino)-7-methylquinazolin-8-yl)thieno[3,2-d]pyrimidine-7-carboxamide;

37) 4-(cyclopropylamino)-N-(1-((4-methoxyphenyl)amino)-6-methylisoquinolin-5-yl)thieno[3,2-d]pyrimidine-7-carboxamide;

38) 4-amino-N-(1-((3-chlorophenyl)amino)-6-methylisoquinolin-5-yl)thieno[3,2-d]pyrimidine-7-carboxamide;

39) 4-amino-N-(1-((3-bromophenyl)amino)-6-methylisoquinolin-5-yl)thieno[3,2-d]pyrimidine-7-carboxamide;

40) 4-amino-N-(1-((2,4-dichlorophenyl)amino)-6-methylisoquinolin-5-yl)thieno[3,2-d]pyrimidine-7-carboxamide;

41) 4-amino-N-(1-((3,4-dichlorophenyl)amino)-6-methylisoquinolin-5-yl)thieno[3,2-d]pyrimidine-7-carboxamide;

42) 4-amino-N-(1-((3,5-dichlorophenyl)amino)-6-methylisoquinolin-5-yl)thieno[3,2-d]pyrimidine-7-carboxamide;

43) 4-amino-N-(6-methyl-1-((3,4,5-trichlorophenyl)amino)isoquinolin-5-yl)thieno[3,2-d]pyrimidine-7-carboxamide;

44) 4-amino-N-(1-((4-chloro-3-methoxyphenyl)amino)-6-methylisoquinolin-5-yl)thieno[3,2-d]pyrimidine-7-carboxamide;

45) 4-amino-N-(1-benzylamino-6-methylisoquinolin-5-yl)thieno[3,2-d]pyrimidine-7-carboxamide;

46) 4-amino-N-(6-methyl-1-phenoxyisoquinolin-5-yl)thieno[3,2-d]pyrimidine-7-carboxamide;

47) 4-amino-N-(6-methyl-1-((4-morpholinophenyl)amino)isoquinolin-5-yl)thieno[3,2-d]pyrimidine-7-carboxamide;

48) N-(1-((4-(1H-pyrrol-1-yl)phenyl)amino)-6-methylisoquinolin-5-yl)-4-aminothieno[3,2-d]pyrimidine-7-carboxamide;

49) 4-amino-N-(6-methyl-1-(pyrimidin-4-ylamino)isoquinolin-5-yl)thieno[3,2-d]pyrimidine-7-carboxamide;

50) 4-amino-N-(1-((4-(difluoromethoxy)phenyl)amino)-6-methylisoquinolin-5-yl)thieno[3,2-d]pyrimidine-7-carboxamide;

51) 4-amino-N-(6-methyl-1-((4-(trifluoromethoxy)phenyl)amino)isoquinolin-5-yl)thieno[3,2-d]pyrimidine-7-carboxamide;

52) 4-amino-N-(1-((4-chlorophenyl)amino)isoquinolin-5-yl)thieno[3,2-d]pyrimidine-7-carboxamide;

53) 4-amino-N-(5-((4-chlorophenyl)amino)naphthalen-1-yl)thieno[3,2-d]pyrimidine-7-carboxamide;

54) 4-amino-N-(1-((4-ethynylphenyl)amino)-6-methylisoquinolin-5-yl)thieno[3,2-d]pyrimidine-7-carboxamide;

[55) 4-amino-N-(1-(isopropylamino)-6-methylisoquinolin-5-yl)thieno[3,2-d]pyrimidine-7-carboxamide;]

56) 4-amino-N-(1-(indolin-6-ylamino)-6-methylisoquinolin-5-yl)thieno[3,2-d]pyrimidine-7-carboxamide;

57) 4-amino-N-(1-((4-(fluoromethoxy)phenyl)amino)-6-methylisoquinolin-5-yl)thieno[3,2-d]pyrimidine-7-carboxamide;

58) N-(1-(4-chlorophenylamino)-6-methylisoquinolin-5-yl)thieno[3,2-d]pyrimidine-7-carboxamide;

59) 4-amino-N-(1-((4-chloro-3-((dimethylamino)methyl)phenyl)amino)-6-methylisoquinolin-5-yl)thieno[3,2-d]pyrimidine-7-carboxamide;

60) 4-amino-N-(1-((4-chloro-3-(pyrrolidin-1-ylmethyl)phenyl)amino)-6-methylisoquinolin-5-yl)thieno[3,2-d]pyrimidine-7-carboxamide;

61) 4-amino-N-(1-((4-chloro-3-((diethylamino)methyl)phenyl)amino)-6-methylisoquinolin-5-yl)thieno[3,2-d]pyrimidine-7-carboxamide;

62) 4-amino-N-(1-((1,4-diethyl-1,2,3,4-tetrahydroquinoxalin-6-yl)amino)-6-methylisoquinolin-5-yl)thieno[3,2-d]pyrimidine-7-carboxamide;

63) 4-amino-N-(1-((4-chloro-3-(piperidin-1-ylmethyl)phenyl)amino)-6-methylisoquinolin-5-yl)thieno[3,2-d]pyrimidine-7-carboxamide;

64) 4-amino-N-(1-((4-chloro-3-(morpholinomethyl)phenyl)amino)-6-methylisoquinolin-5-yl)thieno[3,2-d]pyrimidine-7-carboxamide;

65) 4-amino-N-(1-((4-chloro-3-((4-methylpiperazin-1-yl)methyl)phenyl)amino)-6-methylisoquinolin-5-yl)thieno[3,2-d]pyrimidine-7-carboxamide;

66) 4-amino-N-(1-((4-chloro-3-((diisopropylamino)methyl)phenyl)amino)-6-methylisoquinolin-5-yl)thieno[3,2-d]pyrimidine-7-carboxamide;

67) 4-amino-N-(6-methyl-1-((3-(methylsulfonamido)phenyl)amino)isoquinolin-5-yl)thieno[3,2-d]pyrimidine-7-carboxamide;

68) tert-butyl 4-(5-((5-(4-aminothieno[3,2-d]pyrimidine-7-carboxamido)-6-methylisoquinolin-1-yl)amino)-2-chlorobenzyl)piperazine-1-carboxylate;

69) 4-amino-N-(1-((4-chloro-3-(piperazin-1-ylmethyl)phenyl)amino)-6-methylisoquinolin-5-yl)thieno[3,2-d]pyrimidine-7-carboxamide;

70) 4-amino-N-(1-((3-chloro-4-methoxyphenyl)amino)-6-methylisoquinolin-5-yl)thieno[3,2-d]pyrimidine-7-carboxamide;

[71) 4-amino-N-(1-((3-(dimethylcarbamoyl)phenyl)amino)-6-methylisoquinolin-5-yl)thieno[3,2-d]pyrimidine-7-carboxamide;

72) 4-amino-N-(6-methyl-1-((3-(methylcarbamoyl)phenyl)amino)isoquinolin-5-yl)thieno[3,2-d]pyrimidine-7-carboxamide;]

73) 4-amino-N-(1-((4-chloro-2-fluorophenyl)amino)-6-methylisoquinolin-5-yl)thieno[3,2-d]pyrimidine-7-carboxamide;

74) 4-amino-N-(1-((4-bromo-2-fluorophenyl)amino)-6-methylisoquinolin-5-yl)thieno[3,2-d]pyrimidine-7-carboxamide;

75) 4-amino-N-(1-((4-methoxybenzyl)amino)-6-methylisoquinolin-5-yl)thieno[3,2-d]pyrimidine-7-carboxamide;

76) 4-amino-N-(1-((4-chlorobenzyl)amino)-6-methylisoquinolin-5-yl)thieno[3,2-d]pyrimidine-7-carboxamide;

77) 4-amino-N-(1-(2-(4-chlorophenyl)hydrazinyl)-6-methylisoquinolin-5-yl)thieno[3,2-d]pyrimidine-7-carboxamide;

78) 4-amino-N-(1-((3-((dimethylamino)methyl)phenyl)amino)-6-methylisoquinolin-5-yl)thieno[3,2-d]pyrimidine-7-carboxamide;

79) 4-amino-N-(6-methyl-1-((4-oxo-4H-chromen-6-yl)amino)isoquinolin-5-yl)thieno[3,2-d]pyrimidine-7-carboxamide;

80) N-(1-((3-acetylphenyl)amino)-6-methylisoquinolin-5-yl)-4-aminothieno[3,2-d]pyrimidine-7-carboxamide;

[81) 4-amino-N-(1-((4-(2-methoxyethoxyl)phenyl)amino)-6-methylisoquinolin-5-yl)thieno[3,2-d]pyrimidine-7-carboxamide;]

82) 4-amino-N-(6-methyl-1-((3-(trifluoromethoxy)phenyl)amino)isoquinolin-5-yl)thieno[3,2-d]pyrimidine-7-carboxamide;

83) N-(1-((4-acetylphenyl)amino)-6-methylisoquinolin-5-yl)-4-aminothieno[3,2-d]pyrimidine-7-carboxamide;

84) 4-amino-N-(6-methyl-1-((4-(methylsulfonamido)phenyl)amino)isoquinolin-5-yl)thieno[3,2-d]pyrimidine-7-carboxamide;

85) 4-amino-N-(6-methyl-1-((3-(methylsulfonyl)phenyl)amino)isoquinolin-5-yl)thieno[3,2-d]pyrimidine-7-carboxamide;

86) 4-amino-N-(1-((4-chloro-3-(methoxymethyl)phenyl)amino)-6-methylisoquinolin-5-yl)thieno[3,2-d]pyrimidine-7-carboxamide;

87) 4-amino-N-(1-((4-methoxy-3-(methylsulfonamido)phenyl)amino)-6-methylisoquinolin-5-yl)thieno[3,2-d]pyrimidine-7-carboxamide;

88) 4-amino-N-(1-((4-chloro-3-(methylsulfonamido)phenyl)amino)-6-methylisoquinolin-5-yl)thieno[3,2-d]pyrimidine-7-carboxamide;

89) 4-amino-N-(1-((6-chloropyridin-3-yl)amino)-6-methylisoquinolin-5-yl)thieno[3,2-d]pyrimidine-7-carboxamide;

90) 4-amino-N-(1-((2-chloropyridin-4-yl)amino)-6-methylisoquinolin-5-yl)thieno[3,2-d]pyrimidine-7-carboxamide;

91) 4-amino-N-(6-methyl(4-(methylsulfonamidomethyl)phenyl)amino)isoquinolin-5-yl)thieno[3,2-d]pyrimidine-7-carboxamide;

92) 4-amino-N-(6-methyl-1-((3-(methylsulfonamidomethyl)phenyl)amino)isoquinolin-5-yl)thieno[3,2-d]pyrimidine-7-carboxamide;

93) 4-amino-N-(1-((4-chloro-3-fluorophenyl)amino)-6-methylisoquinolin-5-yl)thieno[3,2-d]pyrimidine-7-carboxamide;

94) 4-amino-N-(1-((3-bromo-4-chlorophenyl)amino)-6-methylisoquinolin-5-yl)thieno[3,2-d]pyrimidine-7-carboxamide;

[95) 4-amino-N-(1-((4-(dimethylcarbamoyl)phenyl)amino)-6-methylisoquinolin-5-yl)thieno[3,2-d]pyrimidine-7-carboxamide;]

96) N-(1-((3-acetamidophenyl)amino)-6-methylisoquinolin-5-yl)-4-aminothieno[3,2-d]pyrimidine-7-carboxamide;

97) 4-amino-N-(6-methyl-1-((1-methyl-1H-indazol-6-yl)amino)isoquinolin-5-yl)thieno[3,2-d]pyrimidine-7-carboxamide;

98) 4-amino-N-(6-methyl-1-((4-(methylsulfinyl)phenyl)amino)isoquinolin-5-yl)thieno[3,2-d]pyrimidine-7-carboxamide;

99) 4-amino-N-(6-methyl-1-((2-methyl-1,3-dioxoisoindolin-5-yl)amino)isoquinolin-5-yl)thieno[3,2-d]pyrimidine-7-carboxamide;

100) 4-amino-N-(1-((6-methoxypyridin-3-yl)amino)-6-methylisoquinolin-5-yl)thieno[3,2-d]pyrimidine-7-carboxamide;

101) 4-amino-N-(6-methyl-1-((3-(2,2,2-trifluoroacetyl)phenyl)amino)isoquinolin-5-yl)thieno[3,2-d]pyrimidine-7-carboxamide;

102) 4-amino-N-(6-methyl-1-((4-propionylphenyl)amino)isoquinolin-5-yl)thieno[3,2-d]pyrimidine-7-carboxamide;

103) 4-amino-N-(1-((4-hexanoylphenyl)amino)-6-methylisoquinolin-yl)thieno[3,2-d]pyrimidine-7-carboxamide;

104) N-(1-((1-acetyl-1H-indazol-6-yl)amino)-6-methylisoquinolin-5-yl)-4-aminothieno[3,2-d]pyrimidine-7-carboxamide;

105) 4-amino-N-(1-((3-chloro-4-fluorophenyl)amino)-6-methylisoquinolin-5-yl)thieno[3,2-d]pyrimidine-7-carboxamide;

106) 4-amino-N-(6-methyl-1-((5-oxo-5,6,7,8-tetrahydronaphthalen-2-yl)amino)isoquinolin-5-yl)thieno[3,2-d]pyrimidine-7-carboxamide;

107) 4-amino-N-(6-methyl-1-((2-methyl-2H-indazol-6-yl)amino)isoquinolin-5-yl)thieno[3,2-d]pyrimidine-7-carboxamide;

108) methyl 4-((5-(4-aminothieno[3,2-d]pyrimidine-7-carboxamido)-6-methylisoquinolin-1-yl)amino)benzoate;

109) 4-amino-N-(6-methyl-1-((1-methyl-1H-indazol-5-yl)amino)isoquinolin-5-yl)thieno[3,2-d]pyrimidine-7-carboxamide;

110) 4-amino-N-(6-methyl-1-((2-methyl-2H-indazol-5-yl)amino)isoquinolin-5-yl)thieno[3,2-d]pyrimidine-7-carboxamide;

111) 4-amino-N-(6-methyl-1-((6-methylpyridin-3-yl)amino)isoquinolin-5-yl)thieno[3,2-d]pyrimidine-7-carboxamide;

112) 4-amino-N-(6-methyl-1-((1-methyl-1H-indol-6-yl)amino)isoquinolin-5-yl)thieno[3,2-d]pyrimidine-7-carboxamide;

113) tert-butyl 6-((5-(4-aminothieno[3,2-d]pyrimidine-7-carboxamido)-6-methylisoquinolin-1-yl)amino)-1H-indazol-1-carboxylate;

114) N-(1-((1H-indazol-6-yl)amino)-6-methylisoquinolin-5-yl)-4-aminothieno[3,2-d]pyrimidine-7-carboxamide hydrochloride;

115) 4-amino-N-(1-((5-chloro-2-fluorophenyl)amino)-6-methylisoquinolin-5-yl)thieno[3,2-d]pyrimidine-7-carboxamide;

116) 4-amino-N-(1-((3-chloro-2-fluorophenyl)amino)-6-methylisoquinolin-5-yl)thieno[3,2-d]pyrimidine-7-carboxamide;

117) 4-amino-N-(1-((3-fluoro-4-(4-methylpiperazin-1-yl)phenyl)amino)-6-methylisoquinolin-5-yl)thieno[3,2-d]pyrimidine-7-carboxamide;

118) 4-amino-N-(1-((3-chloro-1-methyl-1H-indazol-6-yl)amino)-6-methylisoquinolin-5-yl)thieno[3,2-d]pyrimidine-7-carboxamide;

119) 4-amino-N-(6-methyl-1-((4-(prop-2-yn-1-yloxy)phenyl)amino)isoquinolin-5-yl)thieno[3,2-d]pyrimidine-7-carboxamide;

120) 4-amino-N-(1-((2-methoxy-4-morpholinophenyl)amino)-6-methylisoquinolin-5-yl)thieno[3,2-d]pyrimidine-7-carboxamide;

121) 4-amino-N-(1-(benzo[d]thiazol-6-ylamino)-6-methylisoquinolin-5-yl)thieno[3,2-d]pyrimidine-7-carboxamide;

122) N-(1-((1H-indazol-5-yl)amino)-6-methylisoquinolin-5-yl)-4-aminothieno[3,2-d]pyrimidine-7-carboxamide; *and*

123) 4-amino-N-(1-((3-chloro-2,4-difluorophenyl)amino)-6-methylisoquinolin-5-yl)thieno[3,2-d]pyrimidine-7-carboxamide;

[124) 4-amino-N-(1-((3-(dimethylamino)propyl)amino)-6-methylisoquinolin-5-yl)thieno[3,2-d]pyrimidine-7-carboxamide; and 125) 4-amino-N-(6-methyl-1-(piperidin-1-yl)isoquinolin-5-yl)thieno[3,2-d]pyrimidine-7-carboxamide,]

or [its] *a* pharmaceutically acceptable salt *thereof.*

7. A pharmaceutical composition comprising the compound of claim 1, *or a pharmaceutically acceptable salt thereof,* as an active ingredient.

8. The pharmaceutical composition of claim 7, wherein the pharmaceutical composition further comprises a drug selected from the group consisting of cell signal transduction inhibitors, mitosis inhibitors, alkylating agents, antimetabolites, antibiotics, growth factor inhibitors, cell cycle inhibitors, topoisomerase inhibitors, biological reaction modifiers, antihormonal agents, antiandrogen, cell differentiation/proliferation/survival inhibitors, apoptosis inhibitors, inflammation inhibitors and P-glycoprotein inhibitors.

9. A pharmaceutical formulation comprising the pharmaceutical composition of claim 7.

10. The pharmaceutical formulation of claim 9, wherein said formulation is an oral formulation.

11. The pharmaceutical formulation of claim 9, wherein said formulation is in the form of a tablet, a pill, powder, a capsule, syrup, an emulsion or a microemulsion.

12. A method for manufacturing a medicament containing the compound of claim 1, *or a pharmaceutically acceptable salt thereof,* as an active ingredient, said method comprising formulating the compound of claim 1, *or a pharmaceutically acceptable salt thereof,* into the medicament together with a pharmaceutically acceptable carrier.

13. A method for treating a cancer, which method comprises administering the compound of claim 1, *or a pharmaceutically acceptable salt thereof,* to a mammal in need thereof, wherein the cancer is liver cancer or melanoma.

14. The method of claim 13, wherein the compound, *or a pharmaceutically acceptable salt thereof,* is administered in combination with a drug selected from the group consisting of cell signal transduction inhibitors, mitosis inhibitors, alkylating agents, antimetabolites, antibiotics, growth factor inhibitors, cell cycle inhibitors, topoisomerase inhibitors, biological reaction modifiers, antihormonal agents, antiandrogen, cell differentiation/proliferation/survival inhibitors, apoptosis inhibitors, inflammation inhibitors, and P-glycoprotein inhibitors.

*15. A thieno[3,2-d]pyrimidine compound selected from the group consisting of:*

*71) 4-amino-N-(1-((3-(dimethylcarbamoyl)phenyl)amino)-6-methylisoquinolin-5-yl)thieno[3,2-d]pyrimidine-7-carboxamide;*

*72) 4-amino-N-(6-methyl-1-((3-(methylcarbamoyl)phenyl)amino)isoquinolin-5-yl)thieno[3,2-d]pyrimidine-7-carboxamide;*

*81) 4-amino-N-(1-((4-(2-methoxyethoxy)phenyl)amino)-6-methylisoquinolin-5-yl)thieno[3,2-d]pyrimidine-7-carboxamide;*

*95) 4-amino-N-(1-((4-(dimethylcarbamoyl)phenyl)amino)-6-methylisoquinolin-5-yl)thieno[3,2-d]pyrimidine-7-carboxamide;*

*124) 4-amino-N-(1-((3-(dimethylamino)propyl)amino)-6-methylisoquinolin-5-yl)thieno[3,2-d]pyrimidine-7-carboxamide; and*

*125) 4-amino-N-(6-methyl-1-(piperidin-1-yl)isoquinolin-5-yl)thieno[3,2-d]pyrimidine-7-carboxamide;*

*or a pharmaceutically acceptable salt thereof.*

*16. A pharmaceutical composition comprising a compound of claim 15, or a pharmaceutically acceptable salt thereof, as an active ingredient.*

*17. The pharmaceutical composition of claim 16, wherein the pharmaceutical composition further comprises a drug selected from the group consisting of cell signal transduction inhibitors, mitosis inhibitors, alkylating agents, antimetabolites, antibiotics, growth factor inhibitors, cell cycle inhibitors, topoisomerase inhibitors, biological reaction modifiers, antihormonal agents, antiandrogen, cell differentiation/proliferation/survival inhibitors, apoptosis inhibitors, inflammation inhibitors and P-glycoprotein inhibitors.*

*18. A pharmaceutical formulation comprising the pharmaceutical composition of claim 16.*

*19. The pharmaceutical formulation of claim 18, wherein said formulation is an oral formulation.*

*20. The pharmaceutical formulation of claim 18, wherein said formulation is in the form of a tablet, a pill, powder, a capsule, syrup, an emulsion or a microemulsion.*

*21. A method for treating cancer, which method comprises administering the pharmaceutical composition of claim 16 to a mammal in need thereof, wherein the cancer is liver cancer or melanoma.*

*22. The method of claim 21, wherein the pharmaceutical composition is administered in combination with a drug selected from the group consisting of cell signal transduction inhibitors, mitosis inhibitors, alkylating agents, antimetabolites, antibiotics, growth factor inhibitors, cell cycle inhibitors, topoisomerase inhibitors, biological reaction modifiers, antihormonal agents, antiandrogen, cell differentiation/proliferation/survival inhibitors, apoptosis inhibitors, inflammation inhibitors and P-glycoprotein inhibitors.*

*23. A thieno[3,2-d]pyrimidine compound having the following structure:*

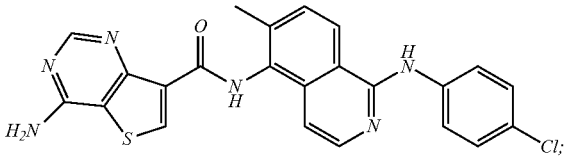

*or a pharmaceutically acceptable salt thereof.*

*24. A pharmaceutical composition comprising the thieno[3,2-d]pyrimidine compound of claim 23, or a pharmaceutically acceptable salt thereof, and a pharmaceutically acceptable excipient.*

*25. A method of treating a cancer, the method comprising administering the pharmaceutical composition of claim 24 to a mammal in need thereof, wherein the cancer is liver cancer or melanoma.*

*26. The method of claim 25 wherein the pharmaceutical composition is administered in combination with a cell signal transduction inhibitor drug.*

*27. A thieno[3,2-d]pyrimidine compound having the following structure:*

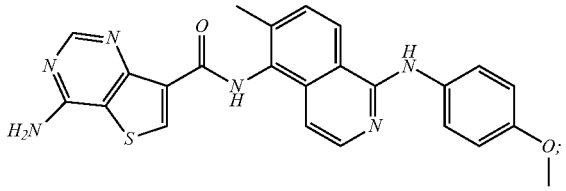

*or a pharmaceutically acceptable salt thereof.*

*28. A pharmaceutical composition comprising the thieno[3,2-d]pyrimidine compound of claim 27, or a pharmaceutically acceptable salt thereof, and a pharmaceutically acceptable excipient.*

*29. A method of treating a cancer, the method comprising administering the pharmaceutical composition of claim 28 to a mammal in need thereof, wherein the cancer is liver cancer or melanoma.*

*30. The method of claim 31 wherein the pharmaceutical composition is administered in combination with a cell signal transduction inhibitor drug.*

*31. A thieno[3,2-d]pyrimidine compound having the following structure:*

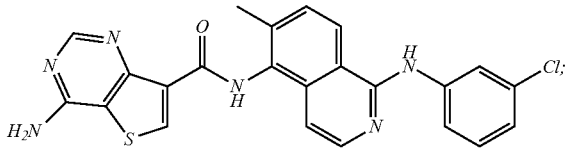

*or a pharmaceutically acceptable salt thereof.*

*32. A pharmaceutical composition comprising the thieno[3,2-d]pyrimidine compound of claim 31, or a pharmaceutically acceptable salt thereof, and a pharmaceutically acceptable excipient.*

*33. A method of treating a cancer, the method comprising administering the pharmaceutical composition of claim 32 to a mammal in need thereof, wherein the cancer is liver cancer or melanoma.*

*34. The method of claim 33 wherein the pharmaceutical composition is administered in combination with a cell signal transduction inhibitor drug.*

*35. A thieno[3,2-d]pyrimidine compound having the following structure:*

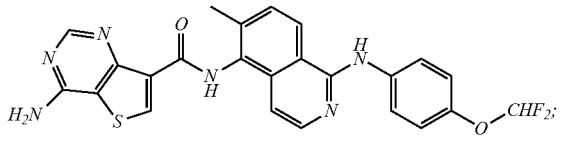

*or a pharmaceutically acceptable salt thereof.*

*36. A pharmaceutical composition comprising the thieno[3,2-d]pyrimidine compound of claim 35, or a pharmaceutically acceptable salt thereof, and a pharmaceutically acceptable excipient.*

*37. A method of treating a cancer, the method comprising administering the pharmaceutical composition of claim 36 to a mammal in need thereof, wherein the cancer is liver cancer or melanoma.*

*38. The method of claim 37 wherein the pharmaceutical composition is administered in combination with a cell signal transduction inhibitor drug.*

*39. A thieno[3,2-d]pyrimidine compound having the following structure:*

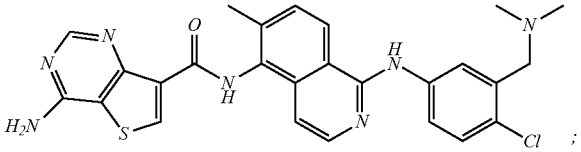

*or a pharmaceutically acceptable salt thereof.*

*40. A pharmaceutical composition comprising the thieno[3,2-d]pyrimidine compound of claim 39, or a pharmaceutically acceptable salt thereof, and a pharmaceutically acceptable excipient.*

*41. A method of treating a cancer, the method comprising administering the pharmaceutical composition of claim 40 to a mammal in need thereof, wherein the cancer is liver cancer or melanoma.*

*42. The method of claim 41 wherein the pharmaceutical composition is administered in combination with a cell signal transduction inhibitor drug.*

*43. A thieno[3,2-d]pyrimidine compound having the following structure:*

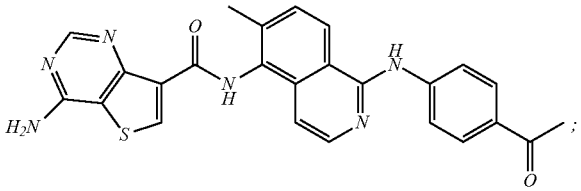

*or a pharmaceutically acceptable salt thereof.*

*44. A pharmaceutical composition comprising the thieno[3,2-d]pyrimidine compound of claim 43, or a pharmaceutically acceptable salt thereof, and a pharmaceutically acceptable excipient.*

*45. A method of treating a cancer, the method comprising administering the pharmaceutical composition of claim 44 to a mammal in need thereof, wherein the cancer is liver cancer or melanoma.*

*46. The method of claim 45 wherein the pharmaceutical composition is administered in combination with a cell signal transduction inhibitor drug.*

*47. A thieno[3,2-d]pyrimidine compound having the following structure:*

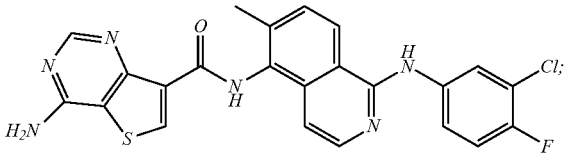

*or a pharmaceutically acceptable salt thereof.*

*48. A pharmaceutical composition comprising the thieno[3,2-d]pyrimidine compound of claim 47, or a pharmaceutically acceptable salt thereof, and a pharmaceutically acceptable excipient.*

*49. A method of treating a cancer, the method comprising administering the pharmaceutical composition of claim 48 to a mammal in need thereof, wherein the cancer is liver cancer or melanoma.*

50. The method of claim 49 wherein the pharmaceutical composition is administered in combination with a cell signal transduction inhibitor drug.

51. A thieno[3,2-d]pyrimidine compound having the following structure:

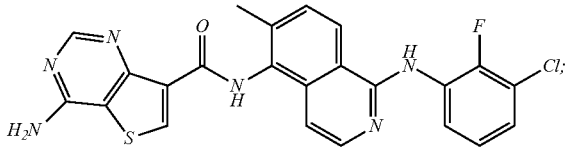

or a pharmaceutically acceptable salt thereof.

52. A pharmaceutical composition comprising the thieno[3,2-d]pyrimidine compound of claim 51, or a pharmaceutically acceptable salt thereof, and a pharmaceutically acceptable excipient.

53. A method of treating a cancer, the method comprising administering the pharmaceutical composition of claim 52 to a mammal in need thereof, wherein the cancer is liver cancer or melanoma.

54. The method of claims 53 wherein the pharmaceutical composition is administered in combination with a cell signal transduction inhibitor drug.

55. A method of preparing a thieno[3,2-d]pyrimidine compound, or a pharmaceutically acceptable salt thereof, according to reaction steps 1 to 3:

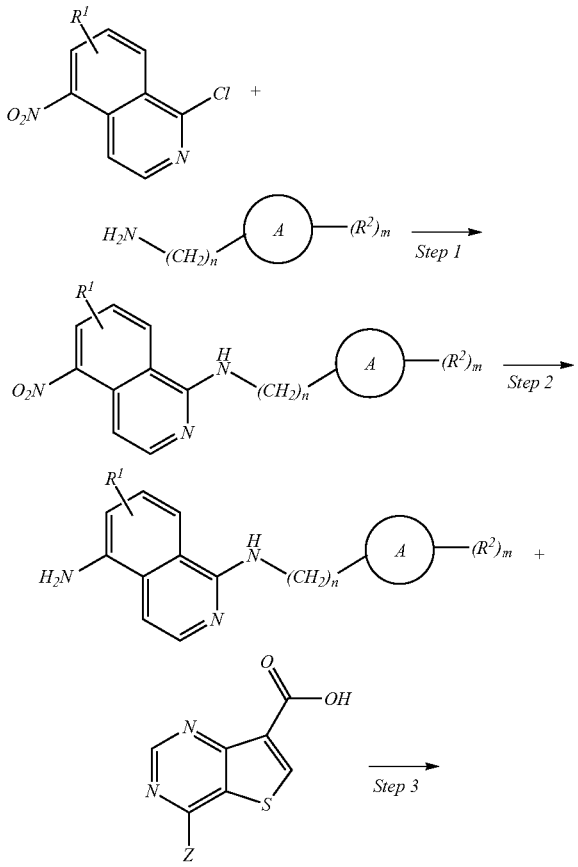

-continued

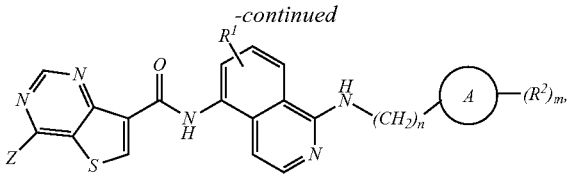

wherein:

A is $C_{6-10}$ aryl or 5- to 10-membered heteroaryl;

Z is hydrogen, $C_{1-3}$ alkyl or $NR^3R^4$, wherein said $R^3$ and $R^4$ are each independently hydrogen, $C_{1-6}$ alkyl or —$(CH_2)_q$-B—, B representing $NR^5R^6$, $C_{1-6}$ alkoxy, $C_{3-6}$ cycloalkyl or 3- to 6-membered heterocycloalkyl;

$R^1$ is hydrogen, halogen, $C_{1-3}$ alkyl or $C_{1-3}$ alkoxy, wherein said alkyl or alkoxy is unsubstituted or substituted with one or more halogen atoms;

$R^2$ is hydrogen, halogen, —$CF_3$, —$NO_2$, —OH, —CN, $C_{1-6}$ alkoxy, $C_{1-6}$ alkyl, $C_{2-4}$ alkenyl, $C_{2-4}$ alkynyl, —$NR^7R^8$, —$NHSO_2R^9$, —$SO_2R^{10}$, —$C(O)R^{11}$, —$NHC(O)R^{12}$, —$NHC(O)OR^{13}$, —$S(O)R^{14}$, $C_{3-6}$ cycloalkyl, 3- to 6-membered heterocycloalkyl, $C_{6-10}$ aryl, $C_{6-10}$ aryloxy, 5- to 10-membered heteroaryl or 5- to 10-membered heteroaryloxy, wherein said $R^2$ is connected to A by —$(CH_2)_p$- or substituted with $C_{1-4}$ alkyl, $C_{2-4}$alkynyl, $C_{1-4}$ alkylcarbonyl or one or more halogen atoms;

$R^5$, $R^6$, $R^7$, $R^8$, $R^9$, $R^{10}$, $R^{11}$, $R^{12}$, $R^{13}$ and $R^{14}$ are each independently hydrogen, —$NH_2$, $C_{1-6}$ alkyl, $C_{1-6}$ alkoxy, $C_{3-6}$ cycloalkyl or 3-to 6-membered heterocycloalkyl, said alkyl, alkoxy, cycloalkyl or heterocycloalkyl being unsubstituted or substituted with one or more halogen atoms;

m is an integer ranging from 0 to 3;

q is 0;

p is an integer ranging from 0 to 1; and n is 0 or 1.

56. The method of claim 55 wherein the compound has the structure:

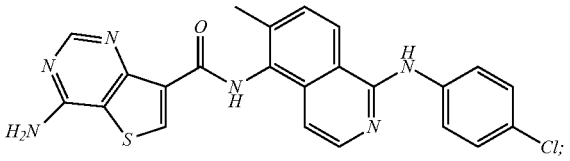

or a pharmaceutically acceptable salt thereof.

57. The method of claim 55 wherein the compound has the structure:

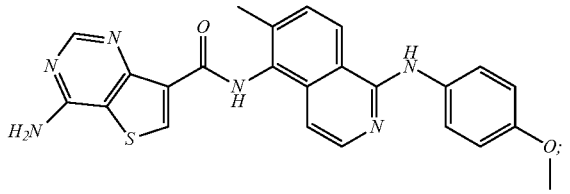

or a pharmaceutically acceptable salt thereof.

58. The method of claim 55 wherein the compound has the structure:

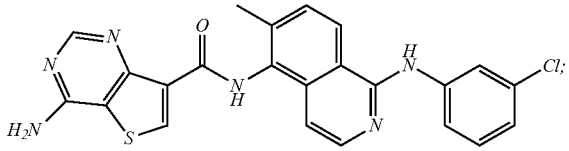

*or a pharmaceutically acceptable salt thereof.*

*59. The method of claim 55 wherein the compound has the structure:*

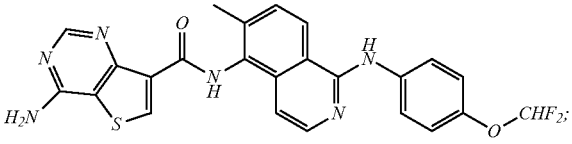

*or a pharmaceutically acceptable salt thereof.*

*60. The method of claim 55 wherein the compound has the structure:*

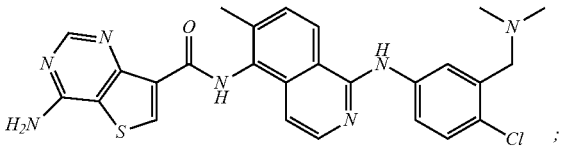

*or a pharmaceutically acceptable salt thereof.*

*61. The method of claim 55 wherein the compound is:*

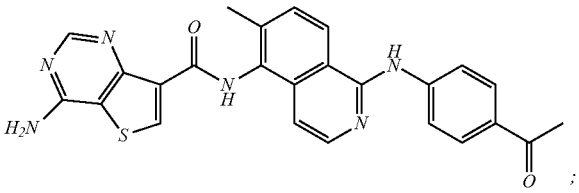

*or a pharmaceutically acceptable salt thereof.*

*62. The method of claim 55 wherein the compound is:*

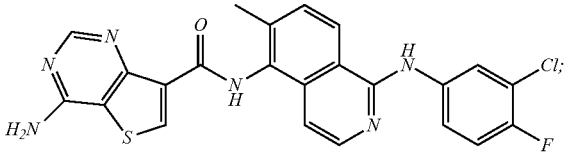

*or a pharmaceutically acceptable salt thereof.*

*63. The method of claim 55 wherein the compound is:*

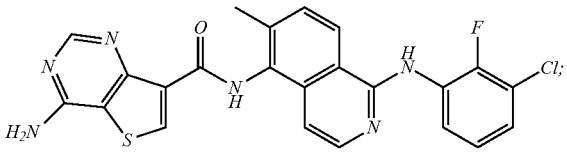

*or a pharmaceutically acceptable salt thereof.*

* * * * *